(12) United States Patent
Ozaki et al.

(10) Patent No.: US 9,068,572 B2
(45) Date of Patent: Jun. 30, 2015

(54) CENTRIFUGAL PUMP APPARATUS

(75) Inventors: Takayoshi Ozaki, Iwata (JP); Hiroyuki Yamada, Iwata (JP); Kenichi Suzuki, Iwata (JP); Ken Sugiura, Iwata (JP)

(73) Assignee: Thoratec Corporation, Pleasanton, CA (US)

( * ) Notice: Subject to any disclaimer, the term of this patent is extended or adjusted under 35 U.S.C. 154(b) by 322 days.

(21) Appl. No.: 13/810,165

(22) PCT Filed: Jun. 28, 2011

(86) PCT No.: PCT/JP2011/064768
§ 371 (c)(1),
(2), (4) Date: Jan. 14, 2013

(87) PCT Pub. No.: WO2012/008297
PCT Pub. Date: Jan. 19, 2012

(65) Prior Publication Data
US 2013/0121821 A1 May 16, 2013

(30) Foreign Application Priority Data

Jul. 12, 2010 (JP) .................................. 2010-158028

(51) Int. Cl.
*F04D 29/047* (2006.01)
*F04D 1/00* (2006.01)
(Continued)

(52) U.S. Cl.
CPC ................ *F04D 1/00* (2013.01); *F04D 29/041* (2013.01); *F04D 29/048* (2013.01);
(Continued)

(58) Field of Classification Search
CPC ... F04D 1/00; F04D 13/0666; F04D 29/0473; F04D 29/041; A61M 1/122; A61M 1/1017

USPC .......................... 417/423.12, 423.13; 604/151
See application file for complete search history.

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 102239334 A 11/2011
CN 102341600 A 2/2012
(Continued)

OTHER PUBLICATIONS

Extended European search report in EP Application No. 11806627.3 mailed on Oct. 8, 2014, 8 pages.
(Continued)

*Primary Examiner* — Charles Freay
(74) *Attorney, Agent, or Firm* — Kilpatrick Townsend & Stockton LLP

(57) ABSTRACT

This centrifugal blood pump apparatus includes an impeller provided in a blood chamber, a first permanent magnet provided in one surface of the impeller, and a second permanent magnet provided in an inner wall of the blood chamber, for attracting the first permanent magnet. The attractive force between the first permanent magnet and the second permanent magnet on the opening side of a sidewall of the blood chamber is set to be smaller than the attractive force between the first permanent magnet and the second permanent magnet on the opposite side of the opening. As a result, inclination of the impeller with respect to a dividing wall during pump operation can be prevented.

20 Claims, 41 Drawing Sheets

(51) Int. Cl.
F04D 29/041 (2006.01)
F04D 29/048 (2006.01)
F04D 29/22 (2006.01)
A61M 1/10 (2006.01)
A61M 1/12 (2006.01)
F04D 13/06 (2006.01)

(52) U.S. Cl.
CPC .......... F04D 29/2261 (2013.01); A61M 1/101 (2013.01); A61M 1/1015 (2014.02); A61M 1/1017 (2014.02); A61M 1/122 (2014.02); F04D 13/0666 (2013.01)

(56) References Cited

U.S. PATENT DOCUMENTS

| | | |
|---|---|---|
| 3,510,229 A | 5/1970 | Smith |
| 3,932,069 A | 1/1976 | Giardini et al. |
| 3,960,468 A | 6/1976 | Boorse et al. |
| 4,149,535 A | 4/1979 | Volder |
| 4,382,199 A | 5/1983 | Isaacson |
| 4,392,836 A | 7/1983 | Sugawara |
| 4,507,048 A | 3/1985 | Belenger et al. |
| 4,540,402 A | 9/1985 | Aigner |
| 4,549,860 A | 10/1985 | Yakich |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papantonakos |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,969,865 A | 11/1990 | Hwang et al. |
| 4,985,014 A | 1/1991 | Orejola |
| 4,995,857 A | 2/1991 | Arnold |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 3/1994 | Pasque |
| 5,290,236 A | 3/1994 | Mathewson |
| 5,306,295 A | 4/1994 | Kolff et al. |
| 5,312,341 A | 5/1994 | Turi |
| 5,332,374 A | 7/1994 | Kricker et al. |
| 5,346,458 A | 9/1994 | Afield |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,533,957 A | 7/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,190,304 B1 | 2/2001 | Downey et al. |
| 6,206,659 B1 | 3/2001 | Izraelev |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,351,048 B1 | 2/2002 | Schob et al. |
| 6,375,607 B1 | 4/2002 | Prem |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |

(56) References Cited

U.S. PATENT DOCUMENTS

| | | |
|---|---|---|
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0287022 A1 | 12/2005 | Yaehashi et al. |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1 | 1/2008 | La Rose et al. |
| 2008/0030895 A1 | 2/2008 | Obara et al. |
| 2008/0124231 A1 | 5/2008 | Yaegashi |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 58/9535 | 1/1983 |
| JP | 4-091396 A | 3/1992 |
| JP | 4-148094 A | 5/1992 |
| JP | 05/021197 U | 3/1993 |
| JP | 06/014538 U | 2/1994 |
| JP | 6-53790 U | 7/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004-209240 A | 7/2004 |
| JP | 2004/332566 A | 11/2004 |
| JP | 2004/346925 | 12/2004 |
| JP | 2004-346925 A | 12/2004 |
| JP | 2005/94955 | 4/2005 |
| JP | 2005-127222 A | 5/2005 |
| JP | 2005/270345 A | 10/2005 |
| JP | 2005/270415 A | 10/2005 |
| JP | 2005/287599 A | 10/2005 |
| JP | 2006-167173 A | 6/2006 |
| JP | 2007/002885 A | 1/2007 |
| JP | 2007/043821 | 2/2007 |
| JP | 2007/089972 | 4/2007 |
| JP | 2007-089972 A | 4/2007 |
| JP | 2007/089974 | 4/2007 |
| JP | 2007/215292 | 8/2007 |
| JP | 2007/247489 | 9/2007 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008-297997 A | 12/2008 |
| JP | 2006/254619 | 9/2009 |

(56) References Cited

FOREIGN PATENT DOCUMENTS

| JP | 2010-136863 | A | 6/2010 |
|---|---|---|---|
| WO | 93/07388 | A1 | 4/1993 |
| WO | 96/31934 | | 10/1996 |
| WO | 97/42413 | A1 | 11/1997 |
| WO | 2005/028000 | A1 | 3/2005 |
| WO | 2005/034312 | A2 | 4/2005 |
| WO | 2009/157408 | | 12/2009 |
| WO | 2010/067682 | A1 | 6/2010 |
| WO | 2010/101082 | A1 | 9/2010 |
| WO | 2011/013483 | A1 | 2/2011 |

OTHER PUBLICATIONS

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

European Search report Issued in European Patent Application No. 10/748,702.7, mailed Apr. 2, 2013.

Extended European Search Report issued in European Patent Application No. EP 10748677.1, mailed Nov. 19, 2012.

International Search Report (PCT/ISA/210) issued on Jul. 14, 2009, by Japanese Patent Office as the International Searching Authority for International Application No. PCT/JP2009/061318.

International Search Report and Written Opinion issued in PCT/JP2011/050925, mailed Apr. 12, 2011.

International Search Report and Written Opinion issued in PCT/JP2011/054134, mailed Apr. 12, 2011.

International Search Report and Written Opinion issued in PCT/JP2011/070450, mailed Dec. 13, 2011.

Kosaka, et al.,"Operating Point Control System for a Continuous Flow Artificial Heart: In Vitro Study," ASAIO Journal 2003, 6 pages.

Supplementary European Search Report issued in European Application No. 09/831,788.6, dated Jan. 7, 2013, 7 pages.

Terumo Heart, Inc., "Handled With Care—Significantly Reduce the Risk of Cell Damage," Terumo brochure, Apr. 2010, 2 pages.

Yamazaki, et al., "Development of a Miniature Intraventricular Axial Flow Blood Pump," ASAIO Journal, 1993, 7 pages.

International Search Report issued in International Patent Application No. PCT/JP2011/064768 dated Sep. 13, 2011.

International Search Report and Written Opinion of PCT/US2014/012448 mailed on Feb. 19, 2014, 8 pages.

FIG.36
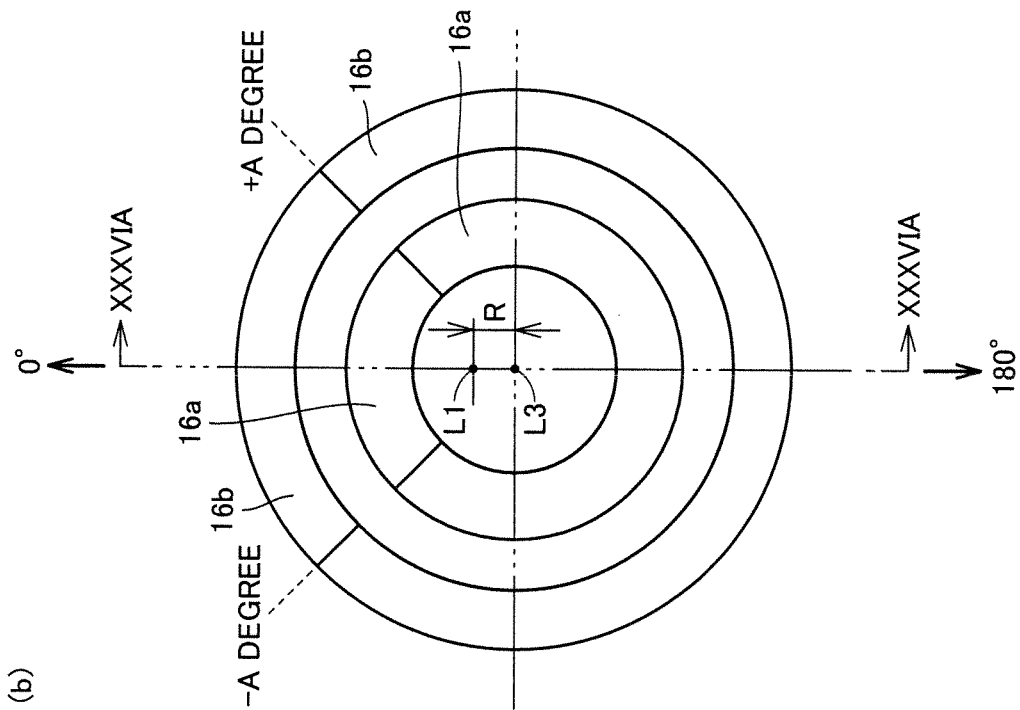
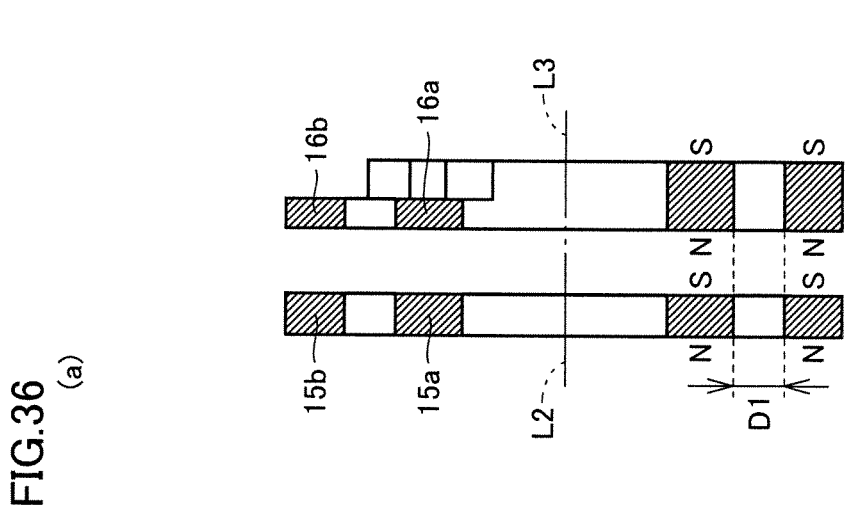

CENTRIFUGAL PUMP APPARATUS

RELATED APPLICATIONS

This application is the U.S. National Phase under 35 U.S.C. §371 of International Application No. PCT/JP2011/064768, filed on Jun. 28, 2011, which in turn claims the benefit of Japanese Application No. 2010-158028, filed on Jul. 12, 2010, the disclosures of which Applications are incorporated by reference herein.

TECHNICAL FIELD

The present invention relates to a centrifugal pump apparatus, and particularly to a centrifugal pump apparatus including an impeller for delivering fluid by centrifugal force during rotation.

BACKGROUND ART

In recent years, a centrifugal blood pump apparatus in which driving torque from an external motor is transmitted to an impeller in a blood chamber through magnetic coupling has increasingly been used as a blood circulation apparatus of an artificial heart-lung machine. According to such a centrifugal blood pump apparatus, physical contact between the blood chamber and the outside can be eliminated, thus preventing invasion of bacteria and the like into blood.

A centrifugal blood pump in Japanese Patent Laying-Open No. 2004-209240 (PTL 1) includes a housing having first to third chambers partitioned from one another by first and second dividing walls, an impeller rotatably provided in the second chamber (blood chamber), a magnetic element provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic bearing is formed in a surface of the second dividing wall facing the other surface of the impeller. Owing to attractive force acting on the one surface of the impeller from the electromagnet, attractive force acting on the other surface of the impeller from the permanent magnet in the rotor, and a hydrodynamic bearing effect of the grooves for hydrodynamic bearing, the impeller moves away from an inner surface of the second chamber and rotates without contacting.

A centrifugal blood pump in Japanese Patent Laying-Open No. 2006-167173 (PTL 2) includes a housing having first to third chambers partitioned from one another by first and second dividing walls, an impeller rotatably provided in the second chamber (blood chamber), a magnetic element provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first groove for hydrodynamic bearing is formed in a surface of the first dividing wall facing the one surface of the impeller, and a second groove for hydrodynamic bearing is formed in a surface of the second dividing wall facing the other surface of the impeller. Owing to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner surface of the second chamber and rotates without contacting.

A turbo-type pump in FIGS. 8 and 9 of Japanese Patent Laying-Open No. 4-91396 (PTL 3) includes a housing, an impeller rotatably provided in the housing, a first permanent magnet provided in one surface of the impeller, a rotor provided outside the housing, a second permanent magnet provided in the rotor to face the one surface of the impeller, a third permanent magnet provided in the other surface of the impeller, and a magnetic element provided in the housing to face the other surface of the impeller. A first groove for hydrodynamic bearing is formed in the one surface of the impeller, and a second groove for hydrodynamic bearing is formed in the other surface of the impeller. Owing to attractive force acting on the one surface of the impeller from the second permanent magnet in the rotor, attractive force acting on the other surface of the impeller from the magnetic element in the housing, and a hydrodynamic bearing effect of the first and second grooves for hydrodynamic bearing, the impeller moves away from an inner surface of the housing and rotates without contacting.

A clean pump in Japanese Utility Model Laying-Open No. 6-53790 (PTL 4) includes a housing, an impeller rotatably provided in the housing, a first permanent magnet provided in one surface of the impeller, a rotor provided outside the housing, a second permanent magnet provided in the rotor to face the one surface of the impeller, a magnetic element provided in the other surface of the impeller, and an electromagnet provided outside the housing to face the other surface of the impeller. A groove for hydrodynamic bearing is formed in the one surface of the impeller.

The electromagnet is actuated when a rotation speed of the impeller is lower than a prescribed rotation speed, and power supply to the electromagnet is stopped when the rotation speed of the impeller becomes higher than the prescribed rotation speed. Owing to attractive force acting on the one surface of the impeller from the second permanent magnet in the rotor and a hydrodynamic bearing effect of the groove for hydrodynamic bearing, the impeller moves away from an inner surface of the housing and rotates without contacting.

Furthermore, in a centrifugal blood pump in Japanese Patent Laying-Open No. 2007-89972 (PTL 5), a rotation centerline of a rotor is arranged at a position different from that of a centerline of a second chamber such that a rotation centerline of an impeller matches the centerline of the second chamber during rotation of the impeller in the centrifugal blood pump in PTL 2.

CITATION LIST

Patent Literature

PTL 1: Japanese Patent Laying-Open No. 2004-209240
PTL 2: Japanese Patent Laying-Open No. 2006-167173
PTL 3: Japanese Patent Laying-Open No. 4-91396
PTL 4: Japanese Utility Model Laying-Open No. 6-53790
PTL 5: Japanese Patent Laying-Open No. 2007-89972

SUMMARY OF INVENTION

Technical Problem

The pumps in PTLs 1 to 5 described above are common in the feature of axially (in a direction of a rotation axis of the impeller) supporting the impeller by the grooves for hydrodynamic bearing formed in a portion where the impeller and the housing face each other and radially (in a direction of a radius of the impeller) supporting the impeller by the attractive force between the permanent magnet provided in the impeller and the permanent magnet provided outside the housing.

In such a centrifugal pump apparatus, when rigidity for supporting the impeller (force required for moving the impeller by a unit length) is low, the impeller comes in contact with the inner wall of the blood chamber by application of vibration (accelerated vibration) involved with a user's operation. Therefore, supporting rigidity sufficiently high in each of the axial direction and the radial direction is required.

In order to increase rigidity for radially supporting the impeller, magnetic coupling force between the permanent magnet in the impeller and the permanent magnet on the housing side should only be increased. It is not easy, however, to increase that magnetic coupling force. In addition, in order to increase rigidity for axially supporting the impeller, dimensional data of the hydrodynamic bearing must be changed by increasing a diameter of the impeller or decreasing a levitation gap, or negative rigidity of a passive magnetic bearing formed by the permanent magnet on the impeller side and the permanent magnet on the housing side must be decreased. This is not easy, however. Namely, in a hydrodynamic bearing type centrifugal pump apparatus, initially, a flow rate, a pump head (pressure), and a minimum value of an interval between the blood chamber and the impeller are provided as the specifications. Then, a diameter of the impeller determines a rotation speed and a dimension of a groove for hydrodynamic bearing.

When the dimension of the groove for hydrodynamic bearing, the diameter of the impeller, the rotation speed, and the interval between the blood chamber and the impeller are determined, a load capacity is determined and hence magnetic coupling force balanced therewith is determined. When magnetic coupling force is determined, rigidity for supporting the impeller is also determined. Therefore, though it is necessary to increase the load capacity in order to increase rigidity for supporting the impeller, increase in the load capacity is limited, because the load capacity is dependent on viscosity of blood, a rotation speed of the impeller, a dimension of a groove for hydrodynamic bearing, and an interval between the blood chamber and the impeller.

In addition, in such a centrifugal pump apparatus, a sidewall of the blood chamber is formed cylindrically and a fluid outlet port for causing blood to flow out from an opening provided in the sidewall of the blood chamber to the outside of the housing is provided. When the impeller is rotated and blood flows, pressure distribution occurs in the blood chamber. The pressure of blood is low on the opening side of the sidewall of the blood chamber, and is high on the opposite side. Pressure distribution also occurs due to a flow rate balance of blood passing through a vane portion of the impeller. Therefore, particularly when a discharge flow rate is high, the impeller may move toward the opening side and be inclined with respect to the dividing wall in some cases (refer to FIG. 5). When the impeller moves and is inclined, the impeller comes in contact with the inner wall of the blood chamber and hemolysis occurs.

In the centrifugal blood pump in PTL 5, the rotation centerline of the impeller matches the centerline of the blood chamber, and thus, the load capacity can be increased. In this type, however, inclination of the impeller cannot be suppressed, and the load capacity in the axial direction cannot be improved although the load capacity in the radial direction can be increased.

In view of the above, a main object of the present invention is to provide a centrifugal pump apparatus in which inclination of the impeller with respect to the dividing wall during rotation of the impeller can be prevented.

Solution to Problem

A centrifugal pump apparatus according to the present invention is a centrifugal pump apparatus including a housing having first and second chambers partitioned from each other by a dividing wall, an impeller rotatably provided in the first chamber along the dividing wall, for delivering fluid by centrifugal force during rotation, and a drive unit provided in the second chamber, for driving the impeller to rotate with the dividing wall being interposed, the centrifugal pump apparatus including: a first magnetic element provided in one surface of the impeller; a second magnetic element provided in an inner wall of the first chamber facing the one surface of the impeller, for attracting the first magnetic element; a third magnetic element provided in the other surface of the impeller and attracted by the drive unit; and a fluid outlet port for allowing the fluid to flow to the outside of the housing from an opening provided in a sidewall of the first chamber. During rotation of the impeller, first attractive force acting on between the first and second magnetic elements and second attractive force acting on between the third magnetic element and the drive unit are balanced with each other substantially in a center of a movable range of the impeller in the first chamber. A first groove for hydrodynamic bearing is formed in the one surface of the impeller or in the inner wall of the first chamber facing the one surface and a second groove for hydrodynamic bearing is formed in the other surface of the impeller or in the dividing wall facing the other surface. At least one of the first and second magnetic elements is formed annularly around a rotation centerline of the impeller. A value of attractive force between the first and second magnetic elements on the opening side is set to be different from a value of attractive force between the first and second magnetic elements on an opposite side of the opening such that the impeller becomes parallel to the dividing wall during rotation of the impeller.

Preferably, the value of the attractive force between the first and second magnetic elements on the opening side is set to be smaller than the value of the attractive force between the first and second magnetic elements on the opposite side of the opening.

Further preferably, the second magnetic element is a permanent magnet formed annularly around the rotation centerline of the impeller, and a thickness of the second magnetic element on the opening side is smaller than a thickness of the second magnetic element on the opposite side of the opening.

Further preferably, the second magnetic element is a permanent magnet formed annularly around the rotation centerline of the impeller, and a facing area of the first and second magnetic elements on the opening side is smaller than a facing area of the first and second magnetic elements on the opposite side of the opening.

Further preferably, the second magnetic element is a permanent magnet formed annularly around the rotation centerline of the impeller, and a notch is provided in the second magnetic element on the opening side.

Further preferably, the first magnetic element includes a plurality of first permanent magnets that are different in diameter from each other and are each formed annularly, and the second magnetic element includes a plurality of second permanent magnets that are different in diameter from each other and are each formed annularly.

Further preferably, first magnetic poles of the plurality of second permanent magnets are all oriented in a direction of the impeller, and second magnetic poles of the plurality of second permanent magnets are all oriented in an opposite direction of the impeller, and second magnetic poles of the plurality of first permanent magnets are provided to face the first magnetic poles of the plurality of second permanent magnets, respectively. The centrifugal pump apparatus further includes: a fourth magnetic element attracted to a predetermined region on the opening side, of the second magnetic poles of the plurality of second permanent magnets.

Further preferably, a first magnetic pole of one of two adjacent second permanent magnets is oriented in a direction of the impeller, and a second magnetic pole of the other second permanent magnet is oriented in the direction of the impeller, and magnetic poles of the plurality of first permanent magnets are arranged to attract magnetic poles of the plurality of second permanent magnets, respectively. The centrifugal pump apparatus further includes: a fourth magnetic element attracted to a predetermined region on the opposite side of the opening, of the magnetic poles of the plurality of second permanent magnets on an opposite side of the impeller.

Further preferably, the sidewall of the first chamber facing a side surface of the impeller is formed cylindrically, and assuming that a direction of an end of the opening on an upstream side when viewed from a centerline of the sidewall of the first chamber is 0 degree and an opposite side thereof is 180 degrees, the opening side is the 0-degree direction side when viewed from the centerline of the sidewall of the first chamber, and the opposite side of the opening is the 180-degree direction side when viewed from the centerline of the sidewall of the first chamber. Attractive force between the first and second magnetic elements within a range of 0 degree±A degree (where the A degree is an angle that is larger than 0 degree and smaller than 180 degrees) when viewed from the centerline of the sidewall of the first chamber is smaller than attractive force between the first and second magnetic elements outside the range.

Further preferably, the drive unit includes a plurality of stator coils arranged annularly to face the third magnetic element of the impeller, for generating rotating magnetic field and rotating the impeller, and a centerline of the rotating magnetic field generated by the plurality of stator coils matches a centerline of the sidewall of the first chamber.

Further preferably, the drive unit includes: a plurality of fifth magnetic elements arranged annularly to face the third magnetic element of the impeller; and a plurality of stator coils wound around the plurality of fifth magnetic elements, respectively, for generating rotating magnetic field and rotating the impeller, and a centerline of the rotating magnetic field generated by the plurality of stator coils matches a centerline of the sidewall of the first chamber.

Further preferably, the drive unit includes: a rotor rotatably provided along the dividing wall in the second chamber; a fifth magnetic element provided in the rotor to face the third magnetic element, for attracting the third magnetic element; and a motor for rotating the rotor, and a rotation centerline of the rotor matches a centerline of the sidewall of the first chamber.

Another centrifugal pump apparatus according to the present invention is a centrifugal pump apparatus including a housing having first and second chambers partitioned from each other by a dividing wall, an impeller rotatably provided in the first chamber along the dividing wall, for delivering fluid by centrifugal force during rotation, and a drive unit provided in the second chamber, for driving the impeller to rotate with the dividing wall being interposed, the centrifugal pump apparatus including: a first magnetic element provided in one surface of the impeller; a second magnetic element provided in an inner wall of the first chamber facing the one surface of the impeller, for attracting the first magnetic element; a third magnetic element provided in the other surface of the impeller and attracted by the drive unit; and a fluid outlet port for allowing the fluid to flow to the outside of the housing from an opening provided in a sidewall of the first chamber. During rotation of the impeller, first attractive force acting on between the first and second magnetic elements and second attractive force acting on between the third magnetic element and the drive unit are balanced with each other substantially in a center of a movable range of the impeller in the first chamber. A first groove for hydrodynamic bearing is formed in the one surface of the impeller or in the inner wall of the first chamber facing the one surface and a second groove for hydrodynamic bearing is formed in the other surface of the impeller or in the dividing wall facing the other surface. Each of the first and second magnetic elements is formed annularly around a rotation centerline of the impeller. A corner of an end surface of the first or second magnetic element is chamfered such that attractive force between the first and second magnetic elements on the opening side becomes smaller than attractive force between the first and second magnetic elements on an opposite side of the opening when the impeller becomes eccentric toward the opening side due to hydrodynamic force.

Preferably, an outer-circumferential-side corner of the end surface of the second magnetic element is chamfered.

Further preferably, an inner-circumferential-side corner of the end surface of the first magnetic element is chamfered.

Further preferably, the drive unit includes a plurality of stator coils arranged annularly to face the third magnetic element of the impeller, for generating rotating magnetic field and rotating the impeller, and a centerline of the rotating magnetic field generated by the plurality of stator coils matches a centerline of the sidewall of the first chamber.

Further preferably, the drive unit includes: a plurality of fourth magnetic elements arranged annularly to face the third magnetic element of the impeller; and a plurality of stator coils wound around the plurality of fourth magnetic elements, respectively, for generating rotating magnetic field and rotating the impeller, and a centerline of the rotating magnetic field generated by the plurality of stator coils matches a centerline of the sidewall of the first chamber.

Further preferably, the drive unit includes: a rotor rotatably provided along the dividing wall in the second chamber; a fourth magnetic element provided in the rotor to face the third magnetic element, for attracting the third magnetic element; and a motor for rotating the rotor, and a rotation centerline of the rotor matches a centerline of the sidewall of the first chamber.

Further preferably, a centerline of the second magnetic element is arranged at a position different from that of a centerline of the sidewall of the first chamber such that the rotation centerline of the impeller matches the centerline of the sidewall of the first chamber during rotation of the impeller.

Further preferably, the fluid is blood, and the centrifugal pump apparatus is used for circulating the blood.

Advantageous Effects of Invention

As described above, according to the present invention, the impeller can be levitated at substantially the central position of the movable range of the impeller and inclination of the impeller during rotation can be suppressed. Therefore, mechanical contact between the impeller and the housing can be decreased, and the impeller can be levitated in a stable manner. In addition, hemolysis can be avoided in blood circulation.

BRIEF DESCRIPTION OF DRAWINGS

FIG. 36 is a diagram showing a permanent magnet shown in FIG. 34.

DESCRIPTION OF EMBODIMENTS

[First Embodiment]

Figure 1:
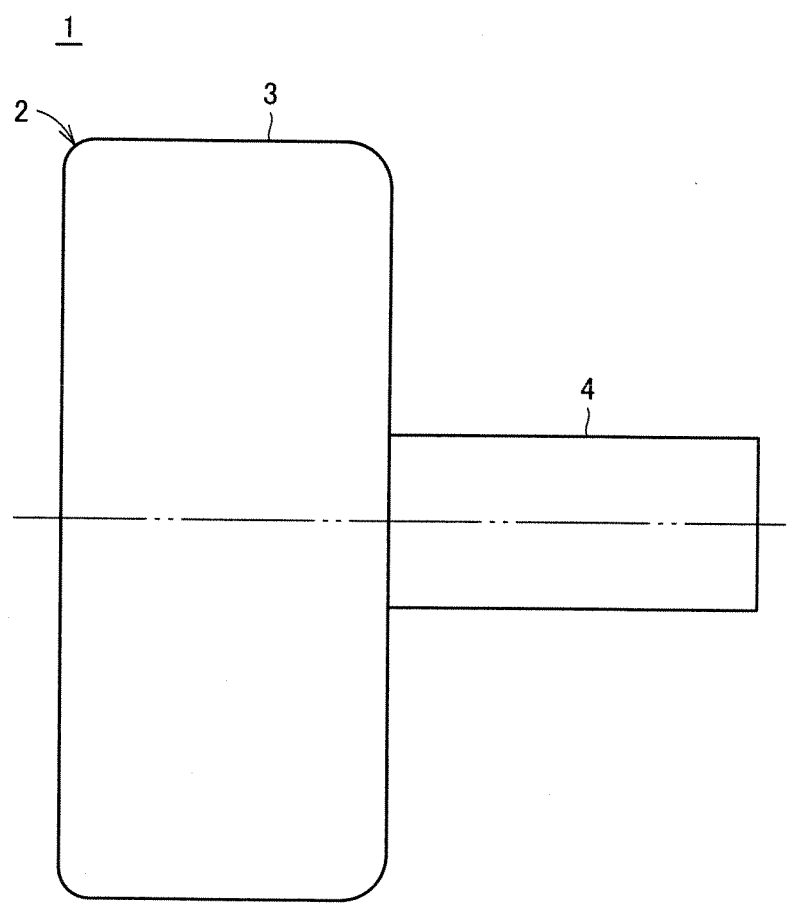
FIG. 1 is a front view showing the appearance of a pump unit of a centrifugal blood pump apparatus according to a first embodiment of the present invention.
Figure 2:
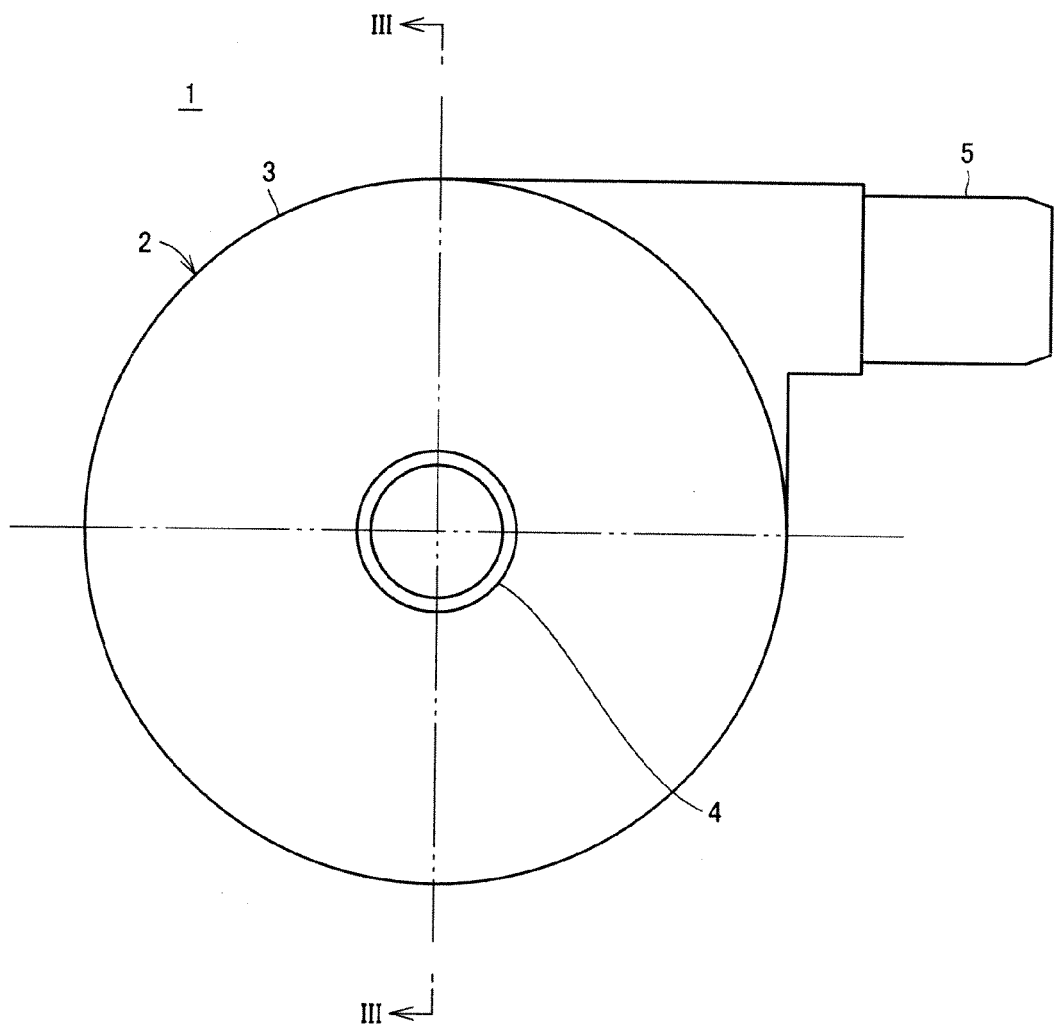
FIG. 2 is a side view of the pump unit shown in FIG. 1.

As shown in FIGS. 1 and 2, a pump unit 1 of a centrifugal blood pump apparatus according to a first embodiment includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
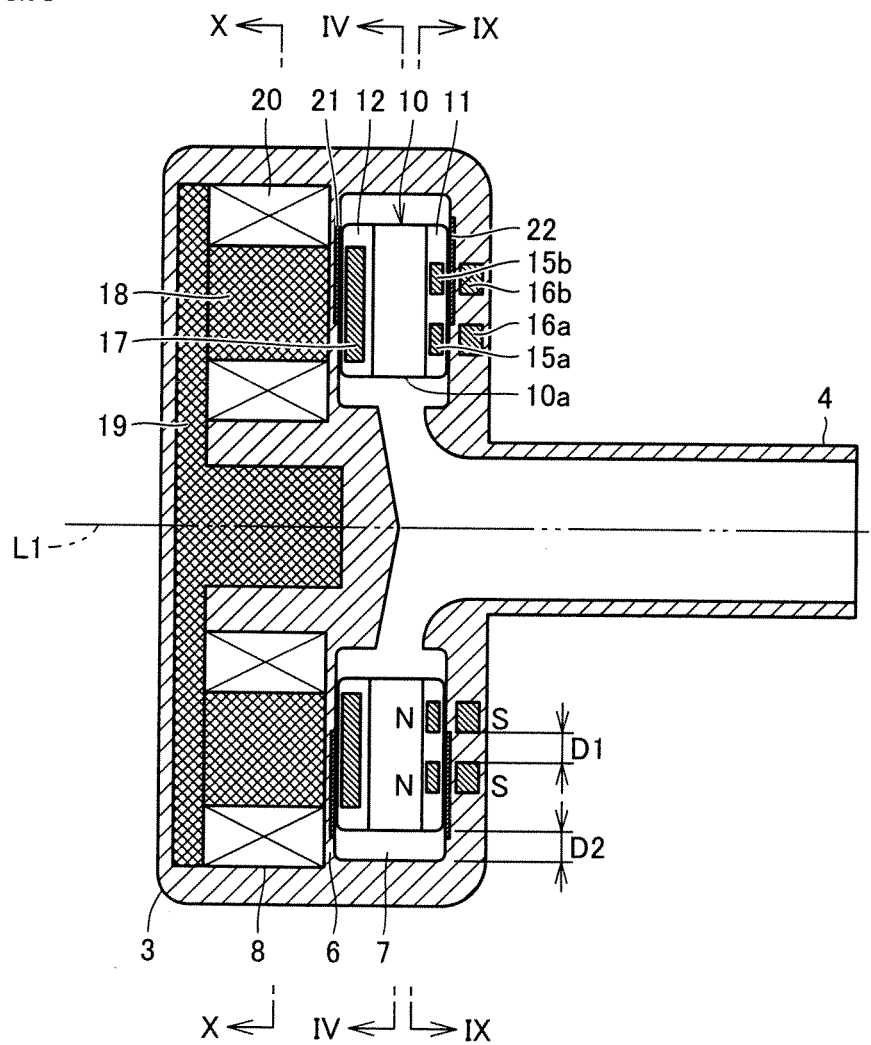
FIG. 3 is a cross-sectional view along the line III-III in FIG. 2.
Figure 4:
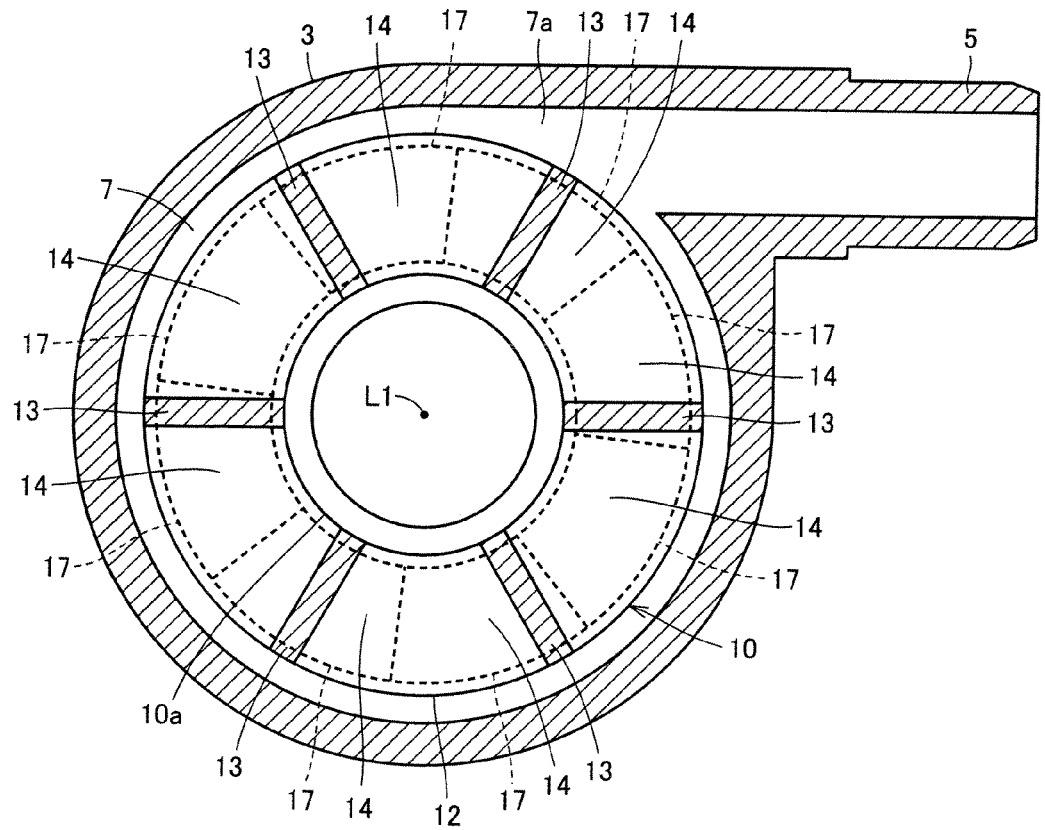
FIG. 4 is a cross-sectional view along the line IV-IV in FIG. 3.

In housing 2, as shown in FIG. 3, a blood chamber 7 and a motor chamber 8 partitioned from each other by a dividing wall 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side and shroud 12 is arranged on the dividing wall 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a in the center of impeller 10, and it extends with through hole 10a in impeller 10 as a starting point to an outer circumference such that blood passage 14 gradually increases in width. In other words, vane 13 is formed between two adjacent blood passages 14. In this first embodiment, the plurality of vanes 13 are formed at regular angular intervals, and they have the same shape. Thus, the plurality of blood passages 14 are provided at regular angular intervals and they have the same shape.

A sidewall of blood chamber 7 facing a side surface of impeller 10 is formed cylindrically and has an inner diameter larger than an outer diameter of impeller 10. A centerline L1 of the cylindrical sidewall matches a centerline of blood inlet port 4. An opening 7a is provided in a part of the sidewall of blood chamber 7. Cylindrical blood outlet port 5 is coupled to opening 7a. Blood outlet port 5 extends in the tangential direction of the cylindrical sidewall 7 of blood chamber 7 so as to allow smooth outflow of blood. When impeller 10 is driven to rotate, blood that has flowed in through blood inlet port 4 is delivered by centrifugal force from through hole 10a to an outer circumferential portion of impeller 10 via blood passages 14 and it flows out through opening 7a and blood outlet port 5 to the outside of housing 3.

Permanent magnets 15a, 15b (first magnetic elements) are embedded in shroud 11 and permanent magnets 16a, 16b (second magnetic elements) for attracting permanent magnets 15a, 15b respectively are embedded in an inner wall of blood chamber 7 facing shroud 11. Permanent magnets 15a, 15b, 16a, and 16b are provided to attract (in other words, bias) impeller 10 to the side opposite to motor chamber 8, that is, toward blood inlet port 4.

When impeller 10 is rotated, blood flows from blood inlet port 4 to blood outlet port 5 via opening 7a and blood pressure distribution occurs in blood chamber 7. Particularly when a discharge flow rate of blood is high, a difference between the pressure on the opening 7a side and the pressure on the opposite side of opening 7a is large. Therefore, as shown in FIG. 5, impeller 10 is attracted to the opening 7a side, and impeller 10 is inclined in such a state that a distance between impeller 10 and permanent magnets 16a, 16b on the opening 7a side is smaller than a distance between impeller 10 and permanent magnets 16a, 16b on the opposite side of opening 7a.

Figure 5:
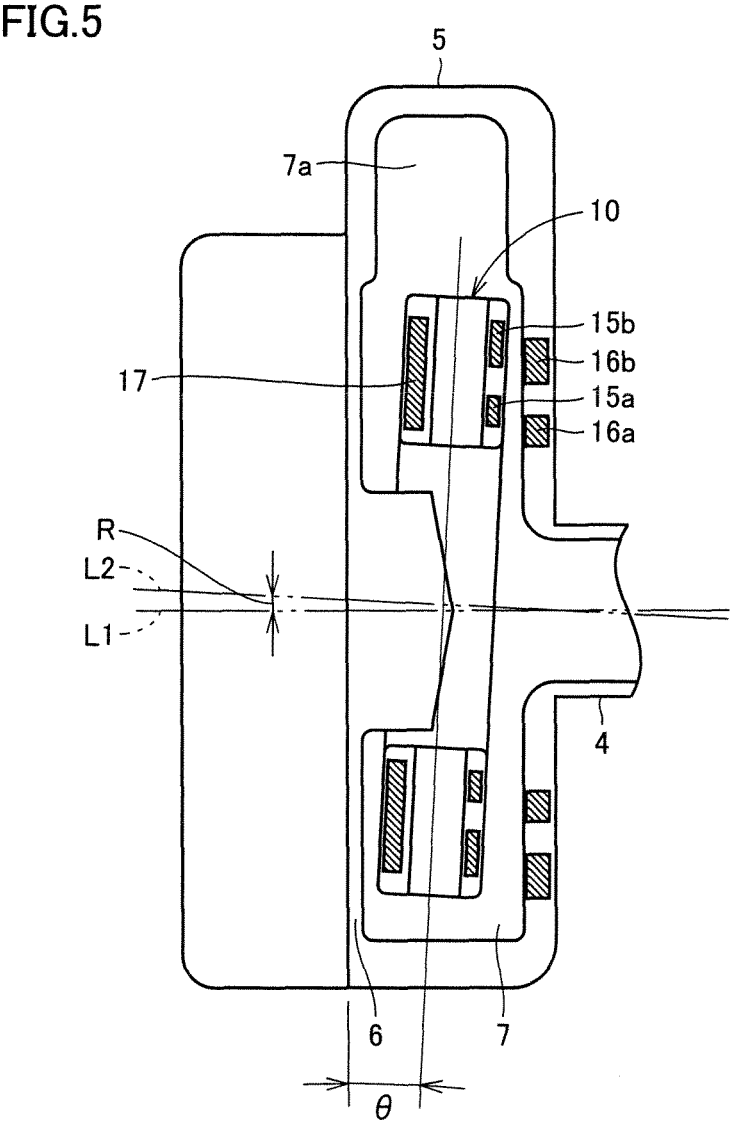
FIG. 5 is a diagram for describing problems of the centrifugal blood pump apparatus.

FIG. 5 shows a state where a rotation centerline L2 of impeller 10 has moved by a certain distance R from centerline L1 of the cylindrical sidewall of blood chamber 7 to the opening 7a side. FIG. 5 also shows a state where dividing wall 6 is not parallel to impeller 10 and a plane including dividing wall 6 and a plane including a center plane of impeller 10 intersect with each other at a certain angle θ on the opposite side of opening 7a.

Figure 6:
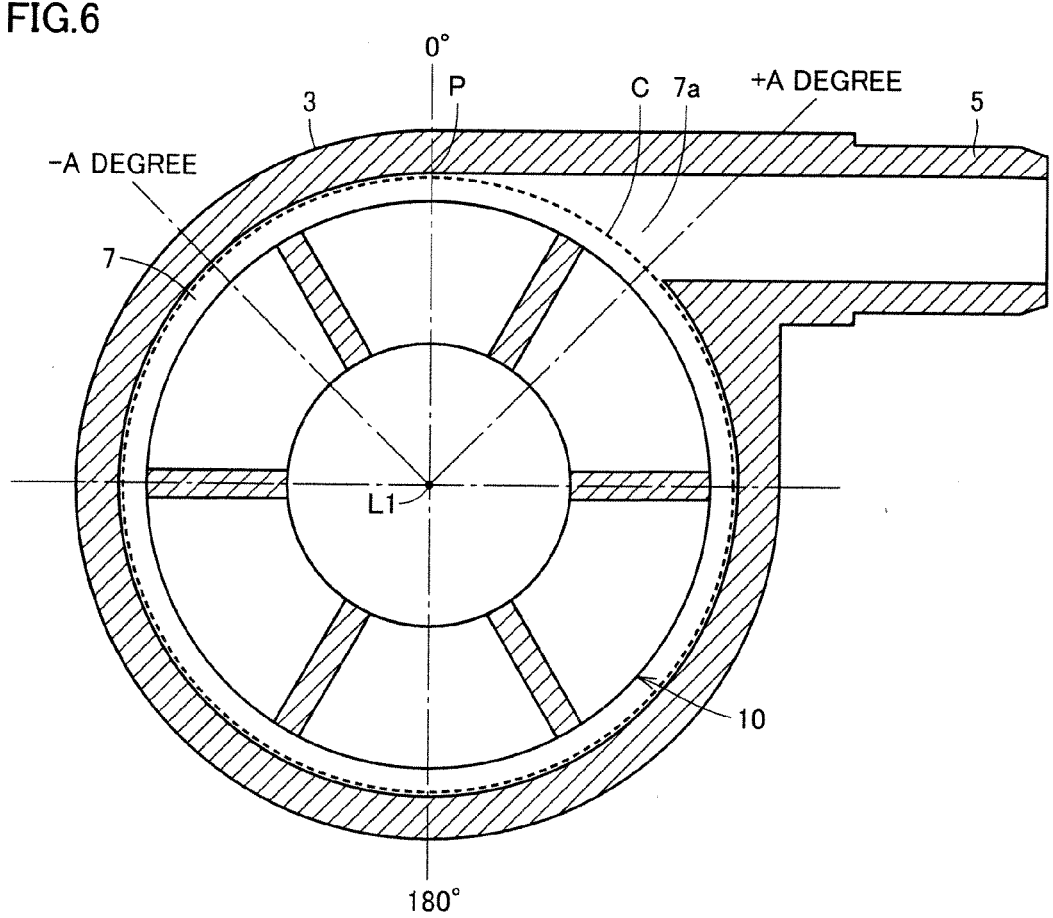
FIG. 6 is a diagram for describing a method for solving the problems described with reference to FIG. 5.

FIG. 6 is a diagram showing positional relation between centerline L1 of the sidewall of blood chamber 7 and opening 7a. In FIG. 6, housing 2 is cut in a plane orthogonal to centerline L1 of the sidewall of blood chamber 7 and including a centerline of a hole in blood outlet port 5. The sidewall of blood chamber 7 is formed along a circle C on this plane. A central point of circle C is an intersection point of this plane and centerline L1 of the sidewall of blood chamber 7. The hole in blood outlet port 5 extends in the tangential direction of circle C. In FIG. 6, impeller 10 rotates in a direction of rotation of clock hands and blood also rotates in this direction. A contact point P between the hole in blood outlet port 5 and circle C is located at an end of opening 7a on the upstream side (the left side in FIG. 6) in the sidewall of blood chamber 7.

Assume that a direction of contact point P (the end of opening 7a on the upstream side) is defined as 0 degree and the opposite direction is defined as 180 degrees when viewed from the central point of circle C (centerline L1 of the sidewall of blood chamber 7). A levitation position of impeller 10 is determined by a balance among hydrodynamic force of blood, hydrodynamic force of the hydrodynamic bearing, attractive force between permanent magnets 15a, 15b and permanent magnets 16a, 16b, attractive force between the permanent magnet on the impeller 10 side and the magnetic element on the motor side, and the like. In this first embodiment, in order to suppress inclination of impeller 10, attractive force between permanent magnets 15a, 15b and permanent magnets 16a, 16b on the opening 7a side (within a range of 0 degree±A degree when viewed from central points of permanent magnets 16a and 16b) is set to be smaller than attractive force between permanent magnets 15a, 15b and permanent magnets 16a, 16b on the opposite side of opening 7a. The A degree is a prescribed angle that is larger than 0 degree and smaller than 180 degrees. The A degree is preferably 60 degrees.

Figure 7:
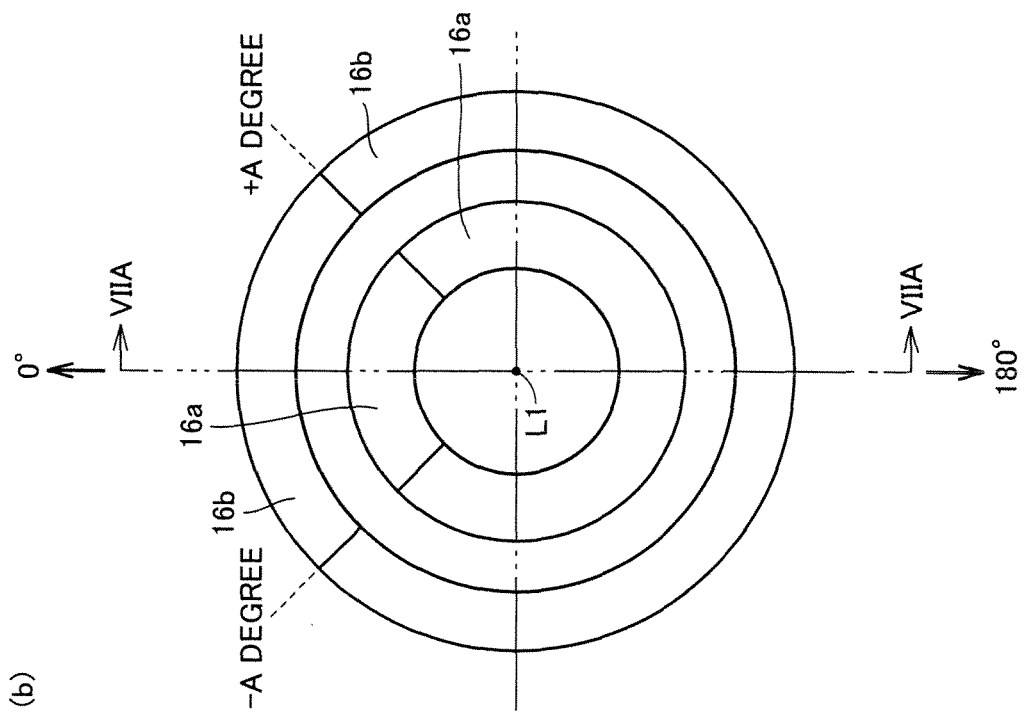
FIG. 7 is a diagram showing a configuration of a permanent magnet shown in FIG. 3.

FIGS. 7(a) and (b) are diagrams showing a structure of permanent magnets 15a, 15b, 16a, and 16b and FIG. 7(a) is a cross-sectional view along the line VIIA-VIIA in FIG. 7(b). FIGS. 7(a) and (b) show a state where centerline L1 of the cylindrical sidewall of blood chamber 7 matches rotation centerline L2 of impeller 10. Each of permanent magnets 15a, 15b is formed annularly, and an outer diameter of permanent magnet 15a is smaller than an inner diameter of permanent magnet 15b. Permanent magnets 15a, 15b are coaxially provided, and central points of respective permanent magnets 15a, 15b are both arranged on rotation centerline L2 of impeller 10. The N-poles of permanent magnets 15a, 15b are oriented in the same direction.

On the other hand, each of permanent magnets 16a, 16b is also formed annularly. An outer diameter and an inner diameter of permanent magnet 16a are the same as the outer diameter and the inner diameter of permanent magnet 15a. An outer diameter and an inner diameter of permanent magnet 16b are the same as the outer diameter and the inner diameter of permanent magnet 15b. Permanent magnets 16a, 16b are coaxially provided, and central points of respective permanent magnets 16a, 16b are both arranged on centerline L1 of the cylindrical sidewall of blood chamber 7. The N-poles of permanent magnets 16a, 16b are oriented in the same direction. The S-poles of permanent magnets 15a, 15b face the N-poles of permanent magnets 16a, 16b.

As described with reference to FIG. 6, in order to set the attractive force between permanent magnets 15a, 15b and permanent magnets 16a, 16b on the opening 7a side (within the range of 0 degree±A degree) to be smaller than the attractive force between permanent magnets 15a, 15b and permanent magnets 16a, 16b on the opposite side of opening 7a, the thickness of permanent magnets 16a, 16b on the opening 7a side (within the range of 0 degree±A degree) is small. The A degree is a prescribed angle that is larger than 0 degree and smaller than 180 degrees. The A degree is preferably 60 degrees.

In other words, within the range of 0 degree±A degree when viewed from the central points of permanent magnets 16a and 16b, a concave portion of a prescribed depth is formed in a back surface of permanent magnets 16a, 16b (a surface opposite to a surface facing permanent magnets 15a, 15b). As a result, the attractive force between permanent magnets 15a, 15b and permanent magnets 16a, 16b on the opening 7a side can be set to be smaller than the attractive force between permanent magnets 15a, 15b and permanent magnets 16a, 16b on the opposite side of opening 7a, and impeller 10 can become parallel to dividing wall 6 during rotation. Therefore, contact of impeller 10 with the inner wall of blood chamber 7 can be prevented.

As shown in FIG. 3, an interval D1 between permanent magnets 15a and 15b (i.e., interval between permanent magnets 16a and 16b) is set to be larger than a distance D2 that is a half of a movable distance of impeller 10 in the radial direction (i.e., distance of a difference between the inner diameter of blood chamber 7 and the outer diameter of impeller 10) (D1>D2). This is because, when impeller 10 moves in the radial direction to a maximum extent while relation of D1<D2 is satisfied, permanent magnets 15a and 16b interfere with each other and permanent magnets 15b and 16a interfere with each other and hence returning force for returning impeller 10 to a central position of the pump becomes unstable.

Since two pairs of permanent magnets 15a and 16a and permanent magnets 15b and 16b are provided in the radial direction of impeller 10, rigidity for supporting impeller 10 in the radial direction can be increased as compared with a case where only a pair of permanent magnets is provided in the radial direction of impeller 10.

Instead of providing permanent magnets 15a, 15b and permanent magnets 16a, 16b in shroud 11 and the inner wall of blood chamber 7, respectively, a permanent magnet may be provided in one of shroud 11 and the inner wall of blood chamber 7, and a magnetic element may be provided in the other. Either a soft magnetic element or a hard magnetic element may be used as the magnetic element.

Though FIGS. 7(a) and (b) show a case where opposing surfaces of permanent magnets 15a and 16a are identical in size and opposing surfaces of permanent magnets 15b and 16b are identical in size, in order to prevent lowering in rigidity of impeller 10 due to attractive force of permanent magnets 15a, 15b and permanent magnets 16a, 16b, opposing surfaces of permanent magnets 15a and 16a may be different in size from each other and opposing surfaces of permanent magnets 15b and 16b may be different in size from each other. By differing the size of the opposing surfaces of permanent magnets 15a, 15b and permanent magnets 16a, 16b, an amount of change in attractive force, that is, negative rigidity, which varies depending on a distance therebetween, can be suppressed to be small and lowering in rigidity for supporting impeller 10 can be prevented.

In FIGS. 7(a) and (b), each of permanent magnets 15a, 15b, 16a, and 16b is annularly formed. However, each of permanent magnets 15a, 15b may be annularly formed and each of permanent magnets 16a, 16b may be formed in an arc shape and two of the permanent magnets may be aligned at regular angular intervals in a direction of rotation of impeller 10. In contrast, each of permanent magnets 16a, 16b may be formed annularly, and each of permanent magnets 15a, 15b may be formed in an arc shape and two of the permanent magnets may be aligned at regular angular intervals in a direction of rotation of impeller 10. Alternatively, each of permanent magnets 15a, 15b or each of permanent magnets 16a, 16b may be formed in a shorter arc shape and a plurality of the permanent magnets may be aligned at regular angular intervals in a direction of rotation of impeller 10.

As shown in FIGS. 3 and 4, a plurality of (e.g., eight) permanent magnets 17 are embedded in shroud 12. The plurality of permanent magnets 17 are arranged at regular angular intervals along the same circle such that adjacent magnetic poles thereof are different from each other. In other words, permanent magnet 17 having the N-pole oriented to the motor chamber 8 side and permanent magnet 17 having the S-pole oriented to the motor chamber 8 side are alternately arranged at regular angular intervals along the same circle.

Figure 10:
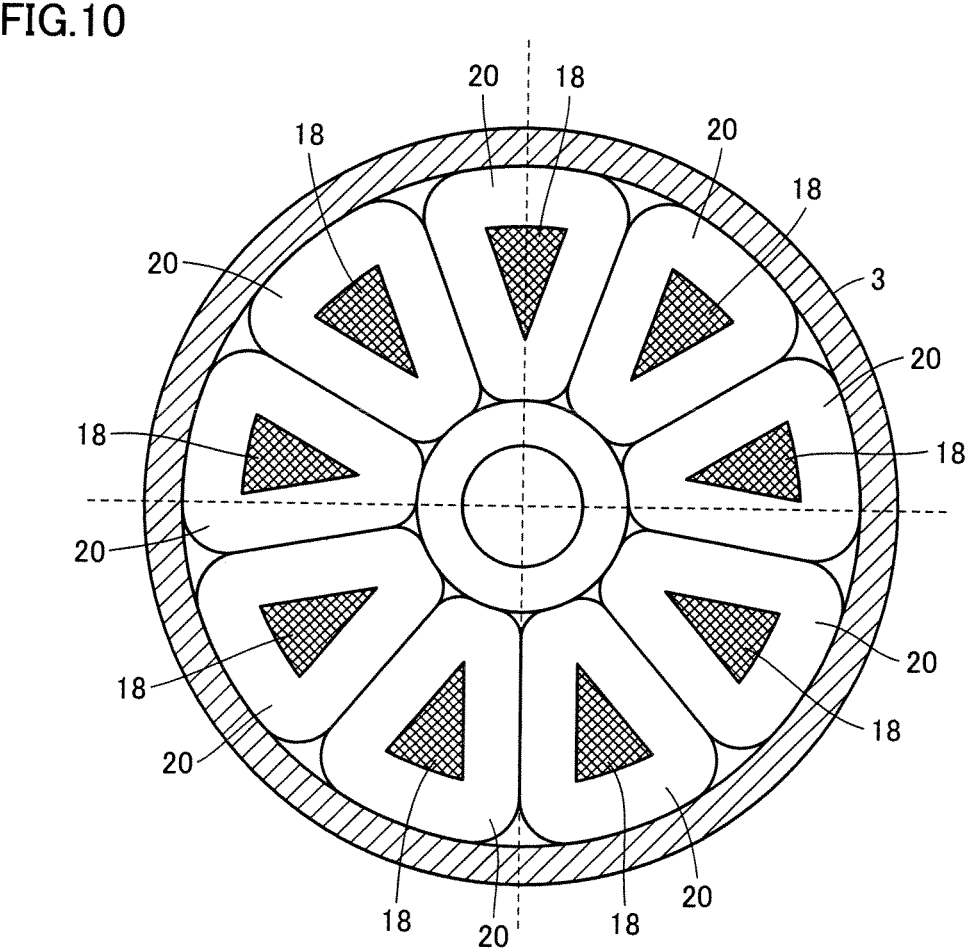
FIG. 10 is a cross-sectional view along the line X-X in FIG. 3.

As shown in FIGS. 3 and 10, a plurality of (e.g., nine) magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped yoke 19. A coil 20 is wound around each magnetic element 18.

Figure 11:
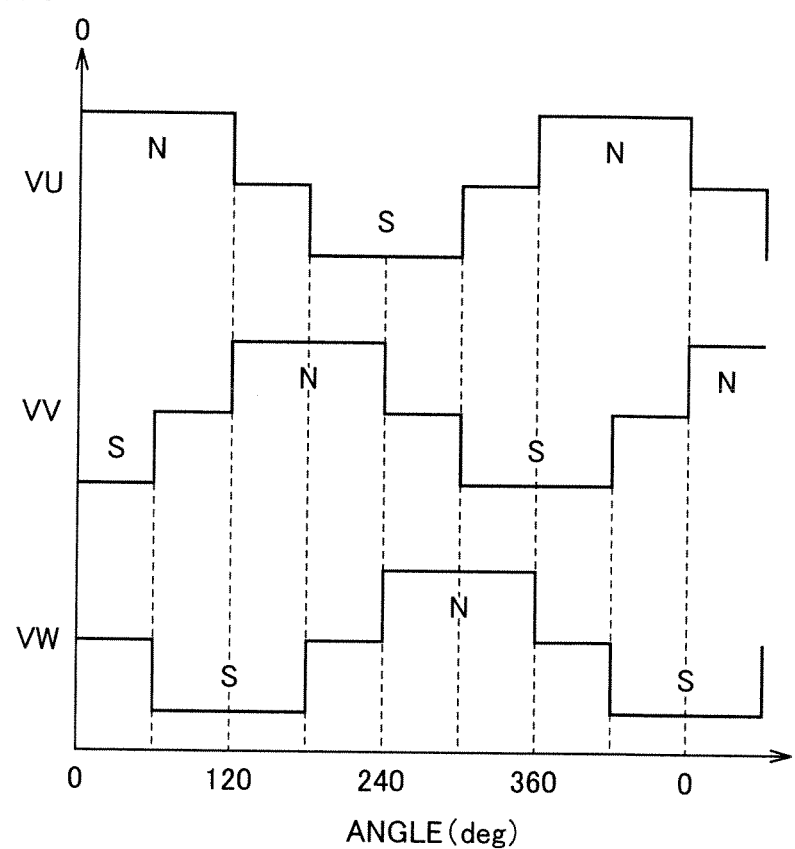
FIG. 11 is a time chart illustrating voltages applied to a plurality of coils shown in FIG. 10.

Voltages are applied to nine coils 20 in a power distribution system shifted by 120 degrees, for example. That is, nine coils 20 are divided into groups each including three coils. Voltages VU, VV and VW as shown in FIG. 11 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees and becomes the S-pole during the period of 180 to 300 degrees. Voltage VV is delayed in phase from voltage VU by 120 degrees, and voltage VW is delayed in phase from voltage VV by 120 degrees. Thus, rotating magnetic field can be formed by applying voltages VU, VV and VW to first to third coils 20, respectively, so that impeller 10 can be rotated by attractive force and repulsion force between the plurality of magnetic elements 18 and the plurality of permanent magnets 17 in impeller 10. A centerline of the rotating magnetic field generated by the plurality of coils 20 matches centerline L1 of the cylindrical sidewall of blood chamber 7.

When impeller 10 is rotating at a rated rotation speed, attractive force between permanent magnets 15a, 15b and permanent magnets 16a, 16b and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be lowered. In addition, a surface of impeller 10 and a surface of an inner wall of housing 2 are not damaged (no projections and recesses in the surfaces) during the relative slide, and moreover, impeller 10 is readily levitated from housing 2 without contacting even when hydrodynamic force is low during low-speed rotation. Accordingly, occurrence of hemolysis due to the relative slide between impeller 10 and housing 2 or occurrence of thrombus due to small damage (projections and recesses) to the surfaces which occurs during the relative slide is avoided.

A plurality of grooves for hydrodynamic bearing 21 are formed in a surface of dividing wall 6 facing shroud 12 of impeller 10, and a plurality of grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

Figure 8:
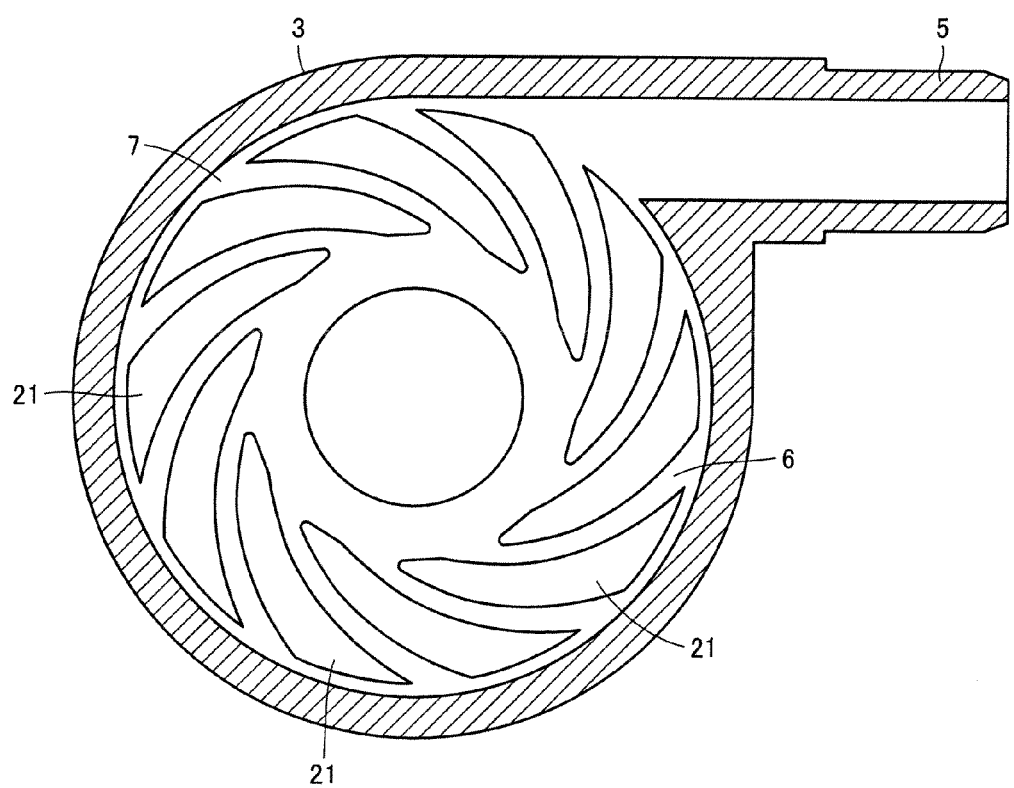
FIG. 8 is a cross-sectional view showing a state where an impeller has been removed from the cross-sectional view along the line IV-IV in FIG. 3.

Specifically, as shown in FIG. 8, the plurality of grooves for hydrodynamic bearing 21 are each formed with a size corresponding to shroud 12 of impeller 10. Each of grooves for hydrodynamic bearing 21 has one end on an edge (circumference) of a circular portion slightly distant from a center of dividing wall 6, and extends spirally (in other words, in a curved manner) toward a portion near an outer edge of dividing wall 6 such that groove for hydrodynamic bearing 21 gradually increases in width. The plurality of grooves for hydrodynamic bearing 21 have substantially the same shape, and they are arranged at substantially regular intervals. Groove for hydrodynamic bearing 21 is a concave portion, and it preferably has a depth of about 0.005 to 0.4 mm. It is preferable that about 6 to 36 grooves for hydrodynamic bearing 21 be provided.

In FIG. 8, ten grooves for hydrodynamic bearing 21 are arranged equiangularly with respect to a central axis of impeller 10. Since groove for hydrodynamic bearing 21 has a so-called inward spiral groove shape, clockwise rotation of impeller 10 causes increase in fluid pressure from an outer diameter portion toward an inner diameter portion of groove for hydrodynamic bearing 21. As a result, repulsion force is generated between impeller 10 and dividing wall 6 and it acts as hydrodynamic force.

In this manner, owing to the hydrodynamic bearing effect produced between impeller 10 and the plurality of grooves for hydrodynamic bearing 21, impeller 10 moves away from dividing wall 6 and rotates without contacting. Accordingly, a blood flow path is secured between impeller 10 and dividing wall 6, thus preventing occurrence of blood accumulation therebetween and the resultant thrombus. Further, in a normal state, grooves for hydrodynamic bearing 21 perform a stirring function between impeller 10 and dividing wall 6, thus preventing occurrence of partial blood accumulation therebetween.

Instead of providing grooves for hydrodynamic bearing 21 in dividing wall 6, grooves for hydrodynamic bearing 21 may be provided in a surface of shroud 12 of impeller 10.

It is preferable that a corner portion of groove for hydrodynamic bearing 21 be rounded to have R of at least 0.05 mm. As a result, occurrence of hemolysis can further be lessened.

Figure 9:
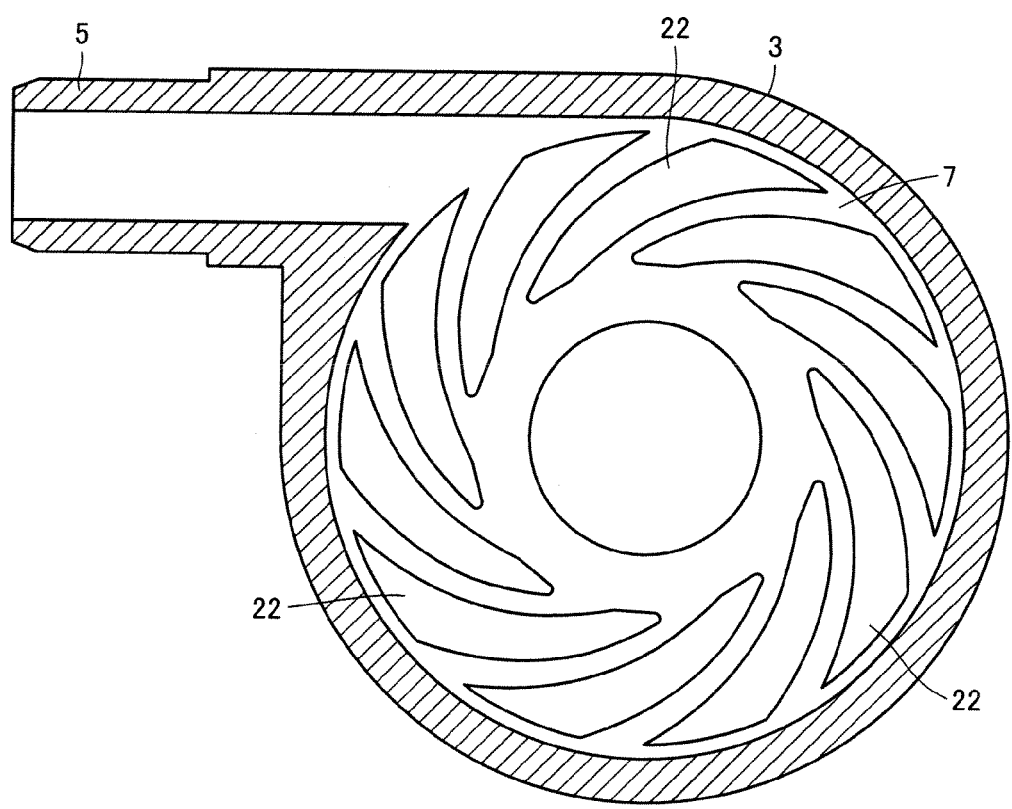
FIG. 9 is a cross-sectional view showing the state where the impeller has been removed from a cross-sectional view along the line IX-IX in FIG. 3.

As with the plurality of grooves for hydrodynamic bearing 21, as shown in FIG. 9, the plurality of grooves for hydrodynamic bearing 22 are formed with a size corresponding to shroud 11 of impeller 10. Each of grooves for hydrodynamic bearing 22 has one end on the edge (circumference) of the circular portion slightly distant from the center of the inner wall of blood chamber 7, and extends spirally (in other words, in a curved manner) toward the portion near the outer edge of the inner wall of blood chamber 7 such that groove for hydrodynamic bearing 22 gradually increases in width. The plurality of grooves for hydrodynamic bearing 22 have substantially the same shape and they are arranged at substantially regular intervals. Groove for hydrodynamic bearing 22 is a concave portion and it preferably has a depth of about 0.005 to 0.4 mm. It is preferable that about 6 to 36 grooves for hydrodynamic bearing 22 be provided. In FIG. 9, ten grooves for hydrodynamic bearing 22 are equiangularly arranged with respect to the central axis of impeller 10.

Owing to the hydrodynamic bearing effect produced between impeller 10 and the plurality of grooves for hydrodynamic bearing 22, impeller 10 moves away from the inner wall of blood chamber 7 and rotates without contacting. In addition, when pump unit 1 is subjected to external impact or when the hydrodynamic force generated by grooves for hydrodynamic bearing 21 becomes excessive, impeller 10 can be prevented from being in close contact with the inner wall of blood chamber 7. The hydrodynamic force generated by grooves for hydrodynamic bearing 21 may be different from the hydrodynamic force generated by grooves for hydrodynamic bearing 22.

Grooves for hydrodynamic bearing 22 may be provided in a surface of shroud 11 of impeller 10, rather than on the inner wall side of blood chamber 7. It is preferable that a corner portion of groove for hydrodynamic bearing 22 be rounded to have R of at least 0.05 mm. As a result, occurrence of hemolysis can further be lessened.

It is preferable that impeller 10 rotate in a state where a gap between shroud 12 of impeller 10 and dividing wall 6 is substantially equal to a gap between shroud 11 of impeller 10 and the inner wall of blood chamber 7. If one of the gaps becomes narrower due to serious disturbance such as hydrodynamic force acting on impeller 10, it is preferable that grooves for hydrodynamic bearing 21 and 22 have different shapes, so that the hydrodynamic force generated by the grooves for hydrodynamic bearing on the narrower side becomes higher than the hydrodynamic force generated by the other grooves for hydrodynamic bearing to make the gaps substantially equal to each other.

While both of grooves for hydrodynamic bearing 21 and 22 have the inward spiral groove shape in FIGS. 8 and 9, grooves for hydrodynamic bearing 21 and 22 having another shape may be used. Nevertheless, for blood circulation, it is preferable to employ grooves for hydrodynamic bearing 21 and 22 having the inward spiral groove shape that allows smooth flow of blood.

Figure 12:
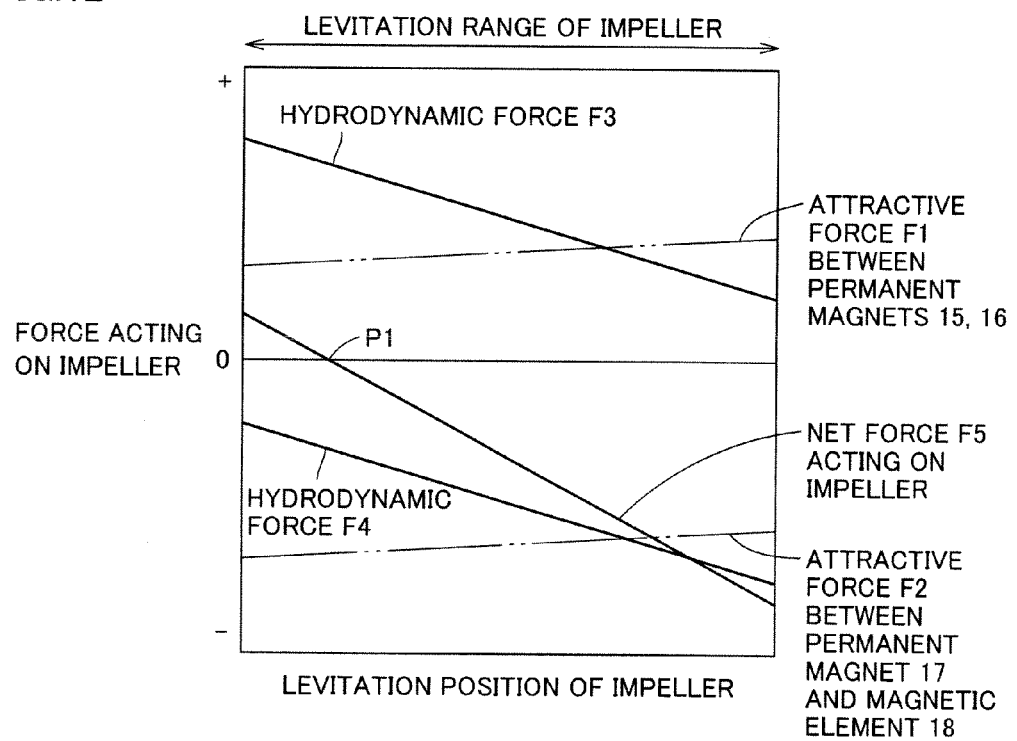
FIG. 12 is a diagram showing relation between a levitation position of the impeller and force acting on the impeller.

FIG. 12 is a diagram showing forces acting on impeller 10 when magnitude of a resultant force of an attractive force F1 between permanent magnets 15a, 15b and permanent magnets 16a, 16b (abbreviated as between permanent magnets 15 and 16 in FIG. 12) and an attractive force F2 between permanent magnet 17 and magnetic element 18 is adjusted to zero at a position P1 other than a central position of the movable range of impeller 10 in blood chamber 7. The rotation speed of impeller 10 is kept at a rated value.

Namely, it is assumed that attractive force F1 between permanent magnets 15a, 15b and permanent magnets 16a, 16b is set to be smaller than attractive force F2 between permanent magnet 17 and magnetic element 18 and a levitation position of impeller 10 where their resultant force becomes zero is on the dividing wall 6 side relative to the center of the movable range of the impeller. Grooves for hydrodynamic bearing 21, 22 have the same shape.

A horizontal axis of FIG. 12 represents a position of impeller 10 (the left side in the figure being the dividing wall 6 side) and a vertical axis represents forces acting on impeller 10. Force acting on impeller 10 toward the dividing wall 6 side is expressed as a negative acting force. As the forces acting on impeller 10, attractive force F1 between permanent magnets 15a, 15b and permanent magnets 16a, 16b, attractive force F2 between permanent magnet 17 and magnetic element 18, a hydrodynamic force F3 generated by grooves for hydrodynamic bearing 21, a hydrodynamic force F4 generated by grooves for hydrodynamic bearing 22, and "net force F5 acting on impeller," which is their resultant force, are illustrated.

As can be seen in FIG. 12, at a position where net force F5 acting on impeller 10 becomes zero, the levitation position of impeller 10 is significantly deviated from the central position of the movable range of impeller 10. As a result, a distance between rotating impeller 10 and dividing wall 6 becomes narrower, and impeller 10 comes in contact with dividing wall 6 even by the action of small disturbance force on impeller 10.

Figure 13:
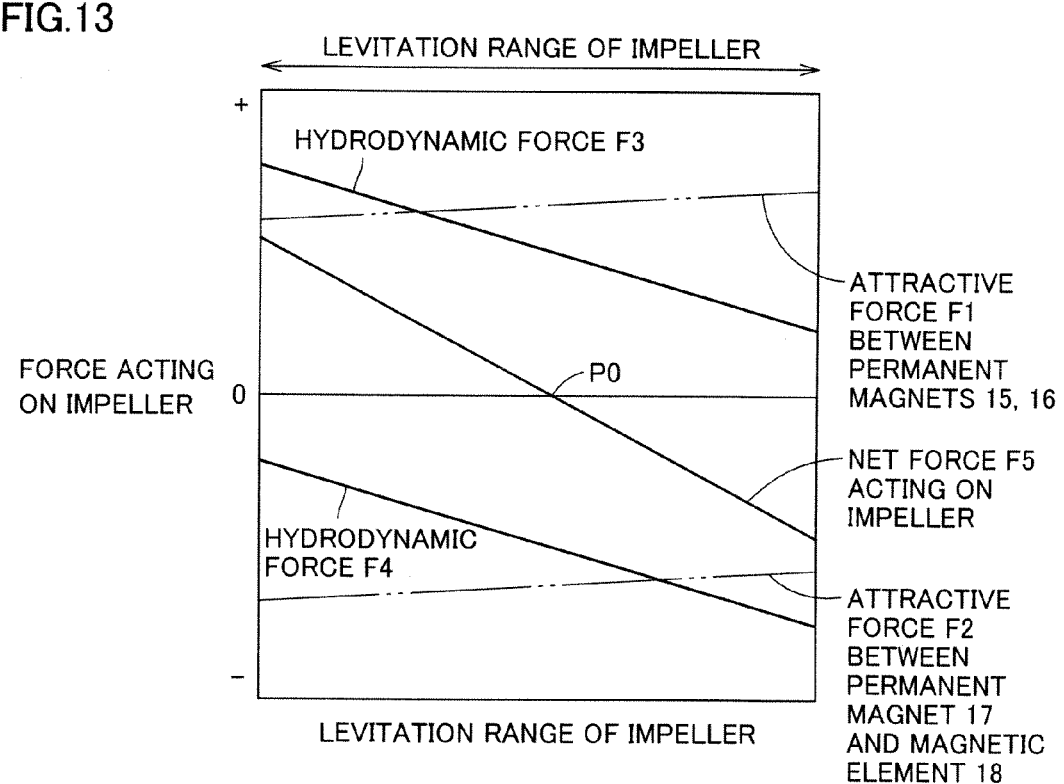
FIG. 13 is another diagram showing relation between a levitation position of the impeller and force acting on the impeller.

In contrast, FIG. 13 is a diagram showing forces acting on impeller 10 when magnitude of the resultant force of attractive force F1 between permanent magnets 15a, 15b and permanent magnets 16a, 16b and attractive force F2 between permanent magnet 17 and magnetic element 18 is adjusted to zero at a central position P0 of the movable range of impeller 10 in blood chamber 7. The rotation speed of impeller 10 is kept at the rated value also in this case.

Namely, attractive force F1 between permanent magnets 15a, 15b and permanent magnets 16a, 16b and attractive force F2 between permanent magnet 17 and magnetic element 18 are set to be substantially equal to each other. In addition, grooves for hydrodynamic bearing 21, 22 have the same shape. In this case, supporting rigidity with respect to the levitation position of impeller 10 becomes higher as compared with the case of FIG. 12. Since net force F5 acting on impeller 10 is zero at the center of the movable range, impeller 10 is levitated at the central position when disturbance force is not acting on impeller 10.

As such, a levitation position of impeller 10 is determined by balance among attractive force F1 between permanent magnets 15a, 15b and permanent magnets 16a, 16b, attractive force F2 between permanent magnet 17 and magnetic element 18, and hydrodynamic forces F3, F4 generated by grooves for hydrodynamic bearing 21, 22 during rotation of impeller 10. By making F1 and F2 substantially equal to each other and by forming grooves for hydrodynamic bearing 21, 22 in the same shape, impeller 10 can be levitated substantially in a central portion of blood chamber 7 during rotation of impeller 10. Since impeller 10 has such a shape that vanes are formed between two discs as shown in FIGS. 3 and 4, two surfaces facing the inner wall of housing 2 can be formed to have the same shape and the same dimensions. Therefore, it is possible to provide grooves for hydrodynamic bearing 21, 22 having a function to generate substantially the same hydrodynamic force on both sides of impeller 10.

In this case, impeller 10 is levitated at the central position of blood chamber 7 and thus held at a position farthest from the inner wall of housing 2. As a result, even if the levitation position of impeller 10 is changed due to application of disturbance force to levitated impeller 10, the possibility that impeller 10 is brought into contact with the inner wall of housing 2 is lowered, thus also lowering the possibility of occurrence of thrombus and hemolysis resulting from such contact.

While grooves for hydrodynamic bearing 21, 22 have the same shape in the examples shown in FIGS. 12 and 13, grooves for hydrodynamic bearing 21 may be different in shape and hydrodynamic force generating function from grooves for hydrodynamic bearing 22. For example, when disturbance acts on impeller 10 always in one direction due to hydrodynamic force or the like during pumping, performance of a groove for hydrodynamic bearing in the disturbance direction may be made higher than performance of the other groove for hydrodynamic bearing, thereby levitating and rotating impeller 10 at the central position of housing 2. As a result, the probability of contact between impeller 10 and housing 2 can be lowered, thereby attaining stable levitation performance of impeller 10.

Furthermore, when an absolute value of a negative axial supporting rigidity value of impeller 10 which is constituted of attractive force F1 between permanent magnets 15a, 15b and permanent magnets 16a, 16b and attractive force F2 between permanent magnet 17 and magnetic element 18 is expressed as Ka, an absolute value of a positive radial rigidity value is expressed as Kr, and an absolute value of a positive rigidity value obtained by two grooves for hydrodynamic bearing 21, 22 in a normal rotation speed range where impeller 10 rotates is expressed as Kg, it is preferable that relation of Kg>Ka+Kr be satisfied.

Specifically, when absolute value Ka of the negative axial rigidity value is 20000 N/m and absolute value Kr of the positive radial rigidity value is 10000 N/m, absolute value Kg of the positive rigidity value obtained by two grooves for hydrodynamic bearing 21, 22 in a rotation speed region where impeller 10 normally rotates is set to a value higher than 30000 N/m.

The axial supporting rigidity for impeller 10 is a value obtained by subtracting negative rigidity due to the attractive force between the magnetic elements and the like from rigidity resulting from the hydrodynamic force generated by grooves for hydrodynamic bearing 21, 22. Thus, by satisfying relation of Kg>Ka+Kr, the axial supporting rigidity for impeller 10 can be made higher than the radial supporting rigidity. With such setting, movement of impeller 10 can be suppressed more in the axial direction than in the radial direction when disturbance force acts on impeller 10, thereby avoiding mechanical contact between impeller 10 and housing 2 in a portion where grooves for hydrodynamic bearing 21 are formed.

In particular, since grooves for hydrodynamic bearing 21, 22 are provided as concave portions in planar surfaces as shown in FIGS. 3, 8 and 9, mechanical contact between housing 2 and impeller 10 in these portions during rotation of impeller 10 may result in damage to one or both of a surface of impeller 10 and a surface of the inner wall of housing 2 (projections and recesses in the surfaces), and blood passage through this portion may cause occurrence of thrombus and hemolysis. In order to prevent mechanical contact at grooves for hydrodynamic bearing 21, 22 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15a, 15b and permanent magnets 16a, 16b and attractive force F2 between permanent magnet 17 and magnetic element 18 is expressed as Kr (N/m), the mass of impeller 10 is expressed as m (kg), and the rotation speed of the impeller is expressed as ω (rad/s), it is preferable that relation of $\omega < (Kr/m)^{0.5}$ be satisfied.

Specifically, when the mass of impeller 10 is 0.03 kg and the radial rigidity value is 2000 N/m, the maximum rotation speed of impeller 10 is set to 258 rad/s (2465 rpm) or lower. Conversely, when the maximum rotation speed of impeller 10 is set to 366 rad/s (3500 rpm), the radial rigidity is set to 4018 N/m or higher.

It is further preferable to set the maximum rotation speed of impeller 10 to 80% or lower of this ω. Specifically, when the mass of impeller 10 is 0.03 kg and the radial rigidity value is 2000 N/m, the maximum rotation speed is set to 206.4 rad/s (1971 rpm) or lower. Conversely, when it is desired to set the maximum rotation speed of impeller 10 to 366 rad/s (3500 rpm), the radial rigidity value is set to 6279 N/m or higher. By thus setting the maximum rotation speed of impeller 10, contact between rotating impeller 10 and housing 2 can be suppressed.

It is also preferable to check that impeller 10 is in contact with dividing wall 6 before activating impeller 10 to rotate, and to activate impeller 10 to rotate.

In other words, when impeller 10 is not rotating, noncontact supporting by grooves for hydrodynamic bearing 21, 22 is not achieved, and furthermore, impeller 10 is in contact with housing 2 at a high surface pressure owing to attractive force F1 between permanent magnets 15a, 15b and permanent magnets 16a, 16b and attractive force F2 between permanent magnet 17 and magnetic element 18. Activation torque is smaller when impeller 10 is rotated by magnetic interaction between coils 20 and magnetic element 18 in motor chamber 8 and permanent magnet 17 in impeller 10 as with pump unit 1 than when the impeller as shown in FIG. 3 of PTL 2 is driven to rotate by magnetic coupling between the permanent magnets. Therefore, it is difficult to smoothly activate impeller 10 to rotate.

Permanent magnet 17 in impeller 10 is, however, closer to magnetic element 18 in motor chamber 8 when shroud 12 of impeller 10 is in contact with dividing wall 6 than when shroud 11 of impeller 10 is in contact with the inner wall of blood chamber 7. Therefore, rotational torque during activation of impeller 10 can be increased and impeller 10 can be smoothly activated to rotate.

As described above, however, when impeller 10 is rotating, attractive force F1 between permanent magnets 15a, 15b and permanent magnets 16a, 16b and attractive force F2 between permanent magnet 17 and magnetic element 18 are set to be balanced with each other around a center of the movable range of impeller 10. Therefore, when impeller 10 stops, impeller 10 is not necessarily in contact with dividing wall 6.

Accordingly, this centrifugal blood pump apparatus is provided with means for moving impeller 10 toward the dividing wall 6 side before activating impeller 10 to rotate. Specifically, a current is fed to the plurality of coils 20 such that attractive force F2 between permanent magnet 17 and magnetic element 18 becomes large, and impeller 10 is moved toward the dividing wall 6 side.

Figure 14:
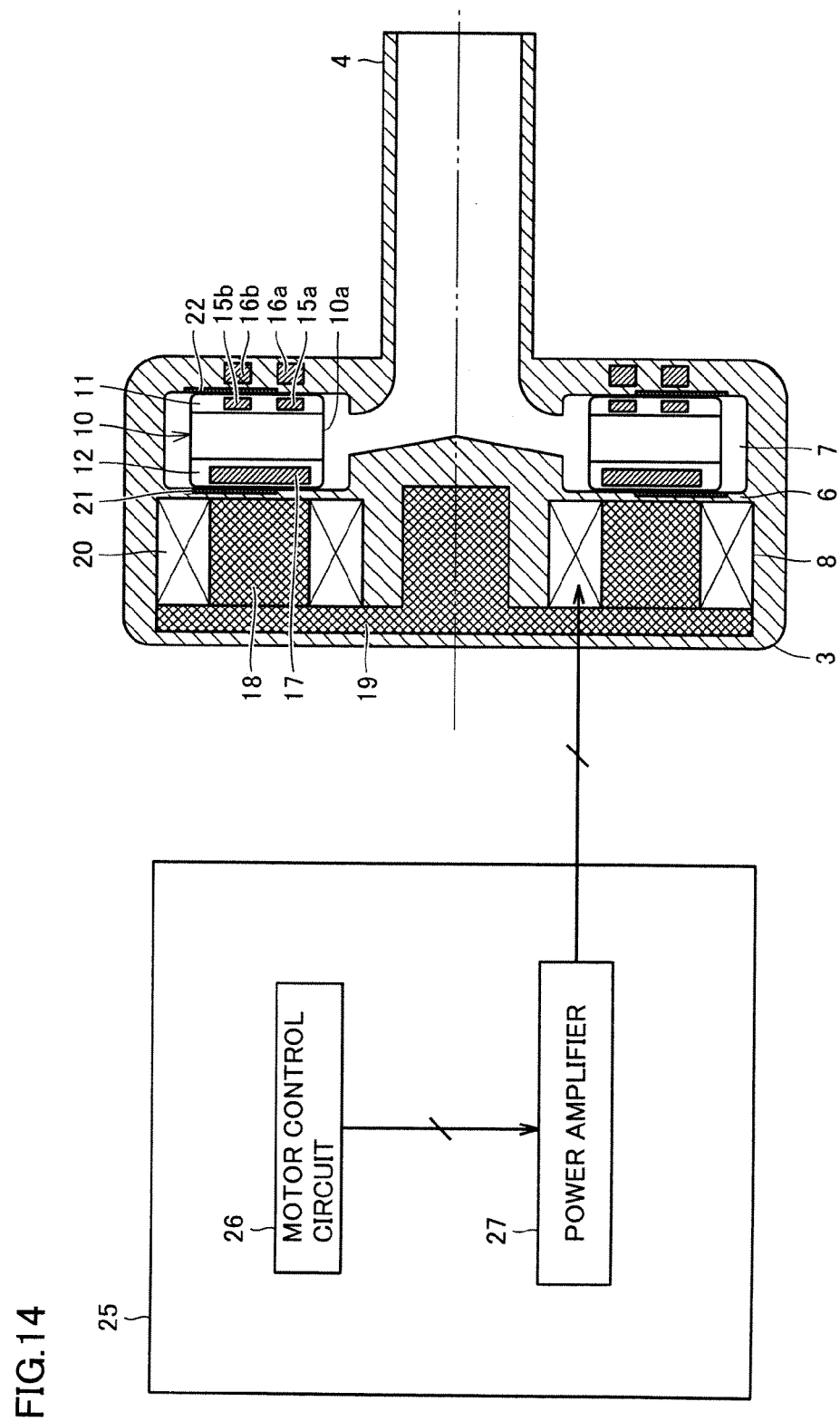
FIG. 14 is a block diagram showing a configuration of a controller for controlling the pump unit shown in FIGS. 1 to 10.

FIG. 14 is a block diagram showing a configuration of a controller 25 for controlling pump unit 1. In FIG. 14, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26 and generates three-phase voltages VU, VV and VW shown in FIG. 9. Three-phase voltages VU, VV and VW are applied to first to third coils 20 described with reference to FIG. 11, respectively. As a result, during normal operation, impeller 10 rotates at a prescribed rotation speed at the central position of the movable range.

Figure 15:
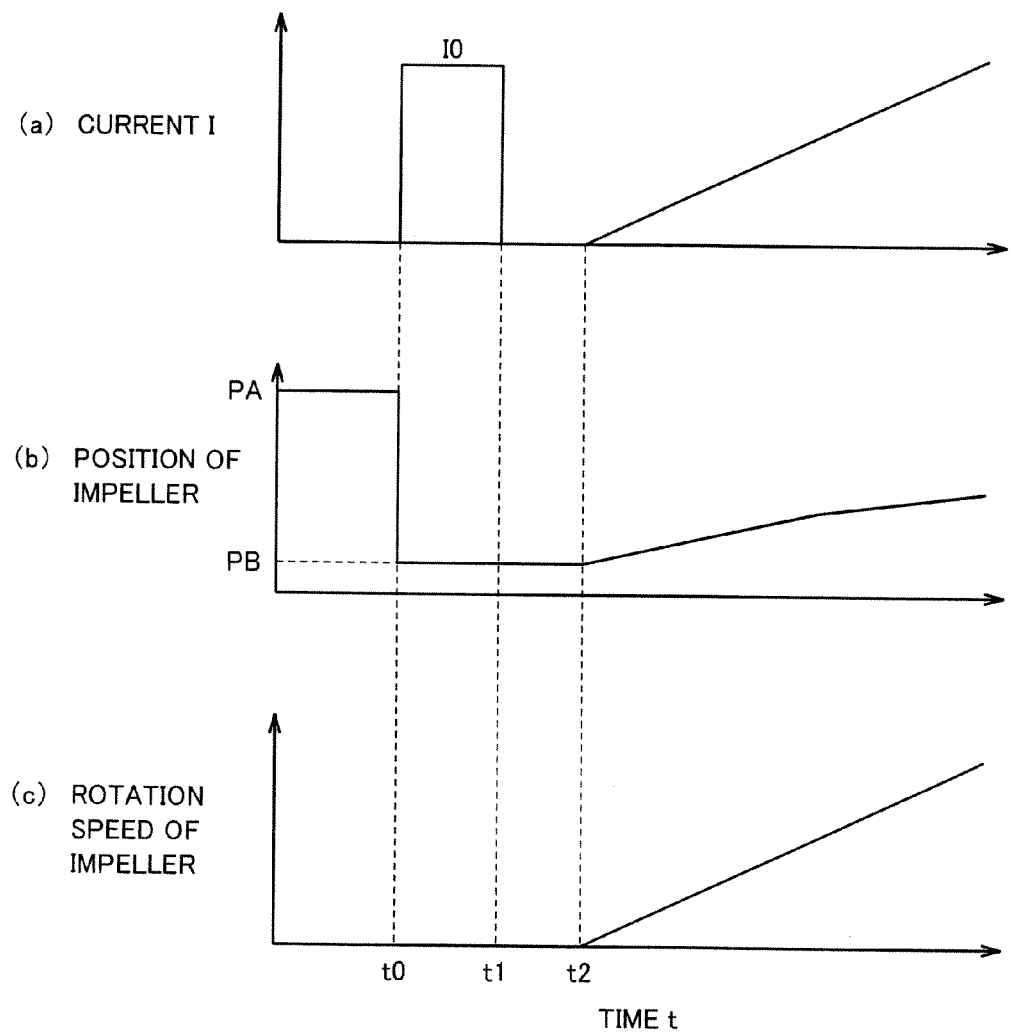
FIG. 15 is a time chart showing the operation of the controller shown in FIG. 14.

FIGS. 15(a) to (c) are time charts showing temporal changes in a coil current I when activating impeller 10 to rotate, the position of impeller 10, and the rotation speed of impeller 10. Referring to FIGS. 15(a) to (c), in an initial state, shroud 11 of impeller 10 is in contact with the inner wall of blood chamber 7 due to the attractive force between permanent magnets 15a, 15b and permanent magnets 16a, 16b, and impeller 10 is in a position PA. Since it is difficult to rotate impeller 10 in this state, impeller 10 is moved to a position PB where shroud 12 of impeller 10 is in contact with dividing wall 6.

At time t0, voltages VU, VV and VW of any one of the six patterns (0 to 60 degrees, 60 to 120 degrees, . . . , 300 to 360 degrees) shown in FIG. 11 are applied to first to third coils 20, respectively, and a predetermined current I0 is fed through coils 20. When current I0 is fed through coils 20, attractive force F2 between permanent magnet 17 and magnetic element 18 becomes higher than attractive force F1 between permanent magnets 15a, 15b and permanent magnets 16a, 16b, so that impeller 10 moves to position PB on the dividing wall 6 side with little rotation, causing shroud 12 of impeller 10 to be in contact with dividing wall 6. When impeller 10 moves to position PB, current I0 is cut off (time t1).

The reason for moving impeller 10 without rotating impeller 10 is that movement of rotating impeller 10 to position PB on the dividing wall 6 side is blocked by the hydrodynamic bearing effect of grooves for hydrodynamic bearing 21. In addition, it is preferable to provide a sensor for detecting a position of impeller 10 in blood chamber 7, and check to see that impeller 10 is in contact with dividing wall 6 before cutting off current I0.

Then, three-phase voltages VU, VV and VW are applied to first to third coils 20 described with reference to FIGS. 10 and 11, respectively, and coil current I is gradually increased to a predetermined rated value. Here, impeller 10 is in contact with dividing wall 6, and thus smoothly rotates. With the increase in coil current I, impeller 10 moves from position PB on the dividing wall 6 side to the central position of the movable range.

When voltages VU, VV and VW of the six patterns (0 to 60 degrees, 60 to 120 degrees, . . . , 300 to 360 degrees) are applied to first to third coils 20 during activation, respectively, a pattern where the attractive force between permanent magnet 17 and magnetic element 18 becomes maximum varies with positional relation between permanent magnet 17 and magnetic element 18. Thus, instead of applying only voltages VU, VV and VW of the constant patterns to first to third coils 20 during activation, respectively, voltages VU, VV and VW of the six patterns may be successively applied to first to third coils 20 for a predetermined time. In this case, impeller 10 slightly rotates (strictly speaking, equal to or less than a quarter rotation, i.e., rotates equal to or smaller than 360 degrees in electrical angle), and moves to position PB on the dividing wall 6 side.

When voltages VU, VV and VW of the six patterns are applied, a current does not flow through one of first to third coils 20, six of nine magnetic elements 18 become the N-pole or the S-pole, and three remaining magnetic elements 18 do not generate a magnetic polarity. Thus, voltages that cause a current to flow through all of first to third coils 20 and each of nine magnetic elements 18 to become the N-pole or the S-pole may be applied to first to third coils 20, to increase the attractive force between permanent magnet 17 and magnetic element 18.

In this first embodiment, the attractive force between permanent magnets 15a, 15b and permanent magnets 16a, 16b on the opening 7a side of the sidewall of blood chamber 7 is set to be smaller than the attractive force between permanent magnets 15a, 15b and permanent magnets 16a, 16b on the opposite side of opening 7a, and thus, impeller 10 can become parallel to dividing wall 6 during rotation. Therefore, contact of impeller 10 with the inner wall of blood chamber 7 can be prevented, and the impeller can be levitated in a stable manner, and occurrence of hemolysis and thrombus can be prevented.

Figure 16:
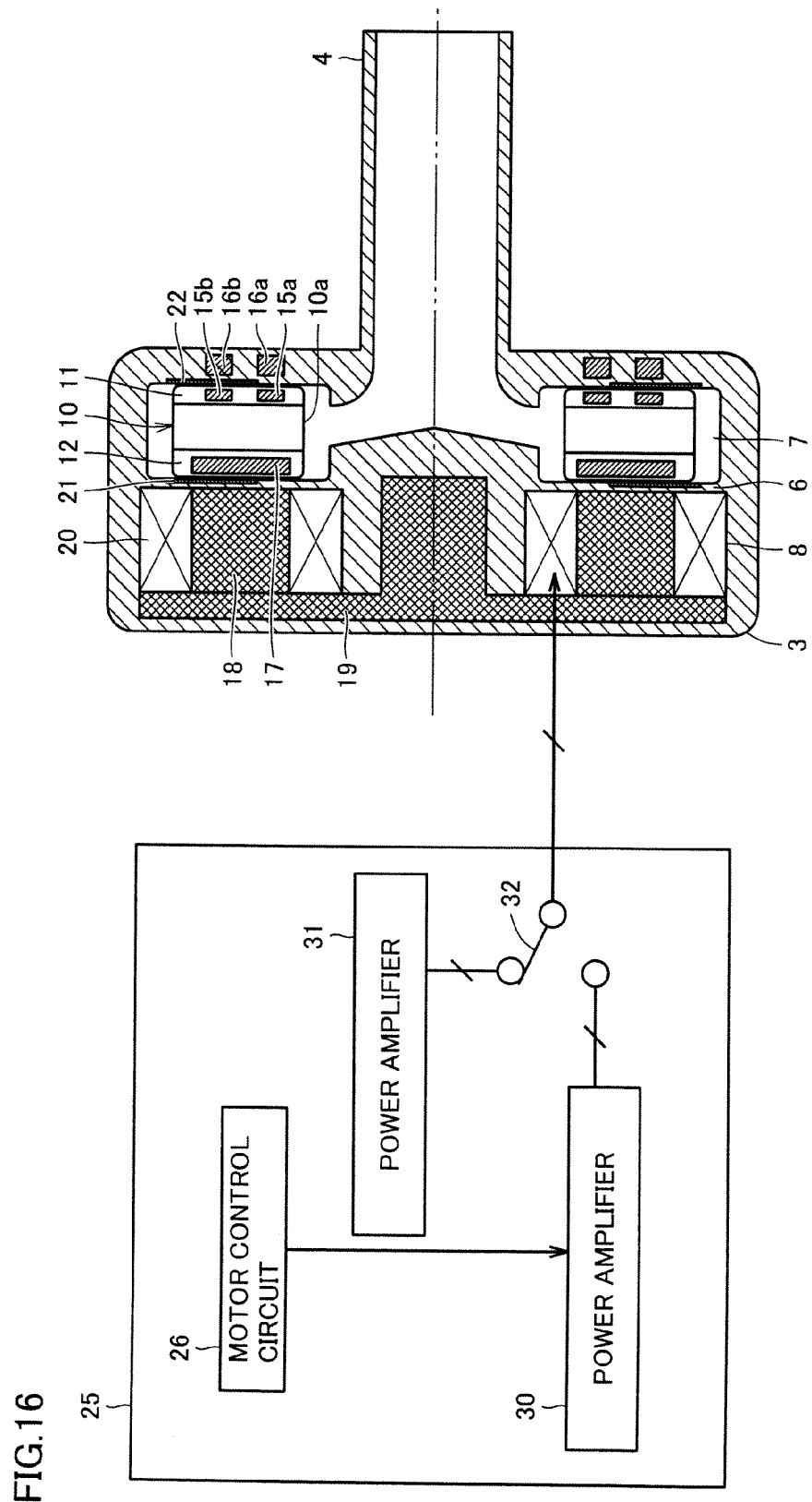
FIG. 16 is a block diagram showing a modification of this first embodiment.

Various modifications of the first embodiment will be described hereinafter. In a modification of FIG. 16, a power source is switched between during activation of impeller 10 for rotation and a subsequent time period. That is, referring to FIG. 16, in this modification, power amplifier 27 in FIG. 14 is replaced with power amplifiers 30, 31 and a switch 32. Between time t0 and t1 in FIG. 15, an output signal from motor control circuit 26 is provided to power amplifier 30, and an output voltage from power amplifier 30 is applied to coils 20 via switch 32, causing current I0 to flow through coils 20. After time t2, an output signal from motor control circuit 26 is provided to power amplifier 31, and an output voltage from power amplifier 31 is applied to coils 20 via switch 32, causing a current to flow through coils 20.

Figure 17:
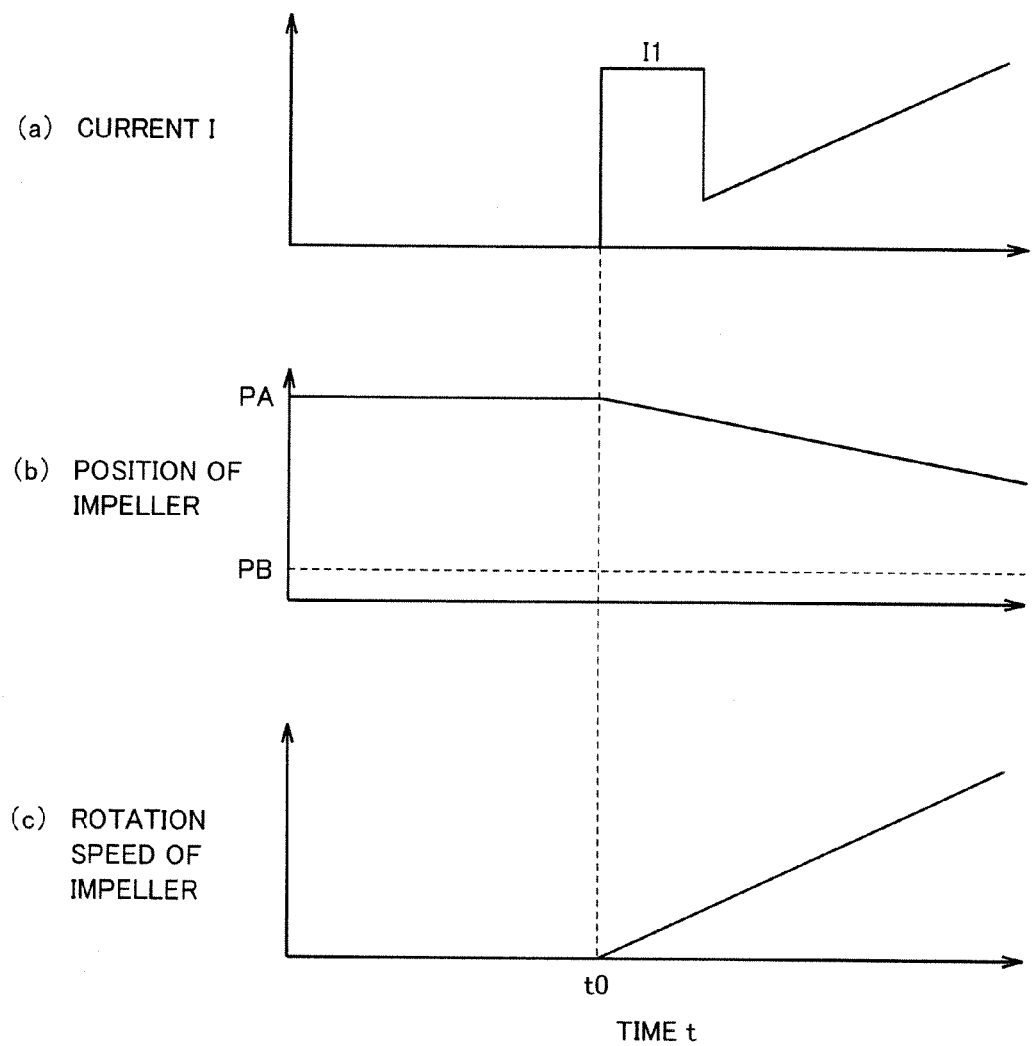
FIG. 17 is a time chart showing another modification of this first embodiment.

FIGS. 17(a) to (c) are time charts showing another modification of the first embodiment. Referring to FIGS. 17(a) to (c), in an initial state, shroud 11 of impeller 10 is in contact with the inner wall of blood chamber 7, and impeller 10 is in position PA. At time t0, a predetermined current I1 is fed through coils 20. That is, motor control circuit 26 generates three-phase control signals in the power distribution system shifted by 120 degrees, for example. Power amplifier 27 amplifies the three-phase control signals from motor control circuit 26, and generates three-phase voltages VU, VV and VW shown in FIG. 11. Three-phase voltages VU, VV and VW are applied to first to third coils 20 described with reference to FIG. 10, respectively.

Accordingly, a rotating magnetic field is applied to impeller 10 by current I1. Current I1 is larger than current I0 in FIG. 15, and can activate impeller 10 to rotate even when shroud 11 of impeller 10 is in contact with the inner wall of blood chamber 7. After activation for rotation is confirmed, coil current I is reduced, and gradually increased to the predetermined rated value. In this manner, even when impeller 10 is on the position PA side, an excessive current may be fed through coils 20 only when activating impeller 10 to rotate.

In addition, a diamond-like carbon (DLC) coating may be formed on at least one of the surface of the inner wall of blood chamber 7 and the surface of dividing wall 6, and the surface of impeller 10. As a result, frictional force between impeller 10, and the inner wall of blood chamber 7 and dividing wall 6 can be reduced to smoothly activate the impeller to rotate. A fluorine-based resin coating, a paraxylylene-based resin coating or the like may be formed instead of the diamond-like carbon coating.

Figure 18:
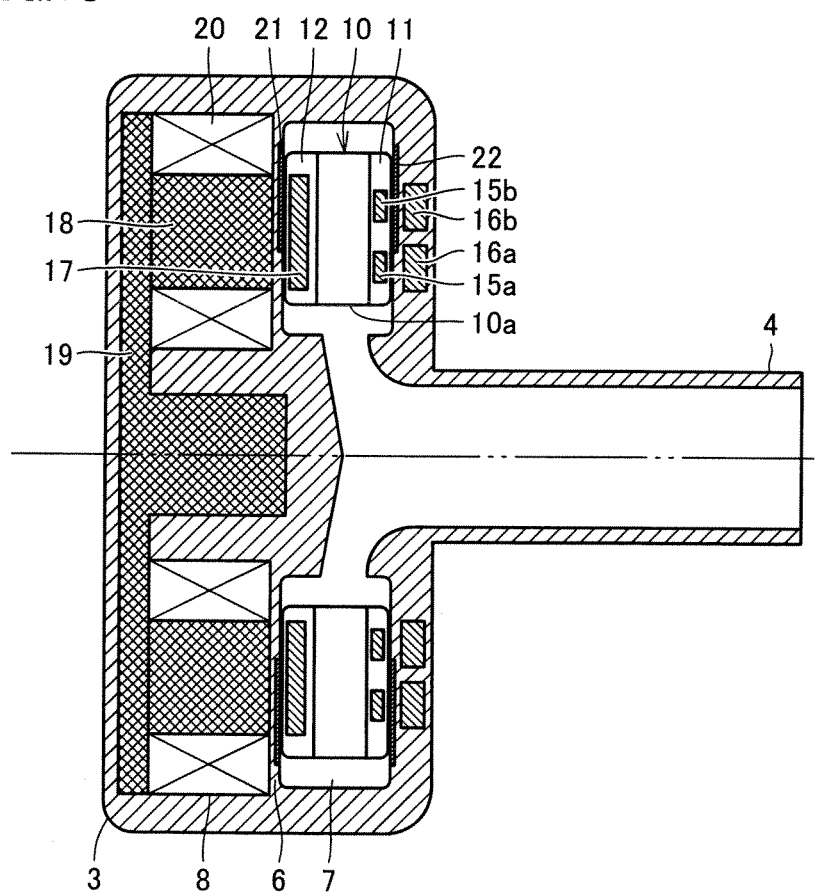
FIG. 18 is a cross-sectional view showing yet another modification of the first embodiment.

When the rigidity due to the hydrodynamic forces by grooves for hydrodynamic bearing 21, 22 becomes higher than the negative axial rigidity value of impeller 10 which is constituted of attractive force F1 between permanent magnets 15a, 15b and permanent magnets 16a, 16b and attractive force F2 between permanent magnet 17 and magnetic element 18, impeller 10 and housing 2 are not in contact with each other. It is thus preferable to minimize this negative rigidity value. In order to keep the negative rigidity value low, it is preferable that the opposing surfaces of permanent magnets 15a and 16a are different in size and the opposing surfaces of permanent magnets 15b and 16b are different in size. For example, as shown in FIG. 18, by making the size of permanent magnets 15a, 15b smaller than that of permanent magnets 16a, 16b, respectively, a rate of change in attractive force that varies with a distance between the magnets, namely, the negative rigidity can be minimized, thereby preventing reduction in supporting rigidity for the impeller.

Figure 19:
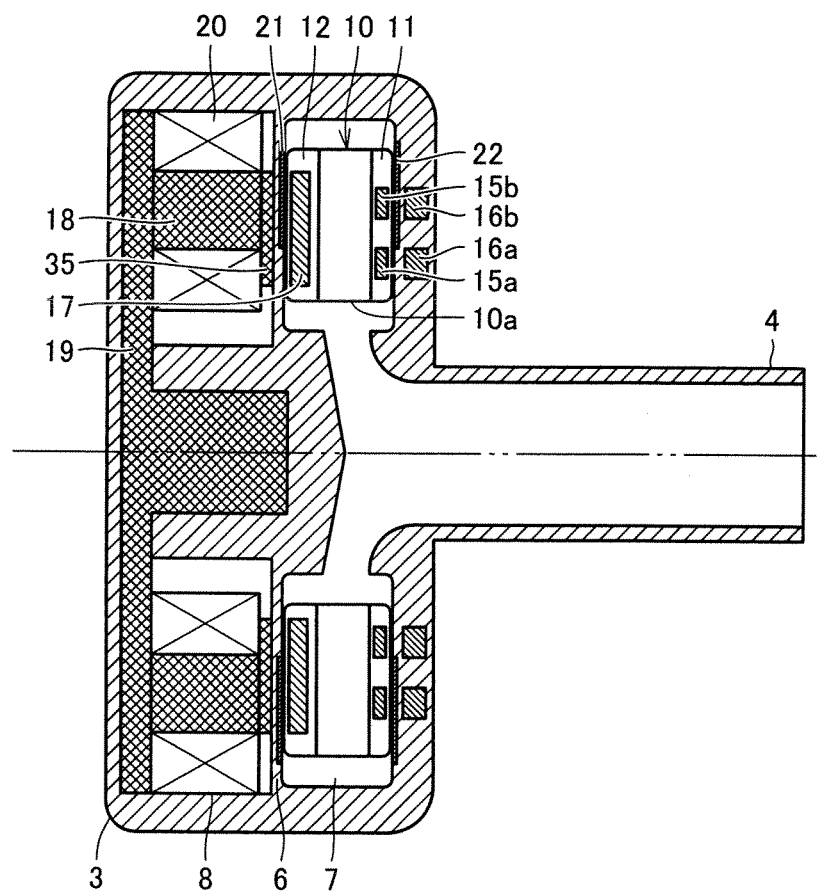
FIG. 19 is a cross-sectional view showing yet another modification of the first embodiment.

FIG. 19 is a cross-sectional view showing yet another modification of this first embodiment, which is compared to FIG. 3. Referring to FIG. 19, in this modification, a magnetic element 35 is provided on a tip surface of each magnetic element 18 facing permanent magnet 17. A surface of magnetic element 35 facing permanent magnet 17 has an area larger than an area of the tip surface of magnetic element 18. In this modification, attractive force of magnetic elements 18 and 35 on permanent magnet 17 can be increased, thus increasing energy efficiency when impeller 10 is driven to rotate.

Figure 20:
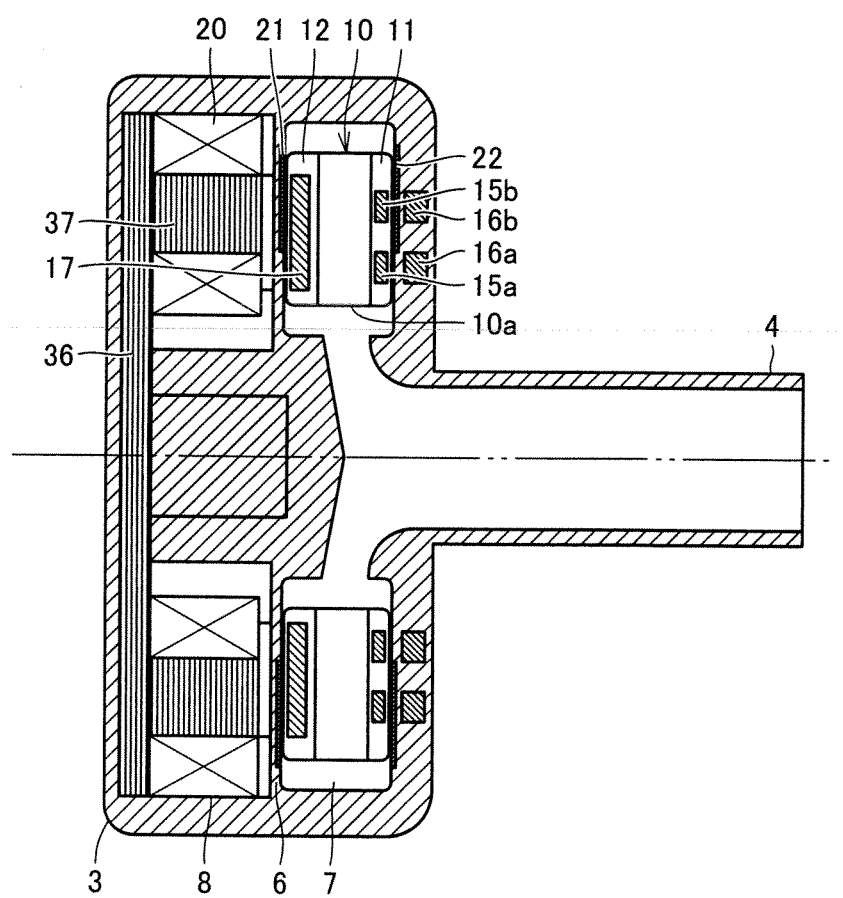
FIG. 20 is a cross-sectional view showing yet another modification of the first embodiment.

FIG. 20 is a cross-sectional view showing yet another modification of this first embodiment, which is compared to FIG. 3. Referring to FIG. 20, in this modification, yoke 19 is replaced with a yoke 36 and magnetic element 18 is replaced with a magnetic element 37. Yoke 36 and magnetic element 37 each include a plurality of steel plates stacked in a length direction of a rotation axis of impeller 10. In this modification, eddy current loss that occurs in yoke 36 and magnetic element 37 can be reduced, thus increasing energy efficiency when impeller 10 is driven to rotate.

Figure 21:
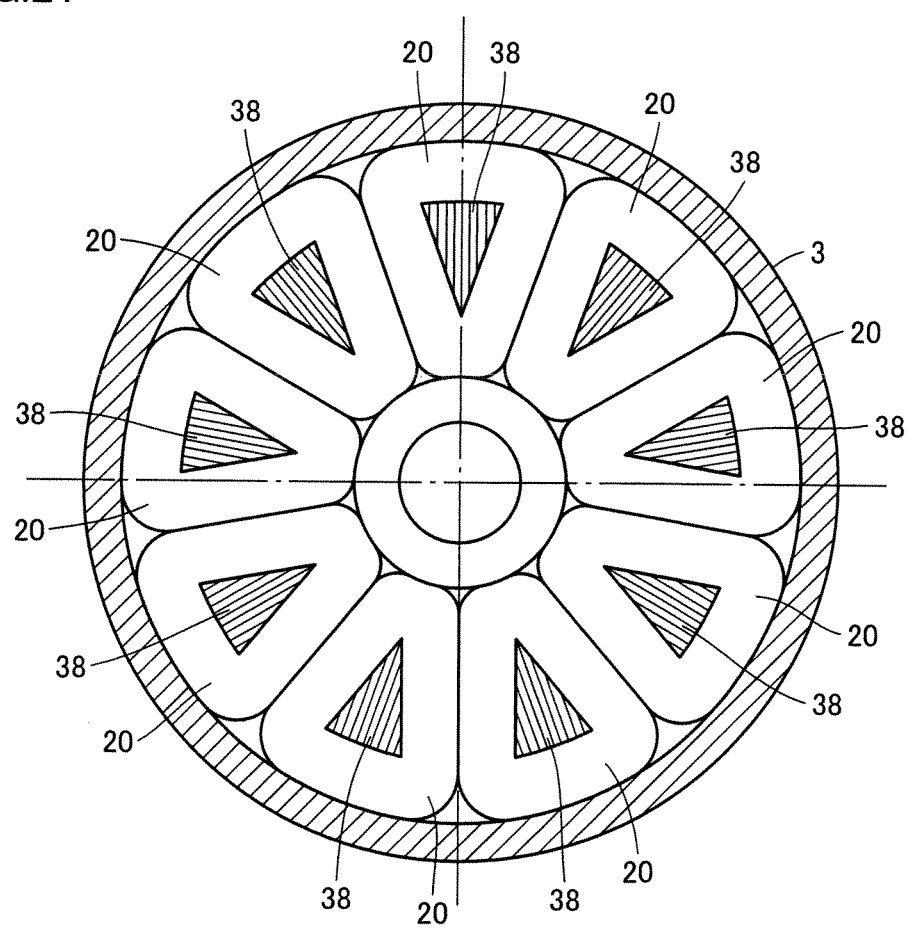
FIG. 21 is a cross-sectional view showing yet another modification of the first embodiment.
Figure 22:
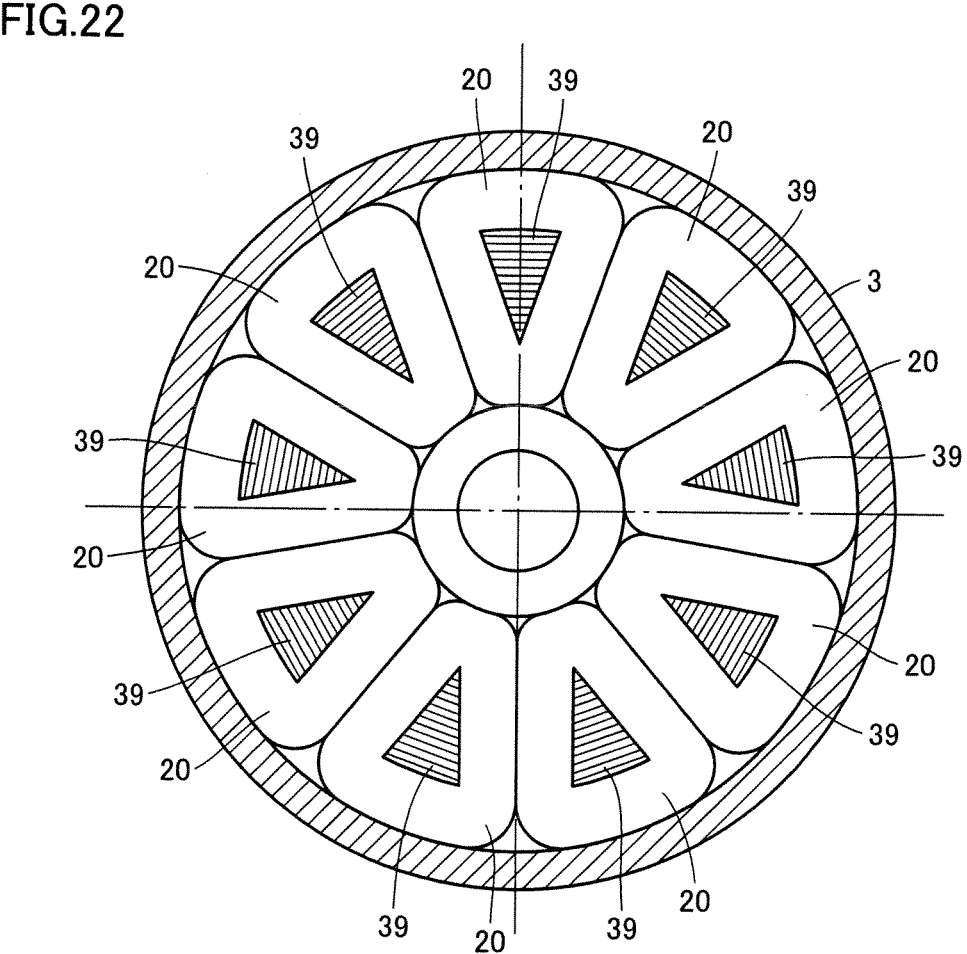
FIG. 22 is a cross-sectional view showing yet another modification of the first embodiment.

Alternatively, as shown in FIG. 21, magnetic element 37 may be replaced with a magnetic element 38 including a plurality of steel plates stacked in a rotation direction of impeller 10. Alternatively, as shown in FIG. 22, magnetic element 37 may be replaced with a magnetic element 39 including a plurality of steel plates stacked in a radial direction of impeller 10. The same effect as in the modification in FIG. 20 can be obtained also in these cases.

Alternatively, each of yoke 19 and magnetic element 18 in FIG. 3 may be made of powders of pure iron, soft iron or ferrosilicon. In this case, iron loss in yoke 19 and magnetic element 18 can be reduced, thus increasing energy efficiency when impeller 10 is driven to rotate.

Figure 23:
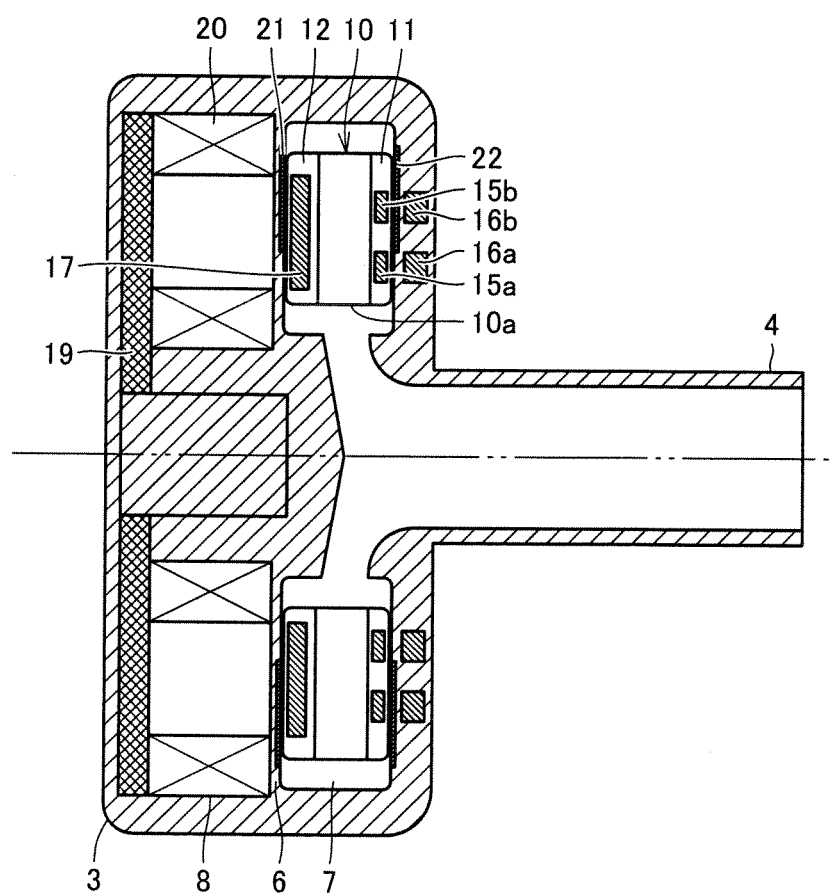
FIG. 23 is a cross-sectional view showing yet another modification of the first embodiment.

FIG. 23 is a cross-sectional view showing yet another modification of this first embodiment, which is compared to FIG. 3. Referring to FIG. 23, in this modification, magnetic element 18 has been removed. In this modification, magnitude of a resultant force of attractive force F1 between permanent magnets 15a, 15b and permanent magnets 16a, 16b and attractive force F2 between permanent magnet 17 and yoke 19 is adjusted to zero at central position P0 in the movable range of impeller 10 in blood chamber 7. The same effect as in the first embodiment can be obtained also in this modification.

Figure 24:
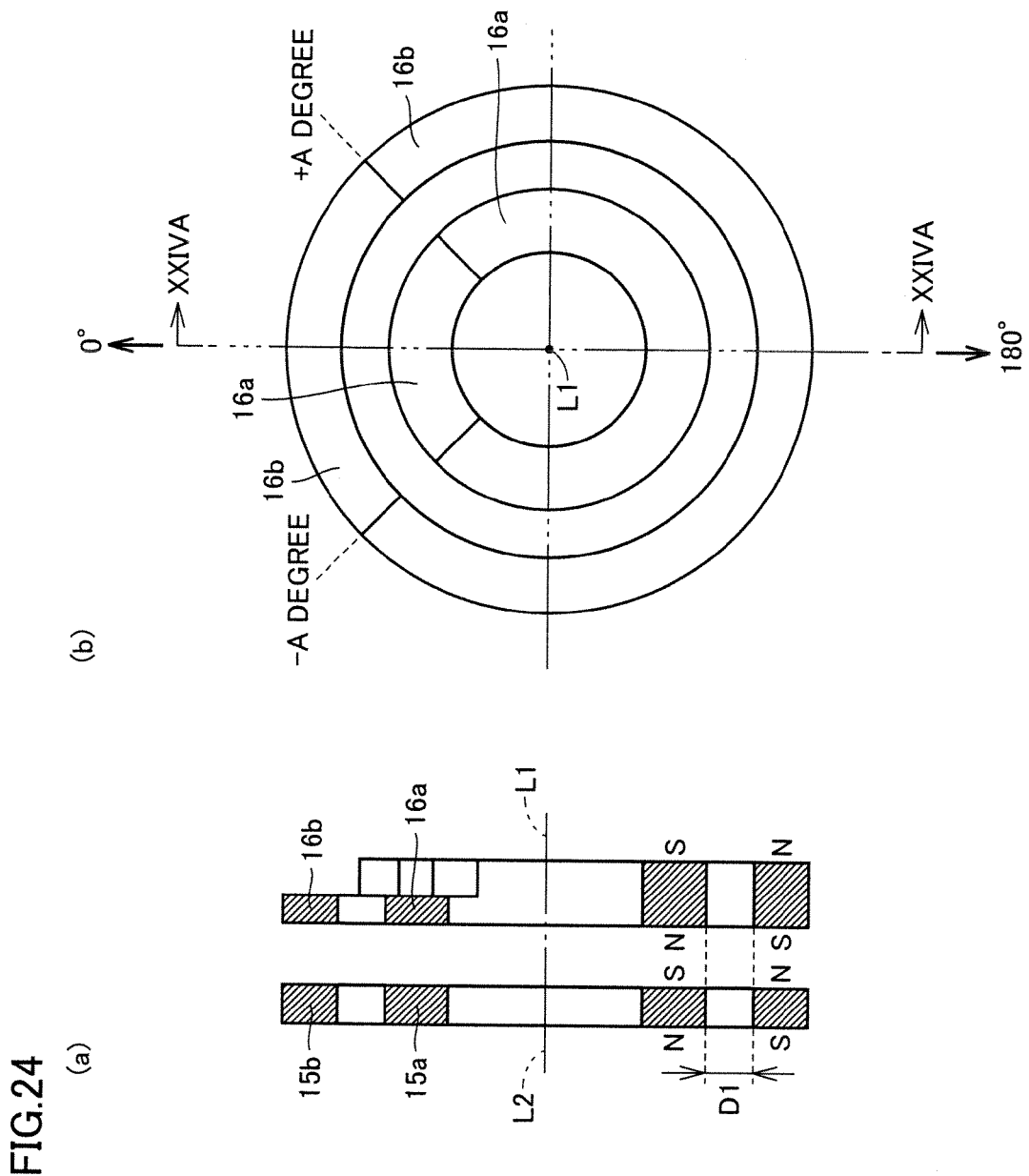
FIG. 24 is a diagram showing yet another modification of the first embodiment.

FIGS. 24(a) and (b) are diagrams showing yet another modification of this first embodiment, which are compared to FIGS. 7(a) and (b). FIG. 24(a) is a cross-sectional view along the line XXIVA-XXIVA in FIG. 24(b). In this modification, the N pole of permanent magnet 15a and the N pole of permanent magnet 15b are provided in directions opposite to each other, and the N pole of permanent magnet 16a and the N pole of permanent magnet 16b are provided in directions opposite to each other. The S pole of permanent magnet 15a faces the N pole of permanent magnet 16a and the N pole of permanent magnet 15b faces the S pole of permanent magnet 16b. The same effect as in the first embodiment can be obtained also in this modification.

Figure 25:
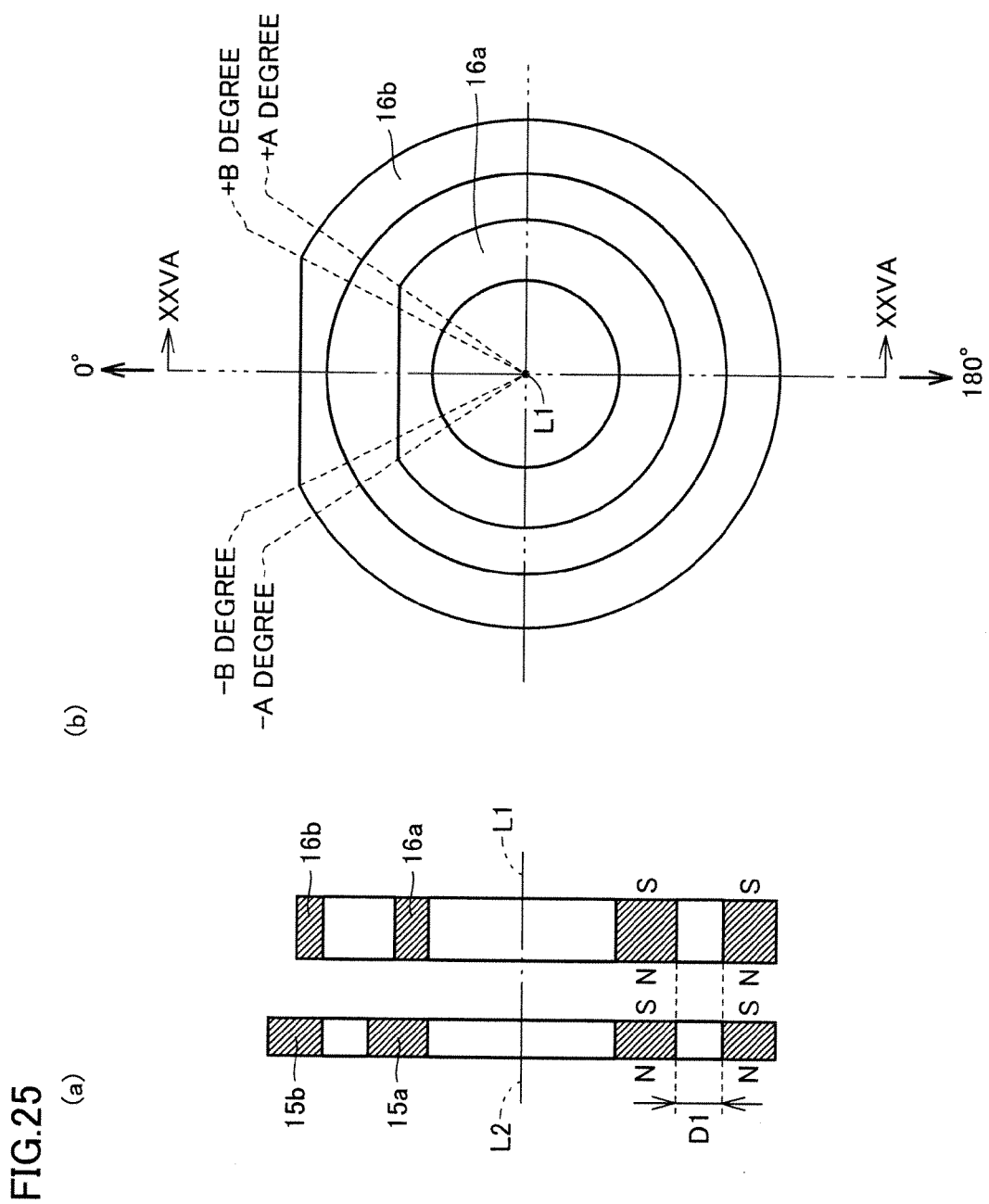
FIG. 25 is a diagram showing yet another modification of the first embodiment.

FIGS. 25(a) and (b) are diagrams showing a modification of the first embodiment, which are compared to FIGS. 7(a) and (b). FIG. 25(a) is a cross-sectional view along the line XXVA-XXVA in FIG. 25(b). Referring to FIGS. 25(a) and (b), in this modification, within the range of 0 degree±A degree when viewed from the centers of permanent magnets 16a and 16b, an end of annular permanent magnet 16a on the opening 7a side is removed by a plane parallel to centerline L1. In addition, within the range of 0 degree±B degree when viewed from the centers of permanent magnets 16a and 16b, an end of annular permanent magnet 16b on the opening 7a side is removed by a plane parallel to centerline L1. Each of the A degree and the B degree is a prescribed angle that is larger than 0 degree. Therefore, a facing area (i.e., attractive force) of permanent magnets 15a, 15b and permanent magnets 16a, 16b on the opening 7a side is smaller than a facing area (i.e., attractive force) of permanent magnets 15a, 15b and permanent magnets 16a, 16b on the opposite side of opening 7a. The same effect as in the first embodiment can be obtained also in this modification.

Figure 26:
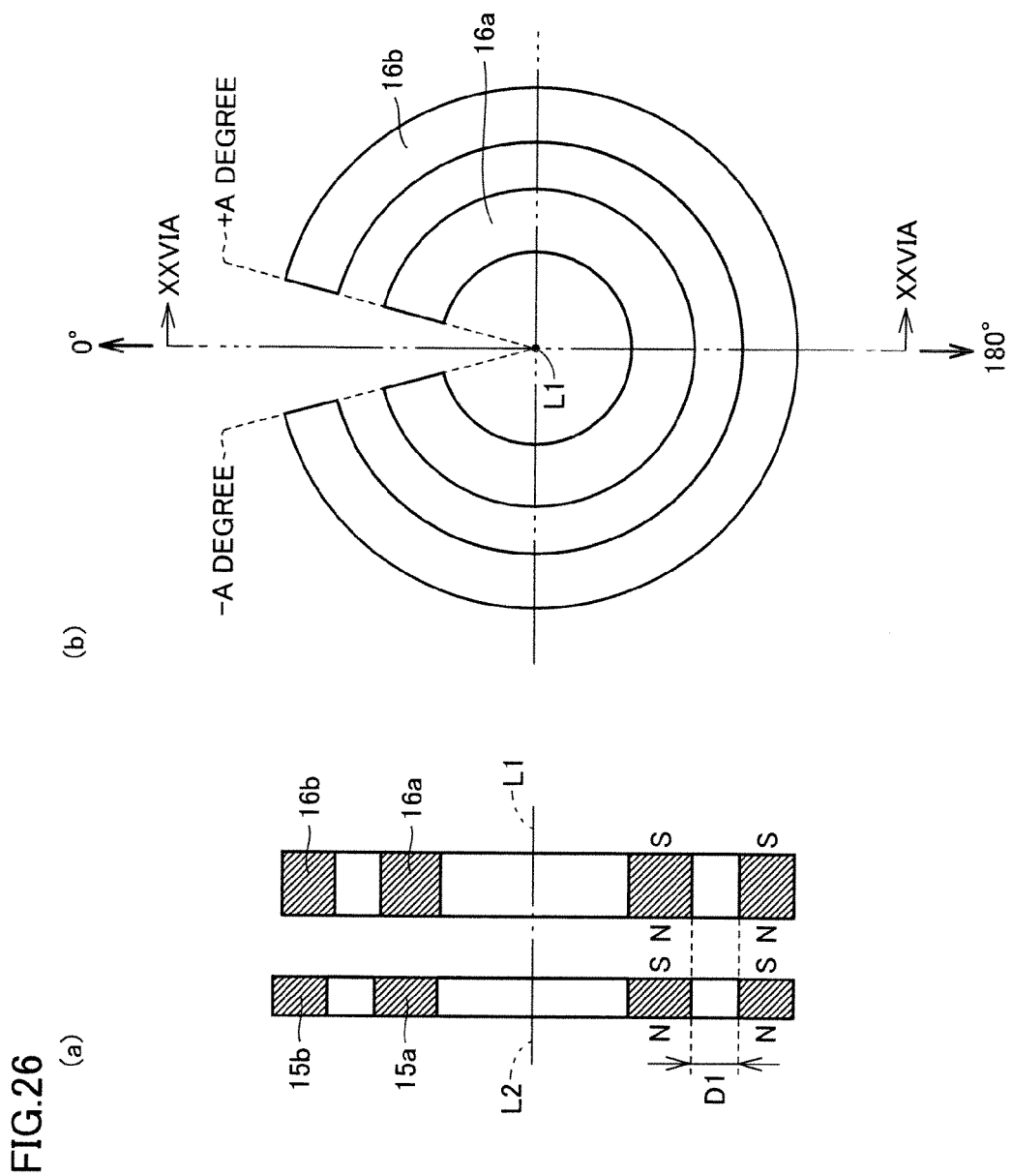
FIG. 26 is a diagram showing yet another modification of the first embodiment.

FIGS. 26(a) and (b) are diagrams showing another modification of the first embodiment, which are compared to FIGS. 7(a) and (b). FIG. 26(a) is a cross-sectional view along the line XXVIA-XXVIA in FIG. 26(b). Referring to FIGS.

26(a) and (b), in this modification, within the range of 0 degree±A degree when viewed from the centers of permanent magnets 16a and 16b, a sector-shaped portion of annular permanent magnets 16a and 16b is removed. The A degree is a prescribed angle that is larger than 0 degree and smaller than 180 degrees, and is preferably 60 degrees. Therefore, a facing area (i.e., attractive force) of permanent magnets 15a, 15b and permanent magnets 16a, 16b on the opening 7a side is smaller than a facing area (i.e., attractive force) of permanent magnets 15a, 15b and permanent magnets 16a, 16b on the opposite side of opening 7a. The same effect as in the first embodiment can be obtained also in this modification.

Figure 27:
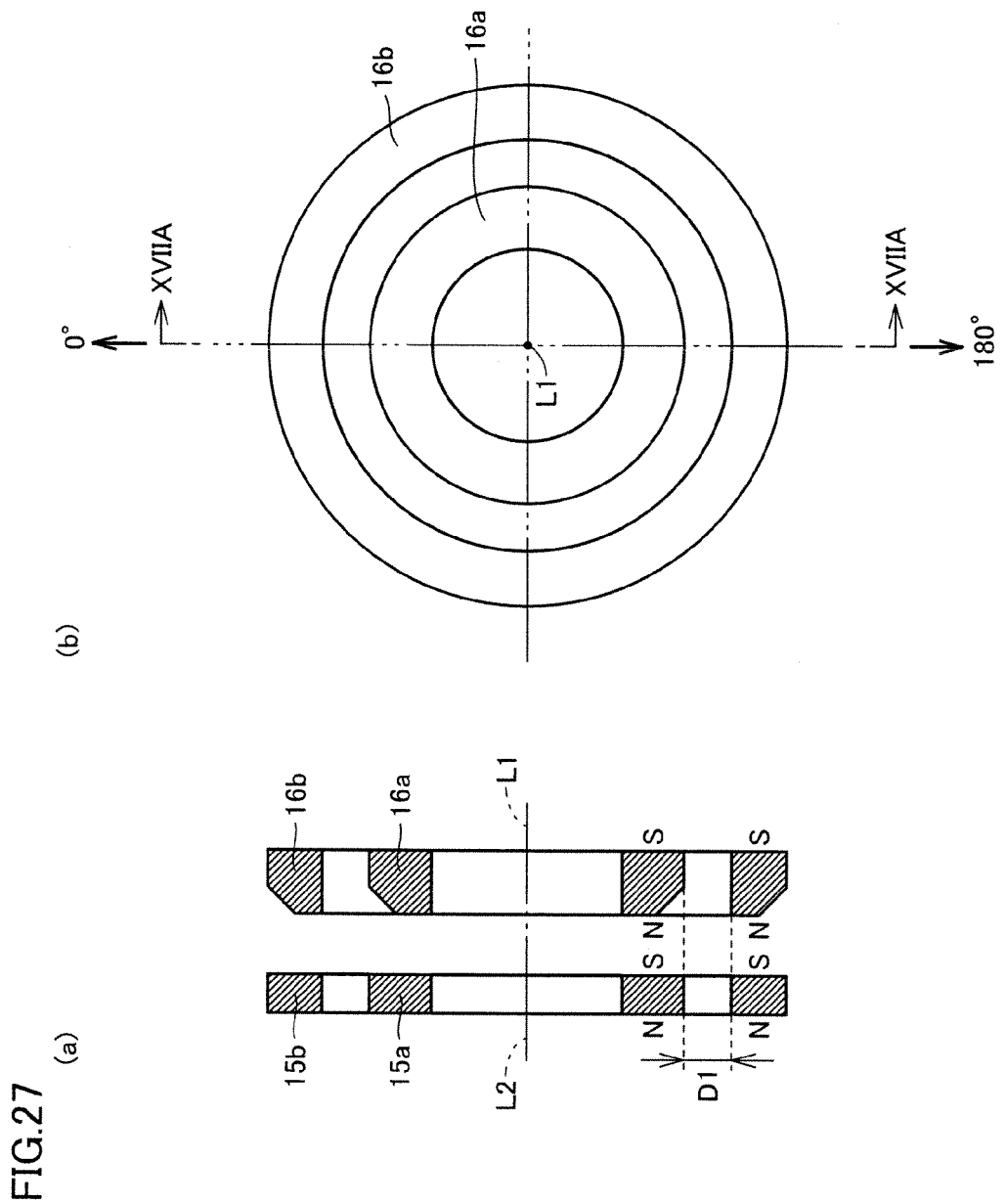
FIG. 27 is a diagram showing yet another modification of the first embodiment.

FIGS. 27(a) and (b) are diagrams showing yet another modification of the first embodiment, which are compared to FIGS. 7(a) and (b). FIG. 27(a) is a cross-sectional view along the line XXVIIA-XXVIIA in FIG. 27(b). Referring to FIGS. 27(a) and (b), in this modification, the entire outer circumferences of annular permanent magnets 16a and 16b are chamfered. Only a surface of permanent magnets 16a and 16b facing permanent magnets 15a and 15b may be chamfered, or only a surface opposite to the surface facing permanent magnets 15a and 15b may be chamfered, or both surfaces of permanent magnets 16a and 16b may be chamfered. A size of chamfering is not particularly limited, either.

Figure 28:
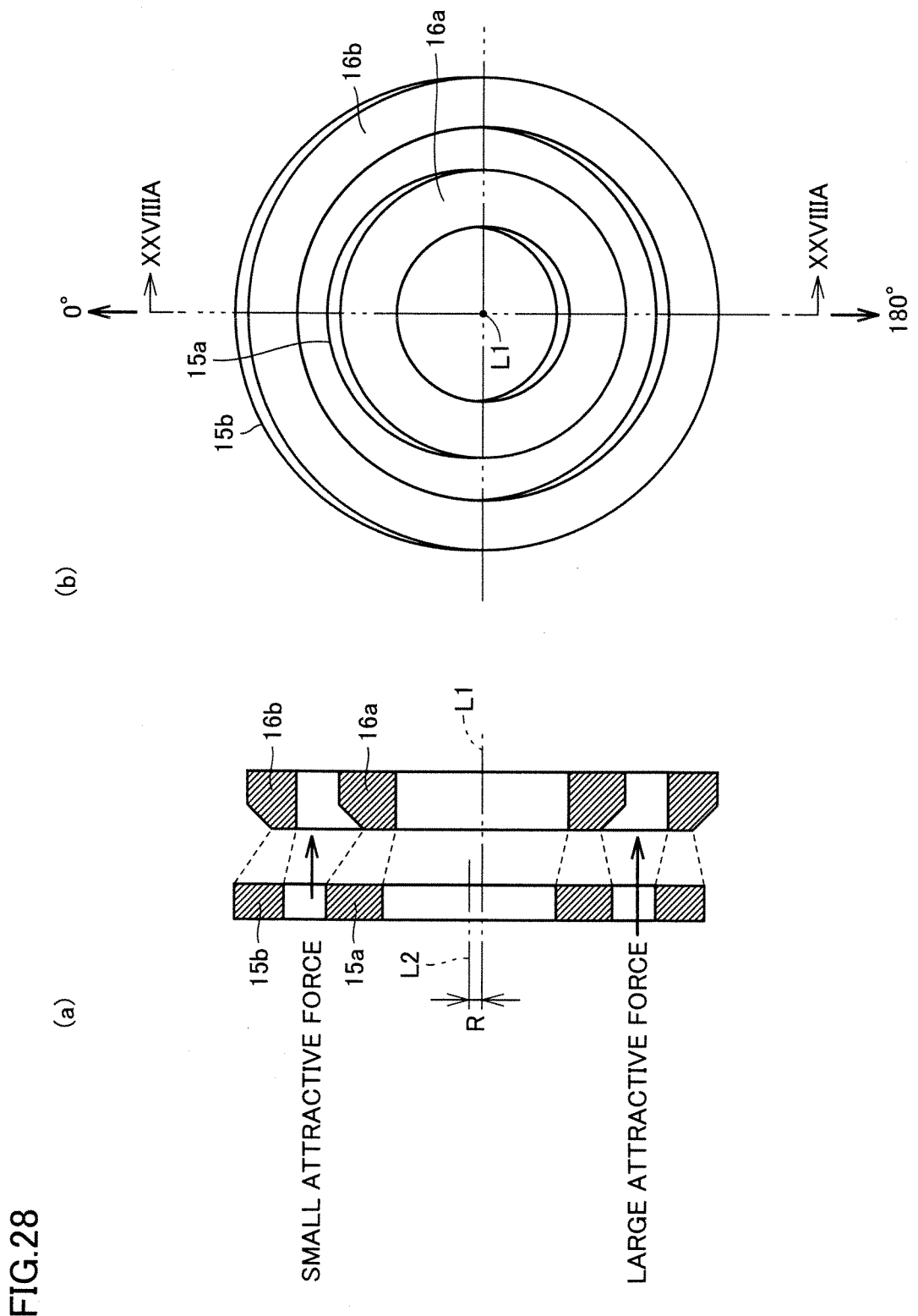
FIG. 28 is a diagram showing an effect of the modification shown in FIG. 27.

FIGS. 28(a) and (b) are diagrams showing the attractive force between permanent magnets 15a, 15b and permanent magnets 16a, 16b when impeller 10 rotates, and with the increase in discharge flow rate, impeller 10 moves to the opening 7a side (in the direction of 0 degree). FIG. 28(a) is a cross-sectional view along the line XXVIIIA-XXVIIIA in FIG. 28(b). When impeller 10 moves to the opening 7a side, a deviation occurs in positional relation between centerline L2 of permanent magnets 15a, 15b and centerline L1 of permanent magnets 16a, 16b. When the shape of permanent magnets 15a and 15b is the same as that of permanent magnets 16a and 16b, unbalance is not caused between the attractive force on the opening 7a side and the attractive force on the opposite side of opening 7a even if centerline L1 is deviated from centerline L2. Since only the outer circumferences of permanent magnets 16a and 16b are chamfered in this modification, the attractive force on the opening 7a side becomes smaller than the attractive force on the opposite side of opening 7a when centerline L1 is deviated from centerline L2. Therefore, inclination of impeller 10 is suppressed.

Figure 29:
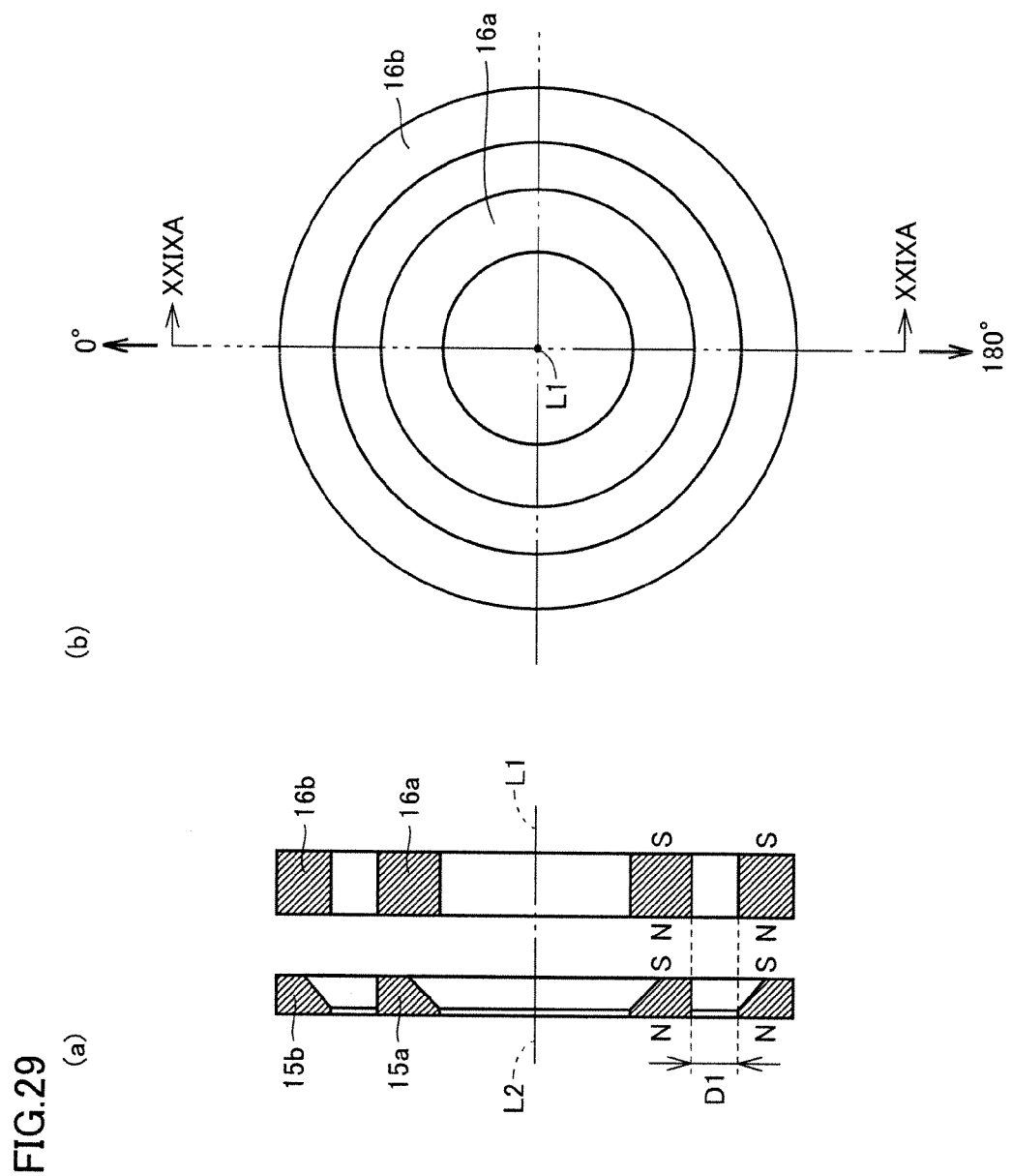
FIG. 29 is a diagram showing yet another modification of the first embodiment.

FIGS. 29(a) and (b) are diagrams showing yet another modification of the first embodiment, which are compared to FIGS. 7(a) and (b). FIG. 29(a) is a cross-sectional view along the line XXIXA-XXIXA in FIG. 29(b). Referring to FIGS. 29(a) and (b), in this modification, the entire inner circumferences of annular permanent magnets 15a and 15b are chamfered. Only a surface of permanent magnets 15a and 15b facing permanent magnets 16a and 16b may be chamfered, or a surface opposite to the surface facing permanent magnets 16a and 16b may be chamfered, or both surfaces of permanent magnets 15a and 15b may be chamfered. A size of chamfering is not particularly limited, either.

Figure 30:
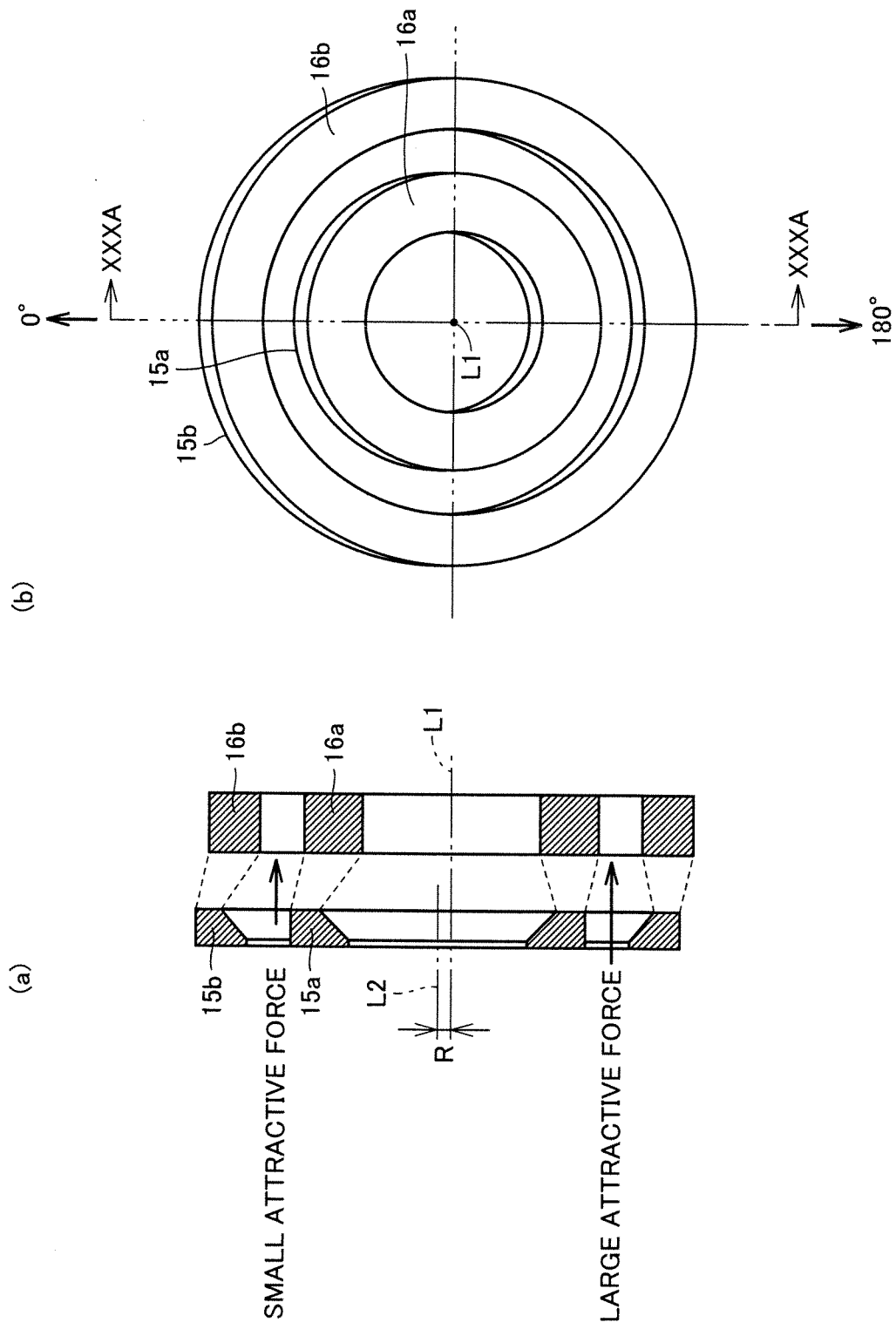
FIG. 30 is a diagram showing an effect of the modification shown in FIG. 29.

FIGS. 30(a) and (b) are diagrams showing the attractive force between permanent magnets 15a, 15b and permanent magnets 16a, 16b when impeller 10 rotates, and with the increase in discharge flow rate, impeller 10 moves to the opening 7a side (in the direction of 0 degree). FIG. 30(a) is a cross-sectional view along the line XXXA-XXXA in FIG. 30(b). When impeller 10 moves to the opening 7a side, a deviation occurs in positional relation between centerline L2 of permanent magnets 15a, 15b and centerline L1 of permanent magnets 16a, 16b. When the shape of permanent magnets 15a and 15b is the same as that of permanent magnets 16a and 16b, unbalance is not caused between the attractive force on the opening 7a side and the attractive force on the opposite side of opening 7a even if centerline L1 is deviated from centerline L2. Since only the inner circumferences of permanent magnets 15a and 15b are chamfered in this modification, the attractive force on the opening 7a side becomes smaller than the attractive force on the opposite side of opening 7a when centerline L1 is deviated from centerline L2. Therefore, inclination of impeller 10 is suppressed.

Figure 31:
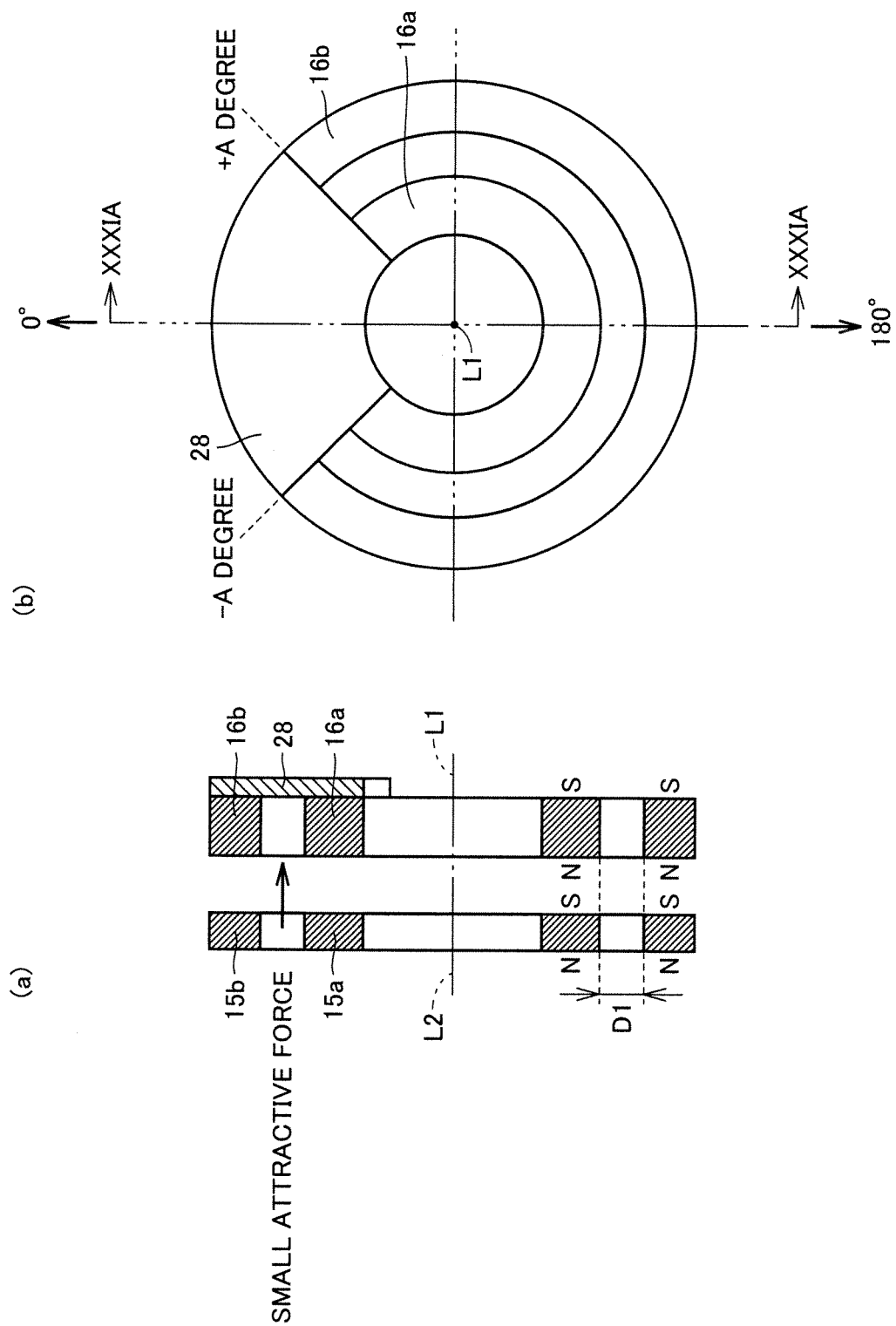
FIG. 31 is a diagram showing yet another modification of the first embodiment.

FIGS. 31(a) and (b) are diagrams showing yet another modification of the first embodiment, which are compared to FIGS. 7(a) and (b). FIG. 31(a) is a cross-sectional view along the line XXXIA-XXXIA in FIG. 31(b). Referring to FIGS. 31(a) and (b), in this modification, a thickness of annular permanent magnets 16a and 16b is fixed. The N-poles of permanent magnets 16a, 16b are oriented in the same direction. The S-poles of permanent magnets 15a, 15b face the N-poles of permanent magnets 16a, 16b. Within the range of 0 degree±A degree when viewed from the central points of permanent magnets 16a and 16b, a sector-shaped magnetic element 28 is provided to cover a surface opposite to a surface of permanent magnets 16a and 16b facing permanent magnets 15a and 15b. The A degree is a prescribed angle that is larger than 0 degree and smaller than 180 degrees, and is preferably 60 degrees. Magnetic element 28 is attracted by permanent magnets 16a and 16b. In a region where magnetic element 28 is provided, the attractive force between permanent magnets 15a, 15b and permanent magnets 16a, 16b is small. Therefore, the attractive force between permanent magnets 15a, 15b and permanent magnets 16a, 16b on the opening 7a side becomes smaller than the attractive force between permanent magnets 15a, 15b and permanent magnets 16a, 16b on the opposite side of opening 7a. The same effect as in the first embodiment can be obtained also in this modification.

Figure 32:
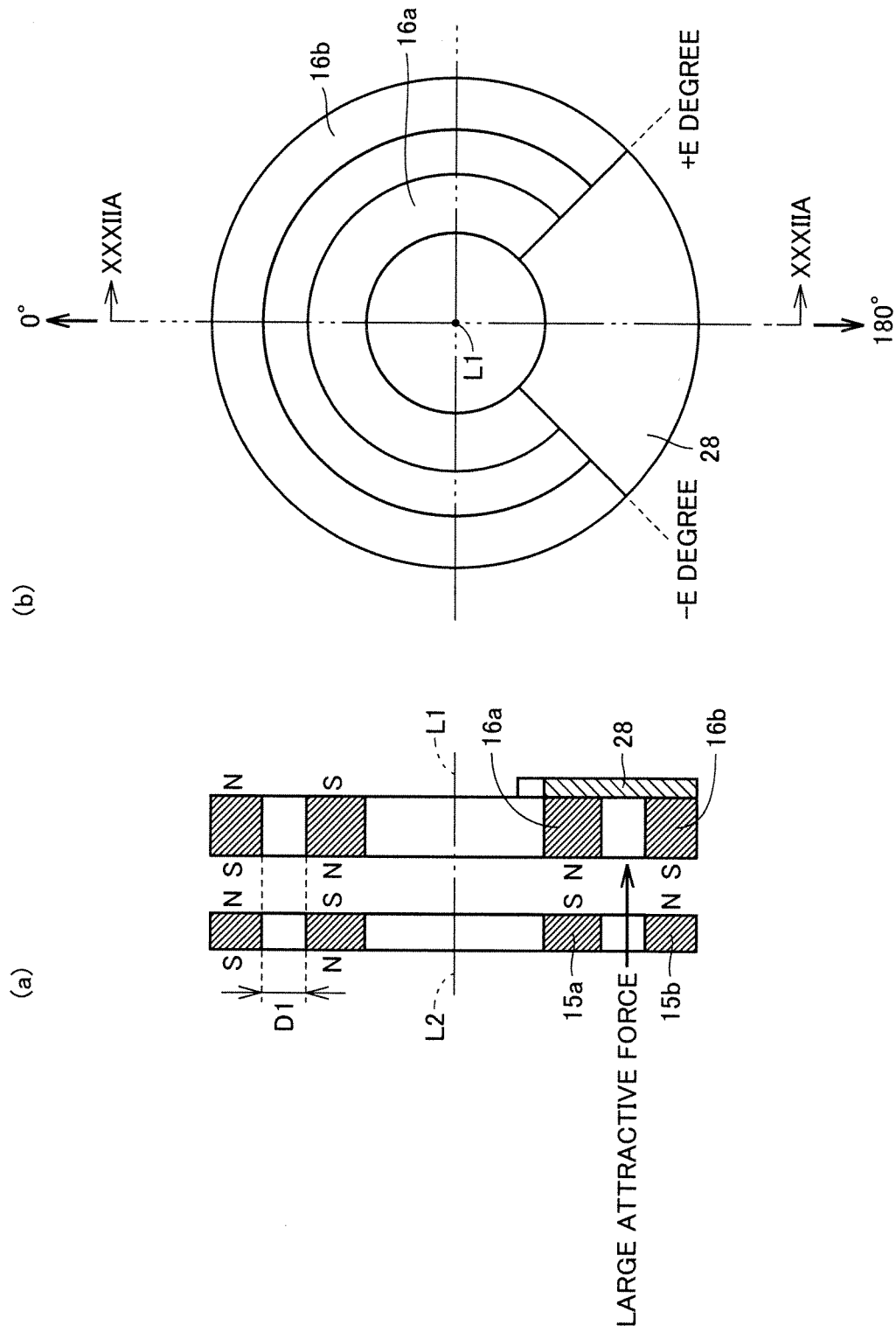
FIG. 32 is a diagram showing yet another modification of the first embodiment.

FIGS. 32(a) and (b) are diagrams showing yet another modification of the first embodiment, which are compared to FIGS. 31(a) and (b). FIG. 32(a) is a cross-sectional view along the line XXXIIA-XXXIIA in FIG. 32(b). Referring to FIGS. 32(a) and (b), in this modification, a thickness of annular permanent magnets 16a and 16b is fixed. The N-pole of permanent magnet 16a and the N-pole of permanent magnet 16b are oriented in directions opposite to each other. The S-poles of permanent magnets 15a, 15b face the N-poles of permanent magnets 16a, 16b. Within a range of±E degree when viewed from the central points of permanent magnets 16a and 16b in the direction of 180 degrees, sector-shaped magnetic element 28 is provided to cover a surface opposite to a surface of permanent magnets 16a and 16b facing permanent magnets 15a and 15b. The E degree is a prescribed angle that is larger than 0 degree and smaller than 180 degrees. Magnetic element 28 is attracted by permanent magnets 16a and 16b. In a region where magnetic element 28 is provided, the attractive force between permanent magnets 15a, 15b and permanent magnets 16a, 16b is large. Therefore, the attractive force between permanent magnets 15a, 15b and permanent magnets 16a, 16b on the opening 7a side becomes smaller than the attractive force between permanent magnets 15a, 15b and permanent magnets 16a, 16b on the opposite side of opening 7a. The same effect as in the first embodiment can be obtained also in this modification.

[Second Embodiment]

Figure 33:
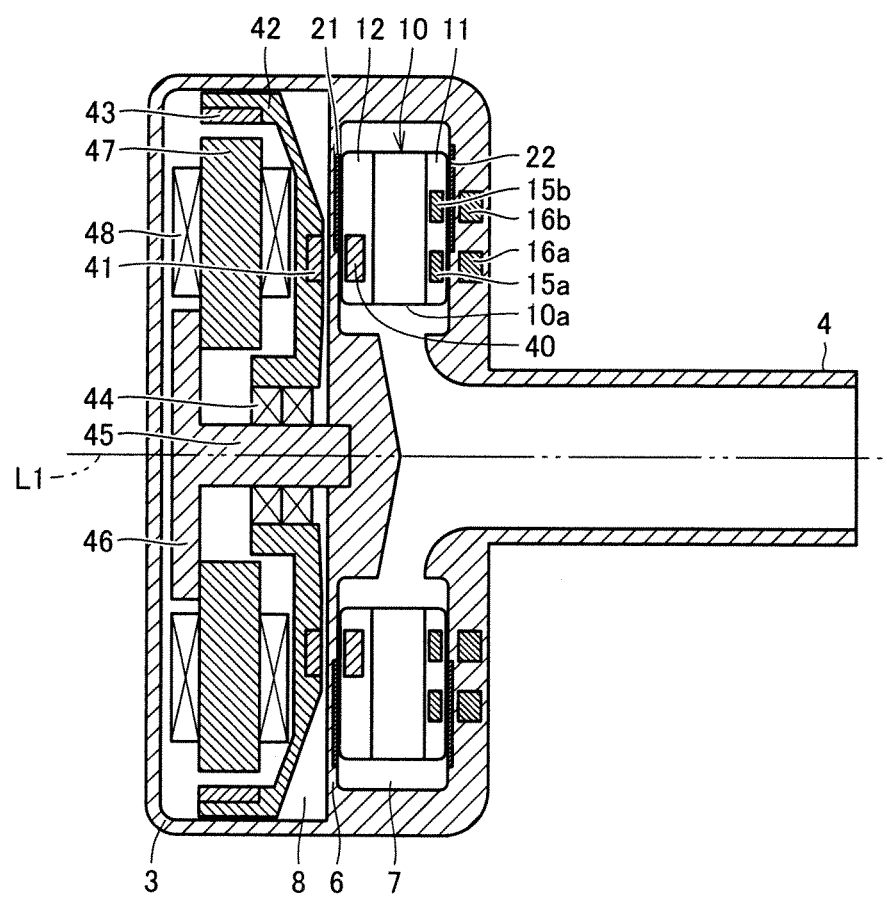
FIG. 33 is a cross-sectional view showing a structure of a pump unit of a centrifugal blood pump apparatus according to a second embodiment of the present invention.

FIG. 33 is a cross-sectional view showing a structure of a pump unit of a centrifugal blood pump apparatus according to a second embodiment of the present invention, which is compared to FIG. 3. In FIG. 33, the shape of permanent magnets 15a, 15b, 16a, and 16b is the same as that in the first embodiment. In this pump unit, a plurality of (e.g., eight) permanent magnets 40 instead of the plurality of permanent magnets 17 are embedded in shroud 12 of impeller 10. The plurality of permanent magnets 40 are arranged at regular angular intervals along the same circle. In motor chamber 8, a plurality of (e.g., eight) permanent magnets 41 for attracting the plurality of permanent magnets 40 are provided. The plurality of permanent magnets 41 are arranged at regular angular intervals along the same circle to face the plurality of permanent magnets 40 in impeller 10.

The plurality of permanent magnets 41 are provided in a surface of a bowl-shaped rotor 42. A plurality of (e.g., eight) permanent magnets 43 are provided at regular angular intervals on an inner side of a circumference of rotor 42. The plurality of permanent magnets 43 are arranged at regular angular intervals along the same circle such that adjacent magnetic poles thereof are different from each other. In other words, permanent magnet 43 having the N-pole oriented to the inside of rotor 42 and permanent magnet 43 having the S-pole oriented to the inside of rotor 42 are alternately arranged at regular angular intervals along the same circle.

A central portion of rotor 42 is rotatably supported by a central axis 45 with a bearing 44 being interposed, and rotor 42 is rotatably provided along dividing wall 6. A rotation centerline of rotor 42 matches centerline L1 of the sidewall of blood chamber 7. Central axis 45 is provided to stand in a center of a disc-shaped yoke 46. A plurality of (e.g., nine) magnetic elements 47 are provided at regular angular intervals around central axis 45 on the surface of yoke 46. Tip ends of the plurality of magnetic elements 47 are arranged along the same circle, as facing the plurality of permanent magnets 43 in rotor 42. A coil 48 is wound around each magnetic element 47. The plurality of permanent magnets 43, the plurality of magnetic elements 47, and a plurality of coils 48 constitute a motor for rotating rotor 42.

Voltages are applied to nine coils 48 in a power distribution system shifted by 120 degrees, for example. Namely, nine coils 48 are divided into groups each including three coils. Voltages VU, VV and VW shown in FIG. 9 are applied to first to third coils 48 of each group, respectively. Thus, rotating magnetic field can be formed by applying voltages VU, VV and VW to first to third coils 48, respectively, and rotor 42 can be rotated by attractive force and repulsion force between the plurality of magnetic elements 47 and the plurality of permanent magnets 43 in rotor 42. As rotor 42 rotates, impeller 10 rotates as a result of attractive force from the plurality of permanent magnets 43 in rotor 42 and the plurality of permanent magnets 40 in impeller 10.

Here, when impeller 10 is rotating at a rated rotation speed, attractive force between permanent magnets 15a, 15b and permanent magnets 16a, 16b and attractive force between the plurality of permanent magnets 40 and the plurality of permanent magnets 41 are set to be balanced with each other substantially around the center of the movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be lowered. In addition, a surface of impeller 10 and a surface of the inner wall of housing 2 are not damaged (no projections and recesses in the surfaces) during the relative slide, and moreover, impeller 10 is readily levitated from housing 2 without contacting even when hydrodynamic force is small during low-speed rotation.

In addition, as in the first embodiment, grooves for hydrodynamic bearing 21 are formed in the surface of dividing wall 6 facing shroud 12 of impeller 10, and grooves for hydrodynamic bearing 22 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21, 22 and impeller 10. As a result, drag is generated on impeller 10 from each of grooves for hydrodynamic bearing 21, 22, causing impeller 10 to rotate without contacting in blood chamber 7.

In addition, as in the first embodiment, the attractive force between permanent magnets 15a, 15b and permanent magnets 16a, 16b on the opening 7a side of the sidewall of blood chamber 7 is set to be smaller than the attractive force between permanent magnets 15a, 15b and permanent magnets 16a, 16b on the opposite side of opening 7a. Therefore, impeller 10 can become parallel to dividing wall 6 during rotation, and contact of impeller 10 with the inner wall of blood chamber 7 can be prevented.

In addition, the attractive force between permanent magnets 15a, 15b and permanent magnets 16a, 16b is balanced with the attractive force between the plurality of permanent magnets 40 and the plurality of permanent magnets 41, and grooves for hydrodynamic bearing 21, 22 are provided. Therefore, rigidity for supporting impeller 10 in the axial direction can be increased. In addition, since two pairs of permanent magnets 15a and 16a and permanent magnets 15b and 16b are provided in the radial direction of impeller 10, rigidity for supporting impeller 10 in the radial direction can be increased as compared with a case where only a pair of permanent magnets is provided in the radial direction of impeller 10. Therefore, mechanical contact between impeller 10 and housing 2 can be lessened and occurrence of hemolysis or thrombus can be prevented.

[Third Embodiment]

Figure 34:
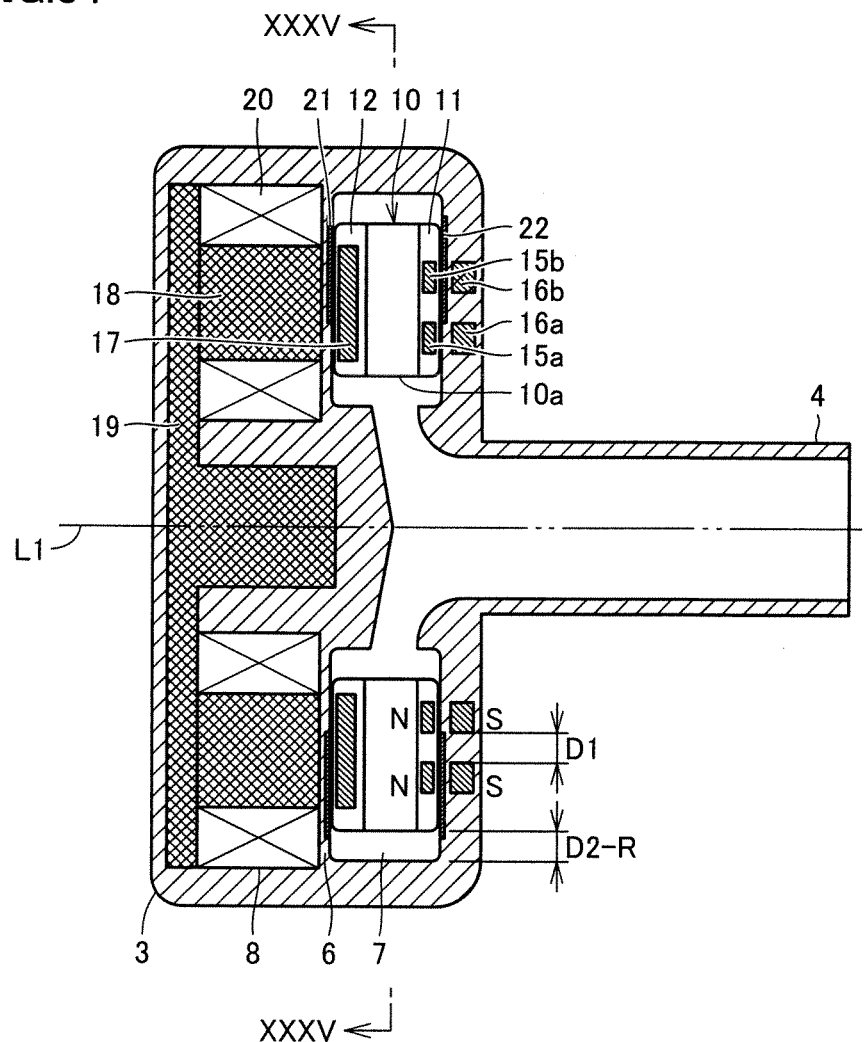
FIG. 34 is a cross-sectional view showing a structure of a pump unit of a centrifugal blood pump apparatus according to a third embodiment of the present invention.
Figure 35:
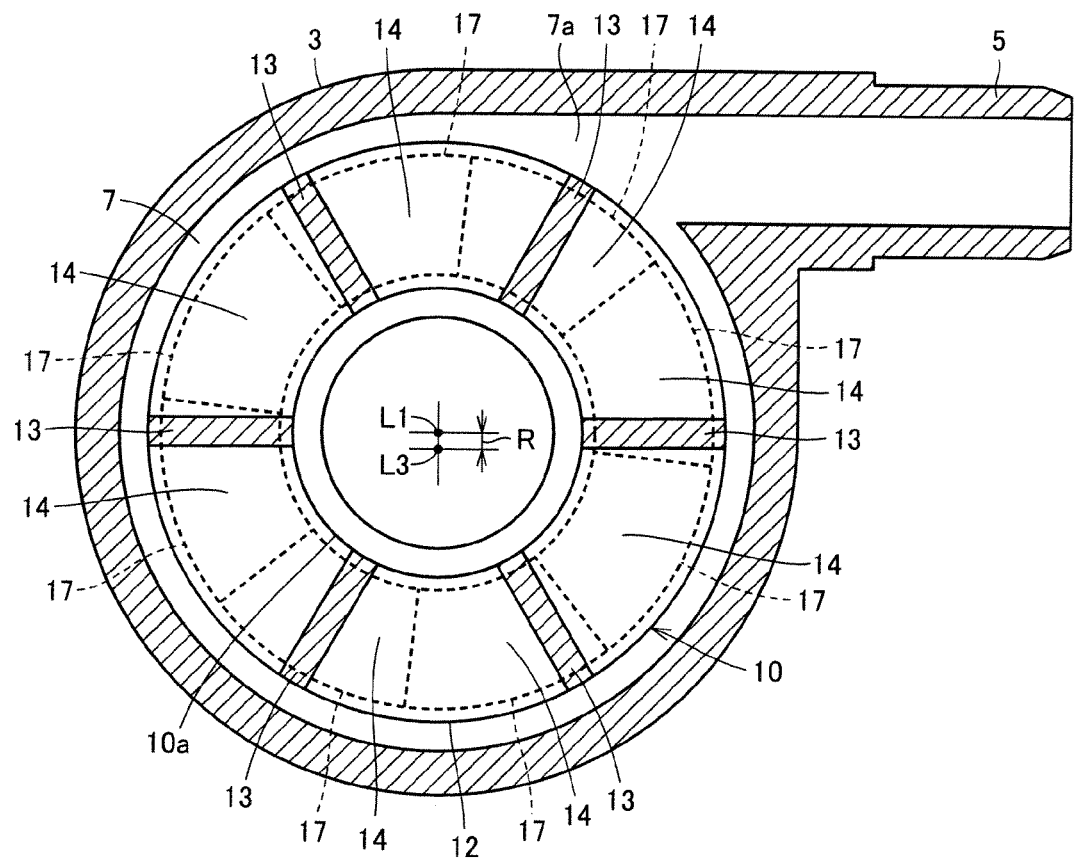
FIG. 35 is a cross-sectional view along the line XXXV-XXXV in FIG. 34.

FIG. 34 is a cross-sectional view showing a structure of a pump unit of a centrifugal blood pump apparatus according to a third embodiment of the present invention, which is compared to FIG. 3. FIG. 35 is a cross-sectional view along the line XXXV-XXXV in FIG. 34, which is compared to FIG. 4. FIGS. 36(a) and (b) are diagrams showing a structure of permanent magnets 15a, 15b, 16a, and 16b, which are compared to FIGS. 7(a) and (b).

In FIGS. 34 and 35, permanent magnets 15a, 15b are embedded in shroud 11 and permanent magnets 16a, 16b for attracting permanent magnets 15a, 15b respectively are embedded in an inner wall of blood chamber 7 facing shroud 11. Permanent magnets 15a, 15b, 16a, and 16b are provided to attract (in other words, bias) impeller 10 to the side opposite to motor chamber 8, that is, toward blood inlet port 4. When impeller 10 is rotated, impeller 10 is attracted to the opening 7a side. Therefore, in order to attract (in other words, bias) impeller 10 to the side opposite to opening 7a, a centerline L3 of permanent magnets 16a, 16b is arranged on the side opposite to opening 7a when viewed from a centerline L1 of the inner wall of blood chamber 7.

FIGS. 36(a) and (b) are diagrams showing a structure of permanent magnets 15a, 15b, 16a, and 16b and FIG. 36(a) is a cross-sectional view along the line XXXVIA-XXXVIA in FIG. 36(b). FIGS. 36(a) and (b) show a state where impeller 10 is not rotated and permanent magnets 15a, 15b are attracted to permanent magnets 16a, 16b. In this state, centerline L2 of permanent magnets 15a, 15b (i.e., centerline of impeller 10) matches centerline L3 of permanent magnets 16a, 16b. The shape of permanent magnets 15a, 15b, 16a, and 16b is the same as that in the first embodiment. Centerline L3 of permanent magnets 16a, 16b is distant from centerline L1 of the inner wall of blood chamber 7 by a prescribed distance R.

Detailed description will now be given to a reason why centerline L3 of permanent magnets 16a, 16b is distant from centerline L1 of the inner wall of blood chamber 7. When unbalance in pressure in blood chamber 7 is caused in a pump apparatus that does not substantially include a volute, like this centrifugal blood pump apparatus, impeller 10 moves in the radial direction in accordance with the pressure balance in blood chamber 7. Specifically, rotation centerline L2 of impeller 10 moves toward opening 7a, which is a low pressure portion in blood chamber 7.

Figure 37:
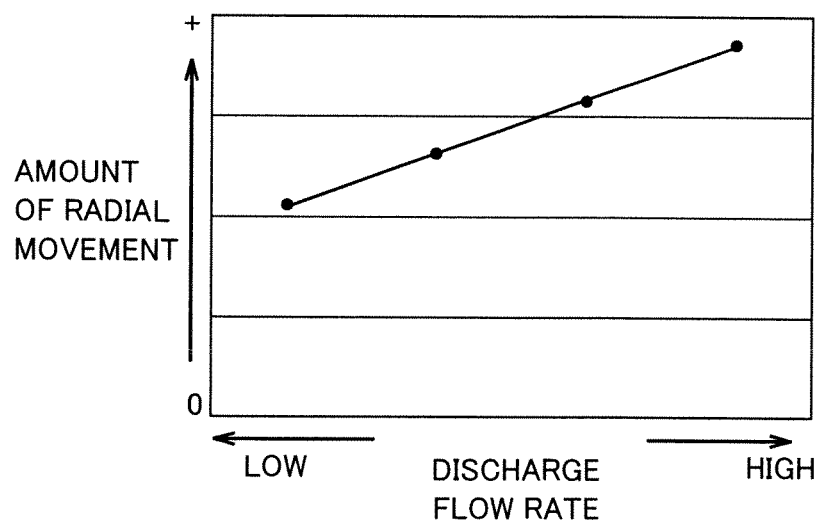
FIG. 37 is a diagram showing relation between a rotation speed of an impeller and an amount of radial movement of the impeller.
Figure 38:
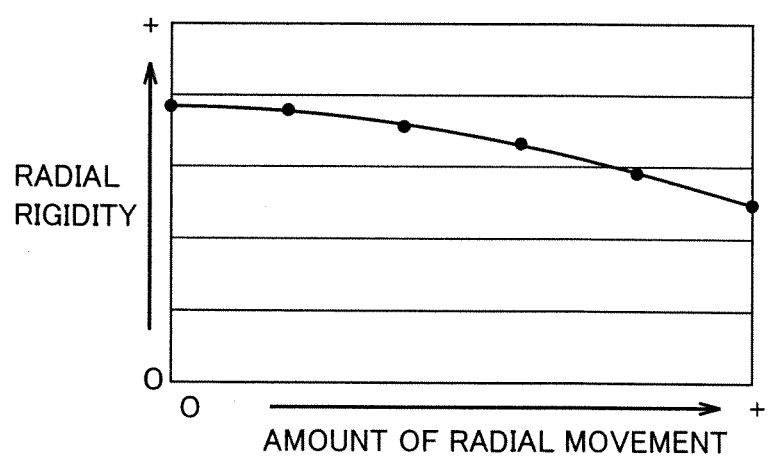
FIG. 38 is a diagram showing relation between an amount of radial movement of the impeller and radial rigidity in magnetic coupling.

As shown in FIG. 37, as a discharge flow rate from the pump apparatus increases, unbalance in pressure in blood chamber 7 increases and an amount of radial movement of impeller 10 increases. In addition, as shown in FIG. 38, as the amount of radial movement of impeller 10 increases, radial rigidity in magnetic coupling decreases. Therefore, in such a situation that rotation centerline L2 of impeller 10 does not match centerline L1 of the sidewall of blood chamber 7, a position of impeller 10 fluctuates due to reception of small disturbance in the radial direction, and the sidewall of blood chamber 7 may come in contact with the side surface of impeller 10. Even when the sidewall of blood chamber 7 does not come in contact with the side surface of impeller 10, hemolysis, which is breakdown of erythrocyte in blood, may also occur at a portion where a gap therebetween has become narrower.

Figure 39:
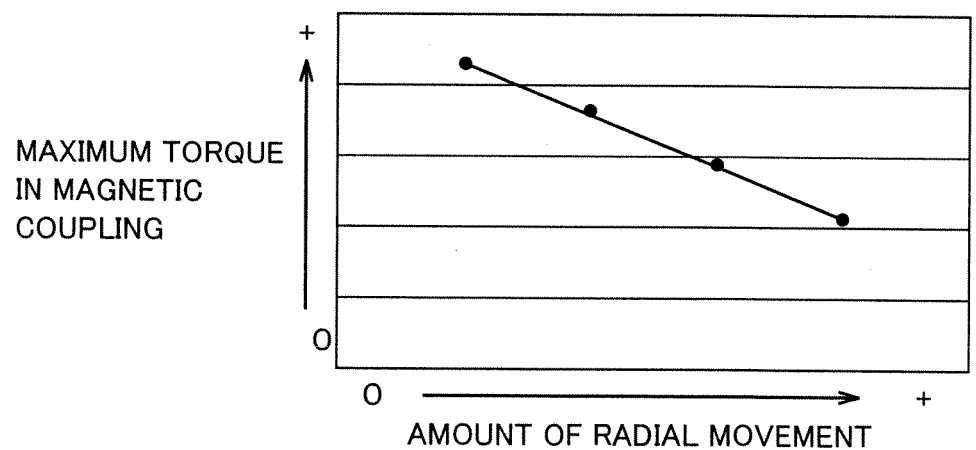
FIG. 39 is a diagram showing relation between an amount of radial movement of the impeller and maximum torque in magnetic coupling.

Since the pressure gradient is large and the pressure is low at opening 7a and its surrounding region, impeller 10 is attracted to opening 7a as impeller 10 comes closer to opening 7a. On the other hand, axis torque for providing the hydro-energy from impeller 10 to blood acts on impeller 10 as load during pump operation, and the axis torque increases with increase in rotation speed. In addition, as shown in FIG. 39, as the amount of radial movement of impeller 10 increases, maximum transmission torque in magnetic coupling decreases. Therefore, loss of coupling may occur when the maximum transmission torque in magnetic coupling becomes smaller than the axis torque acting on impeller 10.

Figure 40:
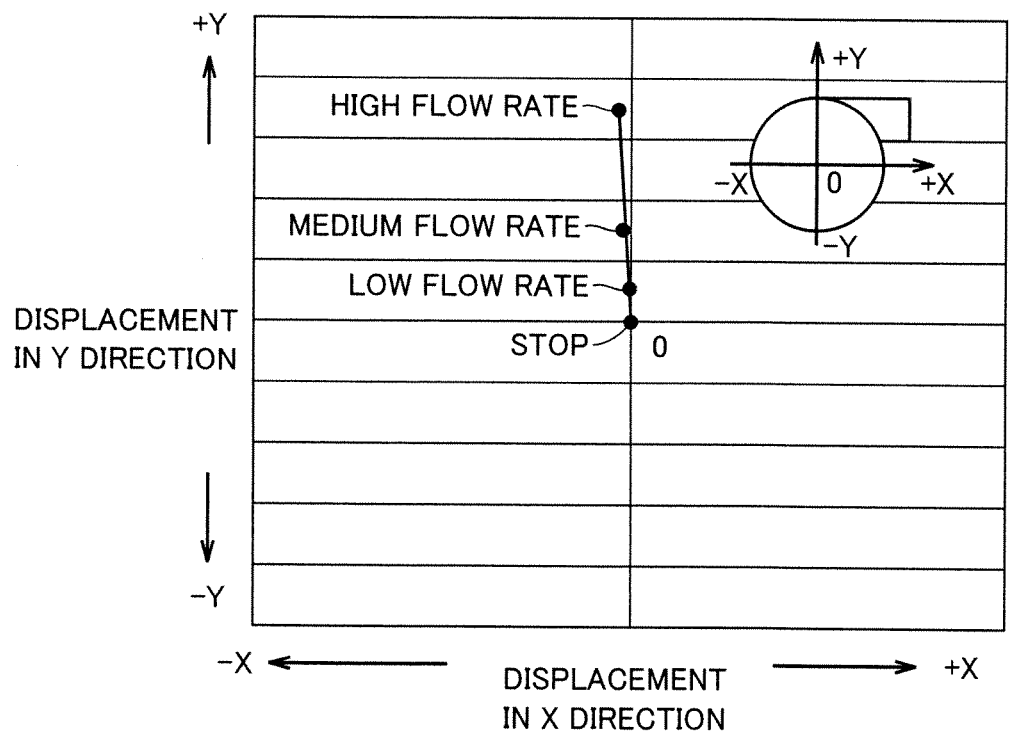
FIG. 40 is a diagram showing a rotation speed of the impeller and radial displacement of a rotation centerline of the impeller.

FIG. 40 is a diagram showing relation between a discharge flow rate and a movement direction and an amount of movement of rotation centerline L2 of impeller 10 in the centrifugal blood pump apparatus where centerline L1 of the sidewall of blood chamber 7 matches centerline L3 of permanent magnets 16a, 16b. In FIG. 40, centerline L1 of the sidewall of blood chamber 7 and centerline L3 of permanent magnets 16a, 16b are arranged at the origin point and a direction of an end of opening 7a on the upstream side is defined as the Y direction. It can be seen from this FIG. 40 that rotation centerline L2 of impeller 10 moves to be attracted toward the end of opening 7a on the upstream side, as the discharge flow rate increases.

Accordingly, in this third embodiment, centerline L3 of permanent magnets 16a, 16b is arranged on the side opposite to opening 7a when viewed from centerline L1 of the sidewall of blood chamber 7, such that rotation centerline L2 of impeller 10 matches centerline L1 of the sidewall of blood chamber 7 when impeller 10 is rotated at a rated rotation speed, and impeller 10 is attracted (in other words, biased) to the side opposite to opening 7a. Interval R between centerlines L1 and L3 is set depending on operation conditions. In other words, an amount of displacement may be read from FIG. 40 based on the discharge flow rate when impeller 10 is rotated at a rated rotation speed, and interval R between centerlines L1 and L3 may be set to this amount of displacement. The interval (an amount of eccentricity) between centerlines L1 and L3 varies depending on the pump size and the like, and the interval of 0.1 to 1.0 mm is suitable. As a result, when impeller 10 is rotated at a rated rotation speed, rotation centerline L2 of impeller 10 matches centerline L1 of the sidewall of blood chamber 7.

Figure 41:
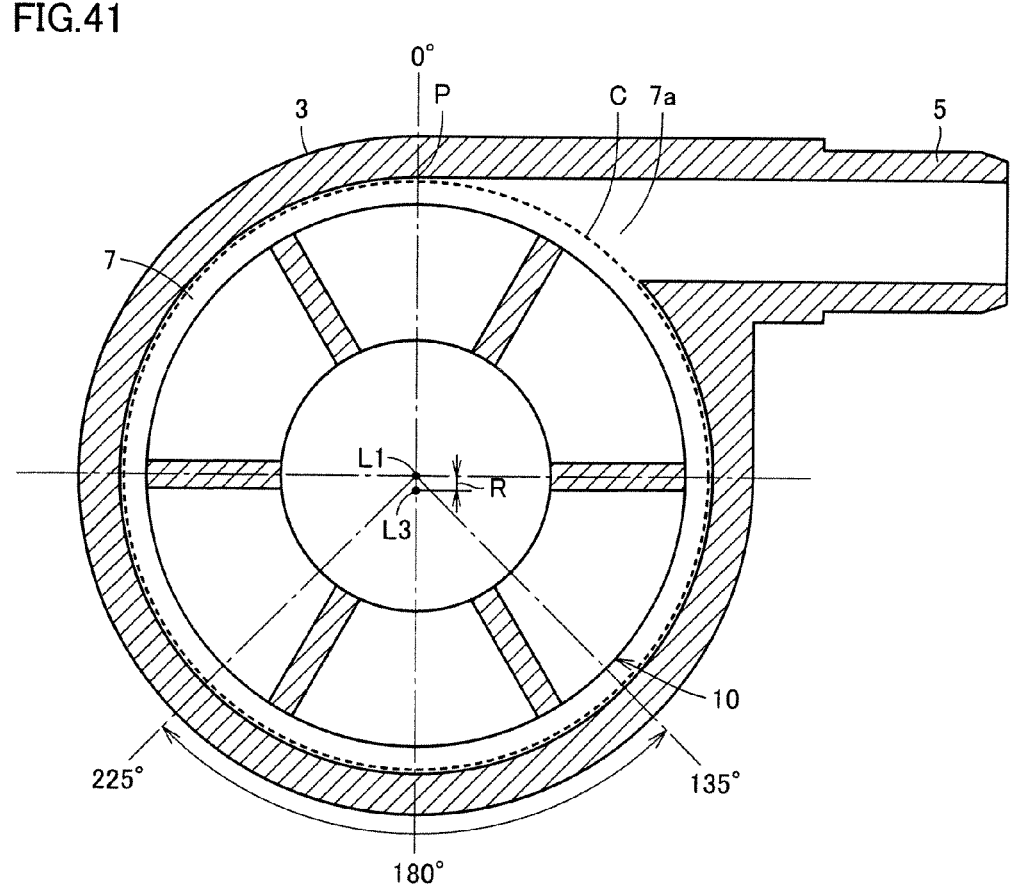
FIG. 41 is a diagram showing positional relation between a centerline of a sidewall of a blood chamber and a centerline of the permanent magnet.

FIG. 41 is a diagram showing positional relation between centerline L1 of the inner wall of blood chamber 7 and centerline L3 of permanent magnets 16a, 16b. In FIG. 41, housing 2 is cut in a plane orthogonal to centerline L1 of the sidewall of blood chamber 7 and including a centerline of a hole in blood outlet port 5. The sidewall of blood chamber 7 is formed along a circle C on this plane. A central point of circle C is an intersection point of this plane and centerline L1 of the sidewall of blood chamber 7. The hole in blood outlet port 5 extends in the tangential direction of circle C. In FIG. 41, impeller 10 rotates in a direction of rotation of clock hands and blood also rotates in this direction. A contact point P between the hole in blood outlet port 5 and circle C is located at an end of opening 7a on the upstream side (the left side in FIG. 41) in the sidewall of blood chamber 7.

Assuming that a direction of contact point P (the end of opening 7a on the upstream side) is defined as 0 degree and the opposite direction is defined as 180 degrees when viewed from the central point of circle C (centerline L1 of the sidewall of blood chamber 7), centerline L3 of permanent magnets 16a, 16b is arranged at a position displaced from the central point of circle C in the direction of 180 degrees by prescribed amount of eccentricity R.

Movement characteristics of impeller 10 in the radial direction during pump operation vary depending on an area, a shape and the like of opening 7a. Therefore, the position of centerline L3 of permanent magnets 16a, 16b is not necessarily limited to the direction of 180 degrees from the central point of circle C. The position of centerline L3 of permanent magnets 16a, 16b is preferably within the range of 180 degrees±45 degrees (i.e., 135 degrees to 225 degrees) from the central point of circle C.

As shown in FIG. 34, when an interval between permanent magnets 15a and 15b (i.e., interval between permanent magnets 16a and 16b) is expressed as D1 and ½ of a movable distance of impeller 10 in the radial direction (i.e., distance of a difference between the inner diameter of blood chamber 7 and the outer diameter of impeller 10) is expressed as D2, relation of 0.5×D1>D2+R is satisfied. This is because, when impeller 10 moves in the radial direction to a maximum extent while relation of 0.5×D1<D2+R is satisfied, permanent magnets 15a and 16b interfere with each other and permanent magnets 15b and 16a interfere with each other and hence returning force for returning impeller 10 to a central position of the pump becomes unstable.

The remaining structure and operation are the same as those in the first embodiment, and thus, description thereof will not be repeated. In this third embodiment, inclination of impeller 10 can be prevented as in the first embodiment, and impeller 10 can be positioned at the center of blood chamber 7.

Figure 42:
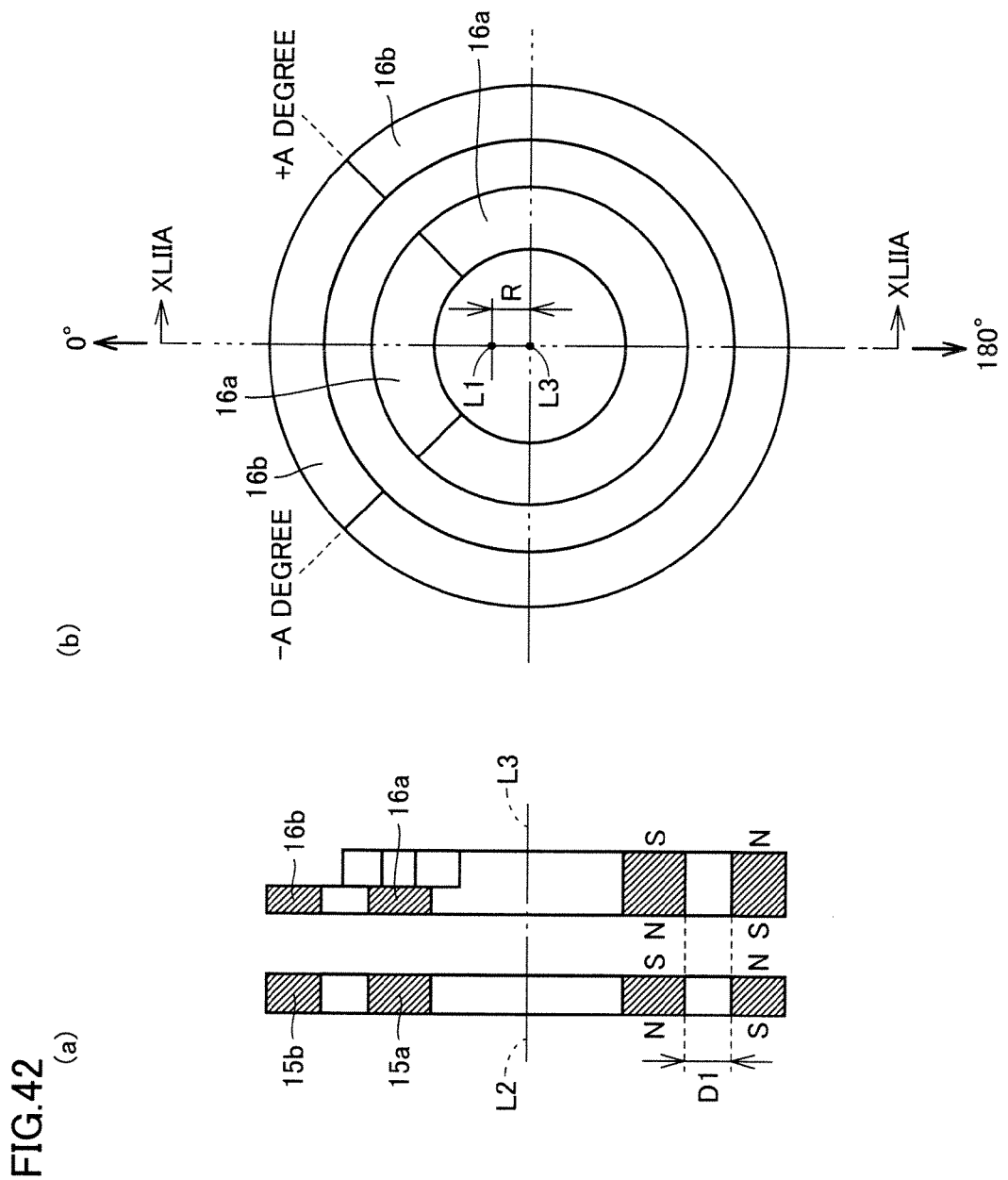
FIG. 42 is a diagram showing a modification of this embodiment.

FIGS. 42(a) and (b) are cross-sectional views showing a modification of this third embodiment, which are compared to FIGS. 36(a) and (b). FIG. 42(a) is a cross-sectional view along the line XLIIA-XLIIA in FIG. 42(b). In this modification, the N pole of permanent magnet 15a and the N pole of permanent magnet 15b are provided in directions opposite to each other, and the N pole of permanent magnet 16a and the N pole of permanent magnet 16b are provided in directions opposite to each other. The S pole of permanent magnet 15a faces the N pole of permanent magnet 16a and the N pole of permanent magnet 15b faces the S pole of permanent magnet 16b. That is, heteropolar arrangement is implemented. The same effect as in the third embodiment can be obtained also in this modification.

In addition, in the modification in FIGS. 42(a) and (b), when an interval between permanent magnets 15a and 15b (i.e., interval between permanent magnets 16a and 16b) is expressed as D1, ½ of a movable distance of impeller 10 in the radial direction (i.e., distance of a difference between the inner diameter of blood chamber 7 and the outer diameter of impeller 10) is expressed as D2, and the aforementioned amount of eccentricity is expressed as R, relation of D1>D2+R is satisfied. This is because, when impeller 10 moves in the radial direction to a maximum extent while relation of D1<D2+R is satisfied, permanent magnets 15a and 16b interfere with each other and permanent magnets 15b and 16a interfere with each other and hence returning force for returning impeller 10 to a central position of the pump becomes unstable.

As described with reference to FIGS. 36(a) and (b) and FIGS. 42(a) and (b), allowable interval D1 between permanent magnets 15a and 15b (i.e., interval between permanent magnets 16a and 16b) varies depending on polarity arrangement of permanent magnets 15a, 15b and permanent magnets 16a, 16b. This is because depending on polarity arrangement, the degree of interference of permanent magnets 15a and 16b and the degree of interference of permanent magnets 15b and 16a vary, and the maximum amount of eccentricity at which loss of coupling occurs varies as shown in FIG. 43.

Figure 43:
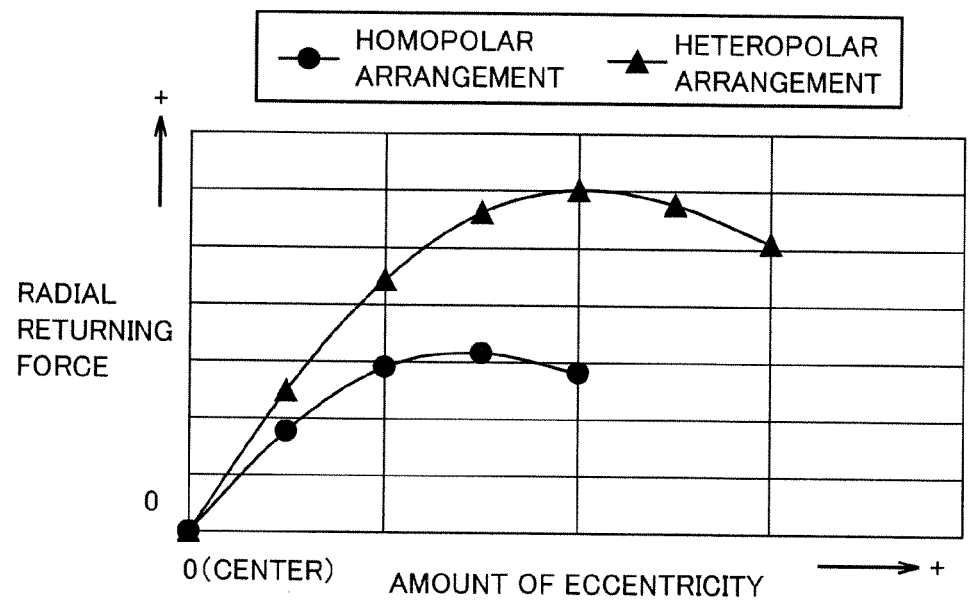
FIG. 43 is a diagram showing relation between an amount of eccentricity in a centerline of permanent magnets 15a, 15b and a centerline of permanent magnets 16a, 16b and radial returning force of impeller 10.

In other words, FIG. 43 is a diagram showing relation between an amount of eccentricity in centerline L2 of permanent magnets 15a, 15b and centerline L3 of permanent magnets 16a, 16b and radial returning force of impeller 10. In FIG. 43, homopolar arrangement refers to a case where the N poles of two permanent magnets 15a and 15b adjacent in the radial direction are oriented in the same direction and the N poles of two permanent magnets 16a and 16b adjacent in the radial direction are oriented in the same direction as shown in FIGS. 36(a) and (b). Heteropolar arrangement refers to a case where the N poles of two permanent magnets 15a and 15b adjacent in the radial direction are oriented in different directions and the N poles of two permanent magnets 16a and 16b adjacent in the radial direction are oriented in different directions as shown in FIGS. 42(a) and (b).

As can be seen in FIG. 43, as the amount of eccentricity in centerline L2 of permanent magnets 15a, 15b and centerline L3 of permanent magnets 16a, 16b is increased, the radial returning force of impeller 10 temporarily rises, and then, falls. The radial returning force of impeller 10 in heteropolar arrangement is larger than the radial returning force of impeller 10 in homopolar arrangement. In addition, the amount of eccentricity at which a peak value appears in the case of heteropolar arrangement is larger than the amount of eccentricity at which a peak value appears in the case of homopolar arrangement. Therefore, the maximum amount of eccentricity at which loss of coupling occurs is larger in the case of heteropolar arrangement than in the case of homopolar arrangement.

A reason for this is considered as follows. In the case of heteropolar arrangement, in FIGS. 42(a) and (b), when centerline L2 of permanent magnets 15a, 15b relatively moves below centerline L3 of permanent magnets 16a, 16b, repulsion force is generated between the S pole of permanent magnet 15a and the S pole of permanent magnet 16b. This repulsion force increases the radial returning force of impeller 10. In contrast, in the case of homopolar arrangement, in FIGS. 36(a) and (b), when centerline L2 of permanent magnets 15a, 15b relatively moves below centerline L3 of permanent magnets 16a, 16b, attractive force is generated between the S pole of permanent magnet 15a and the N pole of permanent magnet 16b. This attractive force decreases the radial returning force of impeller 10. Therefore, the maximum amount of eccentricity at which loss of coupling occurs in heteropolar arrangement is larger than the maximum amount of eccentricity at which loss of coupling occurs in homopolar arrangement.

It is needless to say that the embodiments and modifications described above may be combined as appropriate.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

Reference Signs List 1 pump unit; 2 housing; 3 body portion; 4 blood inlet port; 5 blood outlet port; 6 dividing wall; 7 blood chamber; 7a opening; 8 motor chamber; 10 impeller; 10a through hole; 11, 12 shroud; 13 vane; 14 blood passage; 15a, 15b, 16a, 16b, 17, 40, 41, 43 permanent magnet; 18, 28, 35, 37 to 39, 47 magnetic element; 19, 36, 46 yoke; 20, 48 coil; 21, 22 groove for hydrodynamic bearing; 25 controller; 26 motor control circuit; 27, 30, 31 power amplifier; 32 switch; 42 rotor; 44 bearing; 45 central axis

The invention claimed is:

1. A centrifugal pump apparatus including a housing having first and second chambers partitioned from each other by a dividing wall, an impeller rotatably provided in said first chamber along said dividing wall, for delivering fluid by centrifugal force during rotation, and a drive unit provided in said second chamber, for driving said impeller to rotate with said dividing wall being interposed, the centrifugal pump apparatus comprising:
a first magnetic element provided in one surface of said impeller;
a second magnetic element provided in an inner wall of said first chamber facing the one surface of said impeller, for attracting said first magnetic element
a third magnetic element provided in the other surface of said impeller and attracted by said drive unit and
a fluid outlet port for allowing said fluid to flow to the outside of said housing from an opening provided in a sidewall of said first chamber, wherein
during rotation of said impeller, a first attractive force acting between said first and second magnetic elements and a second attractive force acting between said third magnetic element and said drive unit are balanced with each other substantially in a center of a movable range of said impeller in said first chamber,
a first groove for hydrodynamic bearing is formed in the one surface of said impeller or in the inner wall of said first chamber facing the one surface and a second groove for hydrodynamic bearing is formed in the other surface of said impeller or in said dividing wall facing the other surface,
at least one of said first and second magnetic elements is formed annularly around a rotation centerline of said impeller, and
the first attractive force on an opening side of said sidewall is set to be different from the first attractive on an opposite side from said opening side of said sidewall such that said impeller becomes parallel to said dividing wall during rotation of said impeller.

2. The centrifugal pump apparatus according to claim 1, wherein
the first attractive force on said opening side is set to be smaller than the first attractive force on the opposite side of said opening.

3. The centrifugal pump apparatus according to claim 2, wherein
said second magnetic element is a permanent magnet formed annularly around the rotation centerline of said impeller, and
a thickness of said second magnetic element on said opening side is smaller than a thickness of said second magnetic element on the opposite side from said opening.

4. The centrifugal pump apparatus according to claim 2, wherein
said second magnetic element is a permanent magnet formed annularly around the rotation centerline of said impeller, and
a facing area of said first and second magnetic elements on said opening side is smaller than a facing area of said first and second magnetic elements on the opposite side from said opening.

5. The centrifugal pump apparatus according to claim 2, wherein
said second magnetic element is a permanent magnet formed annularly around the rotation centerline of said impeller, and
a notch is provided in said second magnetic element on said opening side.

6. The centrifugal pump apparatus according to claim 2, wherein
said first magnetic element includes a plurality of first permanent magnets that are different in diameter from each other and are each formed annularly, and
said second magnetic element includes a plurality of second permanent magnets that are different in diameter from each other and are each formed annularly.

7. The centrifugal pump apparatus according to claim 6, wherein
first magnetic poles of said plurality of second permanent magnets are all oriented in a direction of said impeller, and second magnetic poles of said plurality of second permanent magnets are all oriented in an opposite direction of said impeller, and second magnetic poles of said plurality of first permanent magnets are provided to face the first magnetic poles of said plurality of second permanent magnets, respectively,
the centrifugal pump apparatus further comprising:
a fourth magnetic element attracted to a predetermined region on said opening side, of the second magnetic poles of said plurality of second permanent magnets.

8. The centrifugal pump apparatus according to claim 6, wherein
a first magnetic pole of one of two adjacent second permanent magnets is oriented in a direction of said impeller, and a second magnetic pole of the other second permanent magnet is oriented in the direction of said impeller, and magnetic poles of said plurality of first permanent magnets are arranged to attract magnetic poles of said plurality of second permanent magnets, respectively,
the centrifugal pump apparatus further comprising:
a fourth magnetic element attracted to a predetermined region on the opposite side of said opening, of the magnetic poles of said plurality of second permanent magnets on an opposite side of said impeller.

9. The centrifugal pump apparatus according to claim 1, wherein
a sidewall of said first chamber facing a side surface of said impeller is formed cylindrically, and assuming that a direction of an end of said opening on an upstream side when viewed from a centerline of the sidewall of said first chamber is 0 degree and an opposite side thereof is 180 degrees, said opening side is said 0-degree direction side when viewed from the centerline of the sidewall of said first chamber, and the opposite side of said opening is said 180-degree direction side when viewed from the centerline of the sidewall of said first chamber, and
an attractive force between said first and second magnetic elements within a range of 0 degree through A degree, where the A degree is an angle that is larger than 0 degree and smaller than 180 degrees, when viewed from the centerline of the sidewall of said first chamber is smaller than an attractive force between said first and second magnetic elements outside the range.

10. The centrifugal pump apparatus according to claim 1, wherein
said drive unit includes a plurality of stator coils arranged annularly to face said third magnetic element of said impeller, for generating a rotating magnetic field and rotating said impeller, and
a centerline of the rotating magnetic field generated by said plurality of stator coils matches a centerline of the sidewall of said first chamber.

11. The centrifugal pump apparatus according to claim 1, wherein
said drive unit includes:
a plurality of fifth magnetic elements arranged annularly to face said third magnetic element of said impeller; and
a plurality of stator coils wound around said plurality of fifth magnetic elements respectively, for generating a rotating magnetic field and rotating said impeller, and
a centerline of the rotating magnetic field generated by said plurality of stator coils matches a centerline of the sidewall of said first chamber.

12. The centrifugal pump apparatus according to claim 1, wherein
said drive unit includes:
a rotor rotatably provided along said dividing wall in said second chamber;
a fifth magnetic element provided in said rotor to face said third magnetic element, for attracting said third magnetic element; and
a motor for rotating said rotor, and
a rotation centerline of said rotor matches a centerline of the sidewall of said first chamber.

13. A centrifugal pump apparatus including a housing having first and second chambers partitioned from each other by a dividing wall, an impeller rotatably provided in said first chamber along said dividing wall, for delivering fluid by centrifugal force during rotation, and a drive unit provided in said second chamber, for driving said impeller to rotate with said dividing wall being interposed, the centrifugal pump apparatus comprising:
a first magnetic element provided in one surface of said impeller;
a second magnetic element provided in an inner wall of said first chamber facing the one surface of said impeller, for attracting said first magnetic element;
a third magnetic element provided in the other surface of said impeller and attracted by said drive unit; and a fluid outlet port for allowing said fluid to flow to the outside of said housing from an opening provided in a sidewall of said first chamber, wherein during rotation of said impeller, a first attractive force acting between said first and second magnetic elements and a second attractive force acting between said third magnetic element and said drive unit are balanced with each other substantially in a center of a movable range of said impeller in said first chamber, a first groove for hydrodynamic bearing is formed in the one surface of said impeller or in the inner wall of said first chamber facing the one surface and a second groove for hydrodynamic bearing is formed in the other surface of said impeller or in said dividing wall facing the other surface, each of the first and second magnetic elements is formed annularly around a rotation centerline of said impeller, and a corner of an end surface of said first or second magnetic element is chamfered such that the first attractive force on said opening side becomes smaller than the first attractive force on an opposite side of said opening when said impeller becomes eccentric toward said opening side due to hydrodynamic force.

14. The centrifugal pump apparatus according to claim 13, wherein an outer-circumferential-side corner of the end surface of said second magnetic element is chamfered.

15. The centrifugal pump apparatus according to claim 13, wherein an inner-circumferential-side corner of the end surface of said first magnetic element is chamfered.

16. The centrifugal pump apparatus according to claim 13, wherein said drive unit includes a plurality of stator coils arranged annularly to face said third magnetic element of said impeller, for generating a rotating magnetic field and rotating said impeller, and a centerline of the rotating magnetic field generated by said plurality of stator coils matches a centerline of the sidewall of said first chamber.

17. The centrifugal pump apparatus according to claim 13, wherein said drive unit includes:

a plurality of fourth magnetic elements arranged annularly to face said third magnetic element of said impeller; and a plurality of stator coils wound around said plurality of fourth magnetic elements respectively, for generating a rotating magnetic field and rotating said impeller, and a centerline of the rotating magnetic field generated by said plurality of stator coils matches a centerline of the sidewall of said first chamber.

18. The centrifugal pump apparatus according to claim 13, wherein said drive unit includes:

a rotor rotatably provided along said dividing wall in said second chamber;

a fourth magnetic element provided in said rotor to face said third magnetic element, for attracting said third magnetic element; and a motor for rotating said rotor, and a rotation centerline of said rotor matches a centerline of the sidewall of said first chamber.

19. The centrifugal pump apparatus according to claim 13, wherein a centerline of said second magnetic element is arranged at a position different from that of a centerline of the sidewall of said first chamber such that the rotation centerline of said impeller matches the centerline of the sidewall of said first chamber during rotation of said impeller.

20. The centrifugal pump apparatus according to claim 15, wherein said fluid is blood, and said centrifugal pump apparatus is used for circulating said blood.

\* \* \* \* \*

UNITED STATES PATENT AND TRADEMARK OFFICE
CERTIFICATE OF CORRECTION

| | | |
|---|---|---|
| PATENT NO. | : 9,068,572 B2 | Page 1 of 1 |
| APPLICATION NO. | : 13/810165 | |
| DATED | : June 30, 2015 | |
| INVENTOR(S) | : Takayoshi Ozaki et al. | |

It is certified that error appears in the above-identified patent and that said Letters Patent is hereby corrected as shown below:

In the Claims:

Column 32, line 33, please delete "15," and insert --13,--.

Signed and Sealed this
Twenty-fourth Day of November, 2015

Michelle K. Lee
*Director of the United States Patent and Trademark Office*